(12) United States Patent
Py

(10) Patent No.: US 6,302,101 B1
(45) Date of Patent: Oct. 16, 2001

(54) SYSTEM AND METHOD FOR APPLICATION OF MEDICAMENT INTO THE NASAL PASSAGE

(76) Inventor: Daniel Py, 8 Normandy Rd., Larchmont, NY (US) 10538

( * ) Notice: Subject to any disclaimer, the term of this patent is extended or adjusted under 35 U.S.C. 154(b) by 0 days.

(21) Appl. No.: 09/460,050

(22) Filed: Dec. 14, 1999

(51) Int. Cl.[7] .................................................. A61M 11/00
(52) U.S. Cl. ................. 128/200.22; 128/200.14; 128/200.19; 128/200.21; 128/203.12
(58) Field of Search ................... 128/200.22, 200.21, 128/200.18, 200.19, 200.14, 203.12, 203.15, 203.22

(56) References Cited

U.S. PATENT DOCUMENTS

| | | |
|---|---|---|
| 1,156,915 | 10/1915 | Mazoyer . |
| 1,972,542 | 9/1934 | Teichmann . |
| 2,215,392 | 9/1940 | Freeman . |
| 2,228,936 | 1/1941 | Walter . |
| 2,572,383 | 10/1951 | Porter . |
| 3,099,361 | 7/1963 | Ruetz . |
| 3,245,569 | 4/1966 | Essich . |
| 3,480,169 | 11/1969 | Hammes . |
| 3,733,771 | 5/1973 | Megowen . |
| 4,220,264 | 9/1980 | Gamadia . |
| 4,313,569 | 2/1982 | Burke . |
| 4,575,375 | 3/1986 | Kozam . |
| 4,623,337 | 11/1986 | Maurice . |
| 4,694,977 | 9/1987 | Graf et al. . |
| 4,944,430 | 7/1990 | Graf et al. . |
| 4,946,452 | 8/1990 | Py . |
| 4,981,479 | 1/1991 | Py . |
| 5,024,355 | 6/1991 | Jouillat et al. . |
| 5,085,651 | 2/1992 | Py . |
| 5,133,702 | 7/1992 | Py . |
| 5,205,441 | 4/1993 | Andris . |

(List continued on next page.)

FOREIGN PATENT DOCUMENTS

| | | |
|---|---|---|
| 0 201 809 | 11/1986 | (EP) . |
| 0 492 354 | 7/1992 | (EP) . |
| 0 802 827 | 10/1997 | (EP) . |
| 2 725 247 | 10/1994 | (FR) . |
| WO 93/10852 | 6/1993 | (WO) . |
| WO 93/19806 | 10/1993 | (WO) . |
| WO 94/03135 | 2/1994 | (WO) . |
| WO 94/20408 | 9/1994 | (WO) . |

*Primary Examiner*—John G. Weiss
*Assistant Examiner*—V. Srivastava
(74) *Attorney, Agent, or Firm*—Kenyon & Kenyon

(57) ABSTRACT

A pump-type dispenser for dispensing predetermined doses of medicament in droplets or in spray form to the nasal area incorporates a rigid vial for medicament, an expandable pouch located within the rigid vial, a nasal screen, a one-way actuation mechanism, a one-way valve mechanism in the nozzle area and a spring element, both the valve mechanism and the spring element being formed as integral portions of the pump body. The nasal screen aligns the dispenser nozzle with the nasal passage and also allows the user to discreetly hide the nasal area from public view. The one-way valve mechanism in the nozzle area ensures a one-way movement of medicament from the dispenser, thereby preserving substantially perfect sterility of the medicament in the dispenser regardless of the environment surrounding the dispenser, without requiring the use of preservatives. The one-way actuation mechanism enables the user to load and dispense a uniform quantity of medicament with a uniform actuation force and speed via a single continuous motion of the actuation mechanism upon application of a very small force on the actuation trigger mechanism by the user. By preventing the pump mechanism from being left in a loaded state for a prolonged period of time, the one-way actuation mechanism prevents the spring element from experiencing the "fatigue" phenomenon. The rigid vial/expandable-pouch combination facilitates improved long term use, as well as uniformity of dosage independent of the pump orientation.

47 Claims, 37 Drawing Sheets

U.S. PATENT DOCUMENTS

| | | |
|---|---|---|
| 5,207,659 | 5/1993 | Pennaneac'h et al. . |
| 5,238,156 | 8/1993 | Andris . |
| 5,297,599 | 3/1994 | Bucheli . |
| 5,320,845 | 6/1994 | Py . |
| 5,351,862 | 10/1994 | Weag . |
| 5,358,179 | 10/1994 | Lund et al. . |
| 5,370,317 | 12/1994 | Weston . |
| 5,401,259 | 3/1995 | Py . |
| 5,462,208 | 10/1995 | Stahley et al. . |
| 5,601,077 * | 2/1997 | Imbert ............... 12/200.14 |
| 5,613,957 | 3/1997 | Py . |
| 5,692,492 * | 12/1997 | Bruna et al. ............ 128/200.23 |
| 5,702,362 * | 12/1997 | Herold et al. ............ 604/58 |
| 5,746,728 | 5/1998 | Py . |
| 5,855,322 | 1/1999 | Py . |
| 5,875,931 * | 3/1999 | Py ............... 222/137 |
| 5,979,711 * | 11/1999 | Fuchs et al. ............ 222/321 |
| 6,033,384 * | 3/2000 | Py ............... 604/186 |

\* cited by examiner

To Liquid Reservoir

SYSTEM AND METHOD FOR APPLICATION OF MEDICAMENT INTO THE NASAL PASSAGE

FIELD OF THE INVENTION

This invention relates generally to a system and method for dispensing liquid droplets or spray-pattern discharges and relates more particularly to a system and a method for dispensing droplets or spray-pattern discharges of medicinal liquids into the nasal passage, which system and method provide greater ease of application and privacy for the user, as well as increased mechanical efficiency and improved ability to prevent contamination of the stored medicinal liquids.

BACKGROUND OF THE INVENTION

Amongst various dispensers for applying medicament, a typical medicament container includes a flexible vial storage portion and a nozzle for dispensing medicament by squeezing the vial between its side walls. Another type of medicament dispenser is an accordion-like or piston-like pump dispenser which is actuated by squeezing the vial between a bottom wall and the nozzle so as to compress the vial in its longitudinal direction, rather than from its sides. An example of the piston-like dispenser which ejects precalibrated dosage of medicament is described in detail in U.S. Pat. No. 5,613,957, which is expressly incorporated herein by reference.

In recent years, pump-type dispensers have received attention for their use in accurately dispensing small doses of medicaments, e.g., for nasal applications. One persistent problem associated with pump-type dispensers for dispensing medicaments is preventing contamination of the medicament which can occur when the medicament that has been exposed to ambient air returns and/or remains in the outlet channel, e.g., within the nozzle. One solution to this problem is to simply add preservatives to the medicament being dispensed, thereby preventing bacterial growth. However, this solution has obvious disadvantages, e.g., added costs and toxicity of the preservatives. In order to prevent bacterial growth in medicament which does not contain preservatives while allowing dispensation of multiple doses of the medicament, the nozzle must prevent any medicament that has been previously exposed to ambient air from being reintroduced, or "sucked back," into the outlet channel of the nozzle, i.e., prevent any "dead volume." "Dead volume" is defined herein as the volume of space within the outlet channel of the pump where medicament can come into contact with the open air and remain. If any residual medicament remains within the dead volume, this residue could serve as a host environment for germ growth.

Another consideration involved in designing pump-type dispensers for medicaments is ensuring accurate dispensation of a predetermined quantity of medicament, e.g., ranging from 5 $\mu$l to greater volumes, upon each actuation of the dispenser, irrespective of the orientation of the dispenser or the force applied by the user to the actuation mechanism of the dispenser. While many pump-type dispensers provide an upper limit of the quantity of medicament dispensed upon each actuation of the dispenser, these pumps often dispense varying quantities of medicament as a function of the speed and/or force of actuation of the actuation mechanism of the dispenser. In the case of a pump-type dispenser which generates aerosol or spray-type discharges, not only will the dispensed dose of medicament vary with the speed and/or the force of actuation of the actuation mechanism, but the spray pattern, or the plume, of the dispensed medicament will also vary with the speed and/or the force of actuation.

It should also be noted that persons who suffer from asthmatic or allergic condition routinely need to carry a medicament dispenser with them for emergency situations, but both the existing pressurized medicament dispensers and non-pressurized dispensers have significant drawbacks. The pressurized dispensers are not always ready for use unless they incorporate a heavy glass bottle sustaining vacuum. The non-pressurized devices generally require a particular orientation for dispensing medicament, as well as suffering from a measurable dead volume in the nozzle area.

Yet another problem in designing pump-type dispensers for medicaments is ensuring the ease of applying the medicament. Conventional pump-type dispensers for nasal application, an example of which is shown in FIG. 2, are generally actuated by compression along the length of the dispenser. As shown in FIG. 2, the conventional nasal pump 200 is actuated by pushing down on the syringe arms 203 while supporting the bottom portion 202 with the thumb. The combined actuation motion leads to difficulty in holding the nasal pump in stationary position, and usually results in removal of the nozzle tip 204 from the nostril area. For those users who may have greater than average difficulty with the actuation motion, e.g., elderly patients with arthritis or young children, accidental application of the nasal medicament to the face or into the eye may occur.

Yet another problem associated with the pump-type medicament dispensers is manufacturing complexity: pump-type medicament dispensers are currently made of numerous parts and are highly delicate to assemble. As the number of components increases, the difficulty and cost of mass production increases correspondingly. For example, many of the pump-type dispensers incorporate springs, which pose problems in the manufacturing process because of the springs' tendency to get intermingled. In addition, very small size of the gaskets and other components make relative movement of the parts difficult. Furthermore, increased number of components also increases the complexity of achieving stability and compatibility of the component materials with the medicament.

One attempt to solve the above-described problems associated with applying medicament from a dispenser is described in my U.S. Pat. No. 5,267,986, which discloses a system including a cartridge for actuating a piston-like or accordion-like vial-dispenser for applying medicament to an eye. The cartridge disclosed in U.S. Pat. No. 5,267,986 includes: a housing for holding the vial-dispenser, a telescoping cylinder for compressing the vial-dispenser in the longitudinal direction to load the vial with medicament; a locking mechanism for locking the telescoping cylinder and the vial-dispenser in the loaded position, against the urging of a spring mechanism of the vial-dispenser; and a trigger mechanism for releasing the telescoping cylinder and the vial-dispenser from the locked position to release the medicament loaded in the dispenser by means of the force of the spring mechanism. In order to obviate the need for a discrete spring element in the pump mechanism of the vial-dispenser, a portion of the vial-dispenser body is made of an elastic material which is compressible and provides spring force. The two-step process in which the cartridge disclosed in U.S. Pat. No. 5,267,986 loads and subsequently releases the medicament from a vial-dispenser defines the basic operation a "reverse pump," an example of which is described in U.S. Pat. No. 5,613,957.

The dispensing system disclosed in U.S. Pat. No. 5,267,986 addresses some of the previously-mentioned problems by enabling a user to apply a predetermined dose of medicament independent of the physical force, or speed, applied to the dispensing system by the user: the releasing force or speed of the dispensed medicament is dependent on the integral spring element of the dispensing system. Whereas conventional pump-type dispensers often utilize compression along the longitudinal axis for release of medicament, the actuation motion of the release mechanism described in U.S. Pat. No. 5,267,986 is preferably achieved in a direction perpendicular to the longitudinal axis of the vial-dispenser to ensure enhanced leverage for the user.

While the dispensing system disclosed in U.S. Pat. No. 5,267,986 addresses some of the previously-mentioned problems, at least one significant problem remains: because elastic materials, particularly elastomeric materials and springs, tend to exhibit hysteresis, spring force decreases if the spring mechanism is kept in the compressed position, i.e., in the loaded, locked position. Although the deformation of spring is generally reversible if the spring is returned to, and maintained in, the unbiased state for some period, some of the deformation becomes irreversible, or experiences "creep," if the spring is kept in the compressed state beyond a certain threshold period of time, which threshold period varies with the spring material. The amount of loss of spring force is dependent on the tendency of a particular spring material to "creep," and it is known that metal springs tend to exhibit much less "creep" than plastic springs. The hysteresis of elastic materials used to form the spring mechanism of the pump described in U.S. Pat. No. 5,613,957 is due to loss of some of the spring property when the spring element remains in the compressed state for an extended, and often unexpected, period of time.

Two examples illustrate the practical implications of the above-mentioned hysteresis problem in connection with the dispensing system disclosed in U.S. Pat. No. 5,267,986. As a first example, a user places the dispensing system in the loaded state but does not actuate the release mechanism for several hours due to an interruption. When the release mechanism is finally actuated, hysteresis of the spring mechanism causes the dosage of released medicament to vary from the dosage calibrated to be released under normal conditions. As a second example, a user places the dispensing system in the loaded state but subsequently forgets about the loaded system; the user does not actuate the release mechanism for several weeks or months. In this situation, not only will the initially-released dosage vary from the calibrated dosage, due to lower actuation speed or force, but subsequently-dispensed dosages will also vary from the calibrated dosage due to a type of permanent deformation, or "creep," that has occurred, i.e., a permanent change in the actuation stroke. In view of the above-described problem of spring deformation, it would be desirable to have a pump-type medicament-dispensing system which allows the user, by means of a single actuation motion, to load the vial with medicament and subsequently dispense the medicament, without any intervening locking step.

Pump-type dispensers for applying nasal medicaments are faced with yet another problem in providing the users with some level of discreetness: the sight of a conventional pump-type nasal dispenser positioned inside of a nostril is unseemly and often causes embarrassment for the user. Accordingly, it would be desirable to achieve dispensation of nasal medicament without presenting the unsightly appearance of the dispenser positioned inside the nostril.

Still another problem faced by pump-type dispensers is achieving a tight seal of the dispenser after filling it with liquid. The standard approach is to utilize plugs or lids which are formed to mechanically engage the filling opening of a pouch or a container. The main difficulty with this approach is that the allowable mechanical tolerances of the interacting parts of the plug or lid and the opening of the pouch or the container must be extremely small in order to achieve a tight, substantially hermetic seal. Furthermore, even if the interacting parts initially form a tight seal, the portions of the interacting parts which are under pressure tend to experience a "creep," i.e., deformation of the material, over time. Accordingly, the "creep" phenomenon tends to reduce the tightness of the seal. Thus, there is a need for a mechanical closure system which achieves and maintains a hermetic seal of a pouch or a container over the life of the container.

Accordingly, it is an object of the present invention to provide a pump-type dispenser for dispensing medicament in droplets or spray form, which dispenser facilitates easy application of the medicament while ensuring positional stability of the dispenser during the actuation motion.

It is another object of the present invention to provide a pump-type dispenser for applying medicaments into the nasal passage, which dispenser provides the user with a nasal screen for discreetness.

It is yet another object of the present invention to provide a pump-type dispenser for applying medicaments into the nasal passage, which dispenser provides a guide for aligning the dispenser nozzle with the nasal passage.

It is yet another object of the present invention to provide a pump-type dispenser for applying medicament into the nasal passage, which dispenser ensures a one-way movement of medicament through the nozzle of the dispenser.

It is yet another object of the present invention to provide a pump-type dispenser which has a substantially zero "dead volume" in the nozzle portion so that no medicament which has been exposed to ambient air can remain, i.e., the medicament is completely released once it passes through the outlet nozzle, or the combined effect of the surface tensions of the medicament and the surrounding outlet nozzle forces any remaining medicament out of, and away from, the outlet portion.

It is yet another object of the present invention to provide a pump-type dispenser for dispensing nasal medicament, which dispenser minimizes the number of parts for manufacturing.

It is yet another object of the present invention to provide a pump-type dispenser for nasal medicament, which dispenser incorporates a nozzle adapted to generate an aerosol-type discharge by means of elastic, radial deformation along the circumference of the nozzle which simultaneously functions as an integral spring and an elastic valve, while substantially maintaining the physical profile in the direction of the longitudinal axis of the nozzle.

It is yet another object of the present invention to provide a pump-type dispenser for nasal medicaments, which dispenser does not require propellants such as CFCs, the release of which is harmful to the ozone layer, or the release pressure of which propellant is temperature dependent, thereby creating variations in dispensed dosages.

It is yet another object of the present invention to provide a pump-type dispenser for nasal medicaments, which dispenser emits a predetermined dose of medicament upon each actuation of the dispenser, irrespective of the orientation of the dispenser and the force applied by the user to actuation mechanism.

It is yet another object of the present invention to provide a pump-type dispenser for nasal medicaments, which dispenser emits a predetermined dose of medicament upon each actuation of the dispenser, irrespective of the force applied by the user to the actuation mechanism of the dispenser.

It is a further object of the invention to provide a nasal-medicament dispensing system which can accurately deliver a small, calibrated amount of medicament by means of a single actuation motion which loads the system with medicament and subsequently dispenses the loaded medicament immediately thereafter without any intervening locking step.

It is a further object of the invention to provide a nasal-medicament dispensing system having a single actuation motion for loading and dispensing the medicament, which system incorporates an elastomeric spring element as an integral portion of the body of the dispensing system.

It is a further object of the invention to provide a nasal-medicament dispensing system which includes an actuation mechanism for actuating a vial-dispenser of the type having a spring configuration, e.g., an accordion-like or piston-like vial-dispenser, which actuation mechanism requires minimal force for actuation.

It is a further object of the invention to provide a nasal-medicament dispensing system which substantially eliminates any possibility that spring elements of the dispensing system will exhibit hysteresis of spring characteristics.

It is a further object of the invention to provide a nasal-medicament system in which the actuation motion of the actuation mechanism for dispensing the loaded medicament is in the direction perpendicular to the longitudinal axis of the vial dispenser to ensure enhanced leverage for the user and to avoid the actuation motion being parallel to the compression axis of the spring element.

It is a further object of the invention to provide a method of accurately delivering a small, calibrated amount of medicament by means of a single actuation motion of a medicament-dispensing system which loads the system with medicament and immediately dispenses the loaded medicament thereafter without any intervening locking step.

It is a further object of the invention to provide a method of dispensing a small, calibrated amount of medicament by means of an actuation mechanism for actuating an accordion-like or piston-like vial-dispenser, which actuation motion requires minimal force for actuation.

It is another object of the present invention to provide a mechanical closure system for achieving a tight, substantially hermetic seal of a pouch or a container having an opening.

It is another object of the present invention to provide a method of mechanically sealing a pouch or a container having an opening to achieve a tight, substantially hermetic seal while simultaneously allowing delivery of gels or suspensions via an outlet nozzle.

It is yet another object of the present invention to provide a mechanical closure system for a pouch or a container having an opening, which mechanical closure system compensates for deformation of the interacting parts of the mechanical closure system and the pouch or the container.

It is yet another object of the present invention to provide a mechanical closure system for achieving a tight, substantially hermetic seal of a pouch or a container having an opening, which system does not require extremely small tolerances for the interacting parts.

It is yet another object of the present invention to provide a method of mechanically sealing an opening of a pouch or a container after having introduced liquid into the container through the opening, which method eliminates the need to provide vacuum conditions for filling the container and, thereby, substantially reduces the cost of the mechanical system for filling the container.

It is yet another object of the present invention to provide a method of mechanically sealing an opening of a pouch or a container, which method involves removably sealing the opening of the pouch or the container in a first configuration, and permanently sealing the opening of the pouch or the container in a second configuration.

It is yet another object of the present invention to provide a system of mechanically sealing an opening of a pouch or a container, which system provides a single-piece sealing element consisting of a mechanical plug detachably coupled to a crimping element via a flange for removably sealing the opening of the pouch or the container, and the system further providing that the crimping element may be detached from the mechanical plug to permanently seal the opening of the pouch or the container.

It is yet another object of the present invention to provide a spray-type dispensing system having a swirling chamber in the region of the nozzle for generating a spray pattern, which system substantially minimizes the head loss in the swirling chamber and in the outflow channels surrounding the swirling chamber.

It is yet another object of the present invention to provide method of generating a spray-type emission from a medicament dispensing system having a swirling chamber in the region of the nozzle for generating a spray pattern, which method substantially minimizes the head loss in the swirling chamber and in the outflow channels surrounding the swirling chamber.

SUMMARY OF THE INVENTION

In accordance with the above objects, the present invention provides a pump-type dispenser for dispensing predetermined doses of medicament in droplets or in spray form to the nasal area, which pump-type dispenser incorporates a nasal screen, a pump mechanism, a one-way valve mechanism in the nozzle area, a one-way actuation mechanism and an integral spring element. The nozzle area, which includes the one-way valve mechanism, is adapted to minimize the head loss experienced by the liquid in the nozzle area, thereby achieving more efficient fluid mechanics. The nasal screen not only guides and correctly aligns the dispenser nozzle with the nasal passage, but the screen also serves the important function of allowing the user to discreetly apply the nasal medicament from the dispenser without exposing the nasal area to the public. Furthermore, the one-way valve mechanism in the nozzle area ensures a one-way movement of medicament from the dispenser, thereby preserving substantially perfect sterility of the medicament in the dispenser regardless of the environment surrounding the dispenser, without requiring the use of preservatives.

The one-way actuation mechanism enables the user to sequentially load and dispense the medicament with a single continuous motion of the actuation mechanism upon application of a very small force on the actuation trigger mechanism by the user. The use of the one-way actuation mechanism also enables design simplification by allowing replacement of the traditional metallic spring element with a spring element formed as an integral part of the dispensing system and made from the same elastomeric material as the valve material. The actuation mechanism operates transversely to the length of the dispenser, thereby minimizing the risk that the user will accidentally remove the dispenser nozzle from the nose during use. In addition, the integral spring element formed as a portion of the pump body minimizes the number of component parts for the dispenser, thereby minimizing the manufacturing complexity and the likelihood of mechanical failure during use. Furthermore, the one-way actuation mechanism and the integral spring element provide the dispenser according to the present invention with the unique characteristic of delivering the same precise quantity of medicament at the same actuation force and speed, regardless of the actual force applied to the actuation trigger by the user.

As can be seen from the above, the pump-type dispenser according to the present invention provides a safe, stable and easily operable mechanism for applying medicament to the nasal area. As an additional advantage, the pump-type dispenser according to the present invention for dispensing nasal medicament may be used with substantially all types of liquid formulations, e.g., solutions, suspensions and gels. An exemplary pump mechanism incorporated in the dispenser according to the present invention has: a) a pump body having a front end or tip on the fluid outlet side, the front end comprising an outlet orifice sealed off by an elastic membrane, and continuing backwards through a pump duct with a fluid inlet orifice; and b) a movable piston fitted inside the pump body, the relative displacement of the end of the piston in relation to the pump body between the inlet orifice and a stop position located towards the outlet orifice thus determining the quantity of fluid expelled on displacement, the end of the piston fitting hermetically by slight friction against the duct, the inlet orifice being of a sufficient size for only the preset quantity of fluid or gel to be trapped at the end of the pump duct for its expulsion through the outlet orifice, the pump body and the piston being totally enveloped by an elastic phial, with the exception of the front end of the pump body.

The front end of the pump body, i.e., the tip or "nose," incorporates an outlet orifice preferably in the form of, for example, a cylindrical channel, opening into a pump duct, the latter being, for example, a cylindrical tube, the outlet orifice or channel and pump duct preferably lying in the same general direction. The outlet orifice is preferably a channel advantageously positioned essentially axially along the length of the pump. However, as is clear to those skilled in the field, the channel may be of any shape, e.g., an elbow shape, so as to ensure a projection perpendicular to the axis of the pump.

The elastic membrane may be made of any well-known state-of-the-art elastic material, for example rubber, an elastomer, and preferably thermo-elastic materials such as polyurethane, Adrian®, or those available from AES under the name of VISKAFLEX®, from DUPONT under the name of ALCRYN® or HYTREL®, from DSM under the name SARLINK®, from SHELL under the name KRATON®, and from Monsanto under the name Santoprene®. The elastic membrane has, at the outlet orifice, a sufficient thickness to form a one-way valve towards the outlet. In other words by working the piston towards the outlet orifice, the force exerted on the piston enables the said valve to open thus enabling the fluid to be expelled. By contrast, after expelling the liquid, if the piston is then drawn back the valve becomes hermetically sealed and, in the pump duct, a reduced pressure or vacuum is created.

The pump duct has a fluid inlet orifice enabling the fluid to fill through the latter. This inlet orifice may be of any shape, rounded, elongated, and may be in the shape of a channel, a slit, a groove, etc.

Similar to a syringe, the pump mechanism according to the present invention incorporates a movable piston fitted inside the pump body; the piston is preferably fitted along the length of the device. "Movable" simply indicates that the piston is movable in relation to the body in which it is housed, without prejudicing which element, i.e., the piston or body, moves. This piston can move between a stop position located towards the fluid outlet orifice, and a position beyond the fluid inlet orifice. The stop may be, as in a conventional syringe, the end of the pump duct on the outlet side. However, another stop may be made, if desired, before this end. In the first case, after the fluid is expelled by the relative working of the piston and pump body, the volume of fluid held between the outlet valve and the piston end will be reduced merely to the volume of the evacuation channel. In the second case, the volume of fluid held between the outlet valve and the piston end will include a certain portion of the pump duct in addition to the evacuation channel.

As in a conventional syringe, the end of the piston of the pump according to the present invention fits hermetically by slight friction against the pump cylinder. It will thus be understood that when the piston is drawn in the opposite direction to the outlet orifice, a reduced pressure is created in the pump duct, the said reduced pressure being "broken" when the end of the piston reaches the level of the fluid inlet orifice. At this point the fluid is sucked into the pump duct which it fills. During the relative displacement of the piston towards the outlet orifice, when the piston goes beyond the inlet orifice, it thus traps in the pump duct a certain volume of fluid. The set volume between this position and the most extreme, stop position of the movable piston corresponds to the preset quantity of fluid which will be expelled by the pump. The compression of the fluid by the piston, the compression being achieved, for example, and preferably with the aid of an elastic, or by pressure with the aid of the thumb on the piston, enables the elastic membrane forming a valve to open and the fluid to be expelled.

The volume of formulation to be delivered by the exemplary phial-pump incorporated in the present invention is small, for example in the order of 5 $\mu$l.

As can be seen from the above, the rest position of the pump according to the invention is the position where the piston is at the stop. This is why preferably the pump according to the invention has an elastic means of returning the piston to the stop position. These elastic means are well known to those skilled in the field and are such as a spring, the said spring being fitted inside or outside the pump, along the piston's axis of displacement; the spring may be made of a metal or plastic material, the nature of the spring being adapted to the fluid contained in the bottle when the said spring is fitted inside the phial in contact with the fluid.

The above-mentioned elastic means may be formed as a part of the envelope of the elastic phial itself, for example, in the form of a concertina, or annular convex part of sufficient thickness to form a mean of return. The envelope is for example at this level integral on one side with the pump body and on the other side with the piston by means of rings with which these element may be fitted. These rings can cooperate with corresponding slots which in this cage are made in the envelope. If desired, in order to strengthen the means of return it is possible to use, for example, two return element such as concertinas located more particularly on either side of the retaining ring, integral with the piston a illustrated below. The elastic membrane may be alternatively a separate piece from the elastic phial. However, in preferred conditions of embodiment of the pump mechanism described above, the elastic membrane and the elastic phial form a single piece. The number of pieces of the pump mechanism according to the invention may therefore be remarkably reduced. Indeed, according to the invention, it is possible to have a pump mechanism incorporating just three pieces: a phial made of an elastic material; the pump body and the piston.

The exemplary pump mechanism according to the present invention has a pump body with a frontal ring, fitted close to the fluid outlet. Such a frontal ring enables the elastic phial to be hermetically fixed to the pump body. Such a ring also enables the embodiment of elastic means for returning the piston to the stop position. The pump body may also include a rear ring, which can perform several functions. The rear ring is preferably an incomplete ring, i.e., portions of the ring are cut out.

The above-described piston has the general conformation of an elongated element, corresponding to conventional piston, the elongated element having a plurality of elements, preferably three, in the shape of a ship's anchor, each thus forming a radial element, at the end of which is an arc-shaped element. The plurality of arcs then forms the incomplete ring referred to above. In such a case, for example, the pump body comprises a cylindrical element, comprising at its front end a ring and at its rear end another cylindrical ring, of larger diameter than the diameter of the arcs described above, the front base of the rear cylindrical ring being cut away so that the above anchors can pass through the base of the cylinder thus enabling, by means of slots corresponding to the above radial elements, and made in the cylinder comprising the pump body, the longitudinal displacement of the piston.

The slots made in the pump body perform two functions: a) on the one hand, they enable the displacement of the piston, by the radial elements sliding along the axis of the slots; and b) on the other hand, the end of the slots on the front side constitutes the fluid inlet orifice enabling the fluid to reach the final pump duct corresponding to the preset volume of fluid to be expelled.

The above-described shape of the piston facilitates the following: a) enable the nozzle portion to be integral with the rear portion of the pump body; b) eliminates the need for the nozzle portion to be snapped into the housing when the piston is moved towards the rear; and c) enables the pump mechanism to be interchangeable within the same housing. The shape of the piston also enables the piston to be actuated through the bellows portion serving as the spring element, without causing or resulting in any motion of the rear vial portion of the pump mechanism. One advantage resulting from the lack of motion involving the rear vial portion is that the pump mechanism does not experience any momentum change as a function of the fluid-content level of the vial, i.e., the pump mechanism exhibits the same momentum characteristics whether the rear vial portion is full or nearly empty, thereby ensuring substantially constant dosage.

In addition to the above-noted advantages, the pump mechanism according to the present invention may also incorporate two O-shaped rings which are secured around the circumference of the pump piston, such that the O-shaped rings provide a fluid-tight seal between the piston and the surrounding sleeve portion of the pump body. The O-shaped rings, which may be made of silicone, polyisoprene, Kraton™, Adrian™, butyl or any rubber-like material, maintain the bellows chamber free of fluid by providing a fluid-tight seal between the pump piston and the surrounding sleeve portion of the pump body. In turn, the absence of fluid in the bellows chamber substantially eliminates the possibility of fluid hindering the elastic deformation of the rear bellows portion.

The dynamics of a pump according to the present invention are summarized below. Let us assume that the equilibrium position is the position in which the piston is at the stop. As is clear for the man skilled in the art, the displacements referred to in the present application are in general relative displacements. Indeed preferably, the piston may be kept stationary and the pump body moved as illustrated below, or the pump body kept stationary and the piston moved to achieve the outlet of the fluid. When the piston draws back, it creates a cavity whose state of pressure is a partial vacuum, indeed the outlet orifice is blocked off by the elastic membrane, preventing the entry of air into the pump. On drawing back further, the piston ends up by reaching the level of a fluid inlet orifice. At this point the pump duct, also referred to as a "drop cavity" or "dose chamber," quickly fills with fluid. The piston can then be pushed back or left to move on to the stop position. When the piston again reaches the level of the fluid inlet orifice, on reaching the end of the latter, it traps a preset volume of fluid. The volume between this extreme position and the stop position of the piston then determines the quantity of fluid expelled. From this moment, ejection of the fluid occurs. As soon as the annular piston lip contacts the compression chamber, the valve opens.

A pump mechanism according to the invention has many advantages which it also confers to an elastic phial fitted with such a pump. The preset volume proposed for the pump may be adjusted by altering both the cross-sectional area of the cavity or pump duct and the length of this cavity by changing the depth of the inlet orifice. The dose is constant and depends neither on gravity nor the activation speed of the pump. It can only depend on the spring effect given to the relative pump body/piston movement, and this for a given viscosity and orifice diameter.

The use of an elastic wall for the envelope makes it possible to achieve in one piece the following functions. First, a one-way valve function is facilitated, enabling operation without drawing in air or the actual substance being delivered; the pump also makes it possible to dispense formulations without preservative which may be used repeatedly without the risk of contamination of the inside of the phial. Second, a phial function is facilitated: the elasticity of the wall in fact enables the wall to cave in gradually as the liquid is evacuated by the pump. Third, the elastic wall functions as an integral spring element.

The injection or filling of the above-described pump mechanism may be associated with a suction which precedes and/or accompanies and/or follows filling so as to eliminate any residual gas in the phial after filling. The dose delivered on each activation of the pump mechanism does not vary, whatever the ambient pressure, because substantially no gas exists inside the system, and the expulsion force applied to the liquid is not dependent on the manual force applied by the user.

The pump-type dispenser mechanism according to the present invention may further incorporate an inner pouch made of an elastic material, e.g., Kraton™, and located within the vial portion. The vial portion, in this case, may be made of a rigid material which substantially eliminates ingress of air into the vial portion. The interior of the inner pouch contains varying volume of air, depending on the amount of liquid contained in the vial portion. The elastic inner pouch is collapsible such that its bottom exterior surface conforms to the liquid level in the vial portion. Accordingly, when the vial portion is completely filled with fluid, the inner pouch is substantially completely collapsed and the volume of the interior is substantially zero. As the liquid in the vial portion is gradually depleted as the result of the pump operation, the inner pouch expands correspondingly, drawn by the suction pressure in the vial portion, thereby substantially eliminating the residual air inside the vial portion, which residual air may adversely affect the operation of the pump. The volume of air in the inner pouch is in turn regulated via air holes.

One embodiment of the pump-type dispenser mechanism according to the present invention may also incorporate a nozzle mechanism for generating an aerosol-type liquid discharge, which nozzle mechanism ensures one-way movement of liquid and also has a substantially zero "dead volume" at the tip of the nozzle. The nozzle mechanism according to the present invention is not only suitable for dispensing nasal medicaments, but may be also adapted for use with a variety of types of liquid-dispensing apparatuses, for example, medicament dispensers which channel liquid from a liquid reservoir through the nozzle mechanism by application of pressure via a pump mechanism.

One embodiment of the nozzle mechanism includes a flexible nozzle portion with an outlet and fluid channels, a rigid shaft received within the flexible nozzle portion, and a rigid housing surrounding the flexible nozzle portion and exposing the outlet. The rigid shaft interfaces the outlet to form a second normally-closed, circumferential valve as well as to define a collecting chamber, or a "swirling chamber," for temporarily collecting the liquid which has been channeled from the liquid reservoir, prior to being discharged via the outlet. The outlet has an elastic outer wall, the thickness of which decreases along the elongated axis of symmetry of the outlet from a bottom portion of the outlet toward the tip of the outlet, thereby facilitating one-way movement of liquid through, and out of, the outlet.

In the above-described embodiment of the nozzle mechanism, the fluid channels, which define a portion of a fluid communication path between the liquid reservoir and the collecting chamber, are positioned at various radial edge or circumferential points within the flexible nozzle portion. The radially positioned fluid channels provide uniform pressure with a minimum of "head loss" which will be explained later. As a result, the liquid pressure is uniformly applied at the entry point of the swirling chamber once the pressure within the radially positioned fluid channels reach a threshold pressure sufficient to radially deform a first normally-closed, annular or circumferential valve forming a portion of the fluid communication path between the liquid reservoir and the collecting chamber, which first normally-closed valve is described in further detail below. It should be noted that while the first normally-closed valve is positioned annularly, i.e., applies even pressure at all points of the circumference, the fluid channels extend along the longitudinal axis of the flexible nozzle portion and occupy only small sections of the circumference of the second normally-closed valve.

The above-mentioned swirling chamber is used to create a spray pattern for the discharged liquid. The greater pressure differential between the outside and the inside of the pinhole opening of the swirling chamber, the greater the homogeneity and the smaller the spray-particle size. In order to minimize the source of resistance, also referred to as "head loss" in fluid mechanics, the length of the fluid channel incorporated in the present invention is minimized, as well as the rate of reduction of the fluid-channel width (if any) and the rate of change of the fluid-channel angle relative to the swirling chamber.

The above-described embodiment of nozzle mechanism according to the present invention may be coupled to a flexible body portion which has a substantially tubular shape and a wall thickness which decreases from the bottom of the body portion toward the flexible nozzle portion, along the elongated axis of symmetry of the body portion. The rigid shaft received within the flexible nozzle portions extends down into the flexible body portion so that a second portion of the rigid shaft interfaces the flexible body portion to form the first normally-closed, radially-positioned valve in the fluid communication path between the liquid reservoir and the collecting chamber. As with the second normally-closed, radially-positioned valve, the first normally-closed, radially-positioned valve is opened when the pressure on the liquid in the fluid communication path reaches a threshold pressure sufficient to radially deform the portion of the flexible body portion forming the first normally-closed, radially-positioned valve.

One advantage of the nozzle mechanism according to the present invention is that the configuration of the outlet portion substantially eliminates the possibility that liquid in the nozzle mechanism will come in contact with ambient air and subsequently return and/or remain in the interior portion of the nozzle mechanism. The nozzle mechanism achieves this result by means of the second normally-closed valve, which facilitates one-way movement of liquid from the nozzle mechanism through the outlet portion during discharge. Due to the second normally-closed valve, the outlet portion has a substantially zero "dead volume", i.e., a space in which liquid that may have been exposed to ambient air can remain.

In addition to the second normally-closed valve, the first normally-closed valve positioned along the fluid communication path between the liquid reservoir and the nozzle mechanism adds further assurances that liquid in the liquid reservoir will not be contaminated by the ambient air and subsequently reintroduced into the nozzle mechanism. Because the first and second normally-closed valves are positioned along the fluid communication path to open asynchronously during fluid communication leading to discharge through the outlet, failure of either one of the valves will not affect the integrity of the nozzle mechanism to prevent contamination of the liquid in the liquid reservoir.

Another advantage of the nozzle mechanism according to the present invention is that the nozzle mechanism experiences substantially no deformation along the direction of the discharge path through the outlet, i.e., the elongated axis of symmetry for the outlet. As a result, the physical profile of the fluid channel, which induces swirling action of the liquid in the collecting chamber of the nozzle mechanism, is maintained during liquid discharge.

Another advantage of the nozzle mechanism according to the present invention is that the number of parts which constitute the nozzle mechanism and, in turn, the dispensing system which includes a pump mechanism in combination with the nozzle mechanism, is significantly reduced in comparison to conventional nozzle mechanisms. The reduced number of parts reduces costs and complexity of assembly.

The pump-type nasal medicament dispenser according to the present invention incorporates an exterior housing and a cartridge positioned within the housing, which cartridge is in turn particularly adapted for actuating an accordion-like or piston-like vial-dispenser mechanism. The vial-dispenser has an accordion-like front bellows portion near the anterior end, a rear vial section or liquid storage chamber at the posterior end, and a rear bellows portion located between the front bellows portion and the rear vial section. A drop cavity or a dosage cavity, which may be located within either the front bellows portion or the rear bellows portion, holds a precalibrated amount of medicament loaded from the liquid storage chamber. In addition, an internal piston mechanism within the vial-dispenser acts in concert with the front and rear bellows portions to expel the medicament contained in the drop cavity.

The cartridge includes a generally elongated body portion which is adapted to receive the vial-dispenser between an anterior wall and a posterior wall of the cartridge. The posterior wall of the cartridge may form a portion of a rear chamber of the cartridge, in which case the rear chamber of the cartridge receives the rear vial section of the vial-dispenser. The anterior wall of the cartridge has an aperture for exposing the nozzle of the vial.

Located on top portion of the cartridge is a trigger mechanism which, when depressed, acts via, and in concert with, a notched lever located in the interior portion of the housing to extend the front bellows portion and compress the rear bellows portion of the vial-dispenser in the longitudinal direction, away from the anterior wall of the cartridge and towards the rear chamber. In the case of the exemplary embodiment of the vial-dispenser described herein, extension of the front bellows portion and compression of the rear bellows portion cause a precalibrated dose of medicament to enter the dosage cavity located in the front of the dispenser, thereby "loading" the dosage cavity.

Continuing with the triggering motion, once the notched lever located in the interior portion of the cartridge has extended the front bellows portion of the vial-dispenser a predetermined distance, the notched lever is disengaged from the front bellows portion by a wedge-shaped arm extending from the rear wall of the cartridge. Upon disengagement from the notched lever, the front bellows portion contracts and the rear bellows portion extends towards the anterior wall of the cartridge. In concert with the movements of the front and rear bellows portions, movement of the internal piston mechanism creates pressure which forces the medicament from the dosage cavity via the anterior nozzle of the vial-dispenser.

The present invention also provides an exemplary embodiment of a mechanical lid or a plug which interacts with an opening of the rear vial section of the vial-dispenser mechanism, as well as with a rigid ring placed inside the vial opening. The mechanical plug is snapped into the vial opening such that the mechanical plug compresses both the outside of the opening and the inner face of the ring placed inside the vial opening, thereby forming a tight seal of the opening.

The opening area of the vial has an annular recess configured to accommodate the rigid ring, where the rigid ring is snapped into the annular recess. After the rigid ring has been snapped into the annular recess of the opening region of the vial, the mechanical plug is snapped both into the rigid ring and around the outside edge of the vial opening so that the vial opening is compressed between the rigid ring and the mechanical plug. The radial edge of the inner face of the mechanical plug is formed as an arch-shaped region which extends around the plug such that the radial edge of the plug is adapted to "hug" the perimeter of the vial opening. In addition, attached to the inner face of the mechanical plug are two or more legs which extend perpendicular to the lower surface of the mechanical plug. The ends of the legs are hook-shaped to engage the bottom of the rigid ring/radial groove combination. The annular recess and the legs of the mechanical plug facilitate both vertical and radial compression of the opening region of the vial and the rigid ring. In this manner, a tight seal of the vial opening is ensured.

In addition, the outside surface of the opening region of the vial and the interior surface of the annular recess of the mechanical plug each has one or more protrusions, or "interferences." Once the mechanical plug has been snapped into the vial opening, the resulting compression of the vial material tends to cause displacement, or "creep," of the compressed material towards areas of lesser compression. The protrusions limit the range of displacement of the compressed vial material, i.e., force the vial material displaced by compression to remain within a defined area, thereby ensuring the tightness of the seal for a prolonged period of time.

The central inner surface of the mechanical plug may be equipped with an extension or a plunger which is adapted to extend into the liquid content of the vial in such a way that the mechanical plug snaps tightly into the vial opening after, and only after, the plunger has displaced the surface level of the liquid up to the upper edge of the vial opening, thereby obviating the need for a vacuum condition normally utilized for an airless filling process. In this manner, the plunger substantially reduces the residual air bubbles which may otherwise remain between the surface of the liquid and the inner surface of the mechanical plug.

As an alternative to the above-described mechanical closure system, the present invention also provides a rigid crimping element detachably coupled via a breakaway flange to a rigid mechanical plug. These elements may be molded as a single piece in order to simplify the manufacturing and assembly process.

The mechanical plug is first inserted into an opening of a neck of the rear vial section of the vial-dispenser mechanism. The mechanical plug and an interior portion of the neck of the vial interact to maintain the mechanical plug within the neck of the vial. However, a predetermined amount of force may dislodge the mechanical plug from the neck of the vial. This detachable engagement between the mechanical plug and the neck of the vial allows the vial to be temporarily sealed for some operations and open for other operations.

In order to permanently and effectively seal the vial, the crimping element is then repositioned relative to, e.g., detached from, the mechanical plug and slipped over the neck of the vial, which action results in compression of the neck of the vial between an inner face of the crimping element and an external face of the mechanical plug, thereby providing a tight, hermetic seal of the vial.

The neck of the vial may be annular and has an inner wall and configured to engage the mechanical plug. A first semicircular protrusion extends substantially around the entire circumference of the inner wall of the neck to engage a first groove on the mechanical plug so that, when the mechanical plug is inserted into the opening of the neck, the first protrusion on the mechanical plug "snaps" into the first groove on the mechanical plug. This first step of "snapping" the first protrusion into the first groove is reversible so that sterilization of the vial using β or γ radiation can take place with the first protrusion snapped into the first groove, and the plug can be detached from the neck, i.e., by releasing the first protrusion from the first groove, for subsequent filling of the vial.

A second protrusion extends around an outer wall of the neck of the vial and is configured to engage the crimping element. The second protrusion consists of a semicircular portion extending substantially around the entire circumference of the outer wall of the neck to engage a second groove on the crimping element. When the crimping element is slipped over the neck of the vial, the second protrusion on the neck of the vial "snaps" into the second groove on the crimping element to securely couple the crimping element to the neck of the vial. Once the crimping element is "snapped" into place, the neck of the vial is then compressed between the crimping element and the mechanical plug to provide a tight seal of the vial. This second step of "snapping" the crimping element onto the vial is irreversible, thereby forming a permanent seal.

The interacting surfaces of the crimping element and the neck of the vial have complementary contours which ensure distribution of the compressive force over the entire region of the interacting surfaces when the crimping element is engaging the neck of the vial. In this manner, the present invention substantially eliminates the "creep" phenomenon exhibited by prior art closure mechanisms.

In order to further maintain the crimping element on the neck of the vial, the mechanical plug may further include an overhanging shoulder that extends around the entire circumference of the outer face of the mechanical wall. The crimping element may then have a conical-shaped brim that extends underneath the shoulder of the mechanical plug when the crimping element is slid over the neck of the vial. Thus, any upward movement of the crimping element would be further constricted since the brim of the crimping element would then come into contact with the shoulder of the mechanical plug.

A plunger or extension may also be provided on a bottom surface of the mechanical plug so that, when the mechanical plug is inserted into the neck of the vial, the plunger may extend into a liquid content of the vial in order to raise the surface level of the liquid. Thus, the plunger may substantially reduce the residual air bubbles which may otherwise remain between the surface of the liquid and the inner surface of the mechanical plug.

Yet another exemplary embodiment of a mechanical plug effectively seals the opening of the rear vial section of a vial-dispenser mechanism which incorporates an inner pouch within the rear vial section for minimizing the presence of air inside the rear vial section. A rear portion of the inner pouch has an inverted U shape, and the rear portion radially clasps the opening area of the rear vial section. A radial protrusion of the inner pouch is seated in a complementary recess formed in the opening area of rear vial section, and the rear plug, which also has an inverted U shape, slides over, and radially clasps, the rear portion of the inner pouch and the opening area of the rear vial section to provide a tight seal along both the radial and vertical directions.

Still another exemplary embodiment of a mechanical plug has an annular protrusion which is snap-fitted into a complementary annular recess formed in the opening area of the rear vial section, thereby providing a radial seal along the annular recess. The mechanical plug also has an annular flange which rests against an annular flange of the opening area of the rear vial section. The annular protrusion of the mechanical plug and the annular flange of the opening area act in concert to provide vertical compression of the opening area of the rear vial section.

The pump-type dispenser system according to the present invention for dispensing nasal medicament has several distinct advantages. First, the dispenser system according to the present invention substantially eliminates ingress of air into the pump mechanism, thereby providing not only a sterile environment for the nasal medicament, but also facilitating consistency of the dispensed dosage by minimizing disruption of pump operation caused by air. Second, because the pump-type dispenser according to the present invention is substantially airless, the operation of the pump, as well as the dispensed dosage, is completely unaffected by the orientation of the pump-type dispenser during use. Third, the present invention provides a one-way valve in the nozzle area to further ensure a sterile environment for the nasal medicament inside the dispenser. The valve facilitates only one-way movement of medicament from the interior of the nozzle to the exterior, thereby substantially eliminating the possibility that medicament which has been exposed to ambient air or the exterior of the nozzle may be "sucked back" into the interior of the nozzle, and, in turn, substantially eliminating the possibility of contamination of the medicament inside the dispenser.

In addition to the above-noted advantages, the pump-type dispenser according to the present invention also provides a mechanism by which aerosol-type discharges of uniform dosage is achieved without any propellant gas such as CFC. This is achieved by utilizing a combination of the above-mentioned airless pump mechanism, a "one-way actuation release mechanism," which facilitate loading and ejection of a uniform dose of medicament with a single actuation motion, and an aerosol-generating nozzle mechanism which achieves a very low "head loss" for the fluid discharge.

BRIEF DESCRIPTION OF THE DRAWINGS

FIG. 29b is a cross-sectional view of the rear plug mechanism for sealing the vial portion of the phial pump shown in FIG. 29a.

FIG. 30b is a cross-sectional view of the rear plug mechanism for sealing the vial portion of the phial pump shown in FIG. 30a.

DETAILED DESCRIPTION OF THE INVENTION

Figure 1:
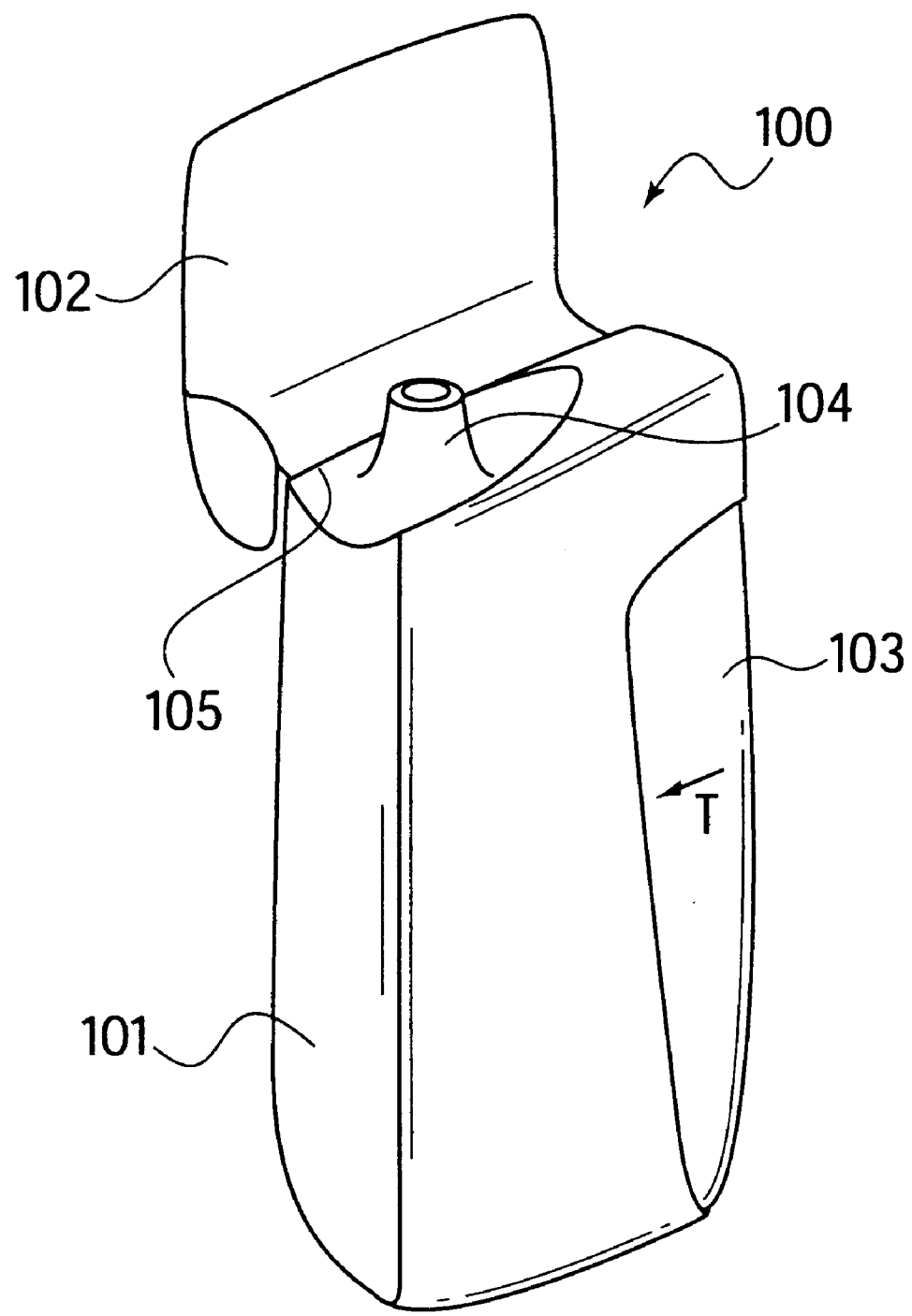
FIG. 1 is a perspective view of an exemplary embodiment of the pump-type dispenser for nasal medicaments in accordance with the present invention.
Figure 2:
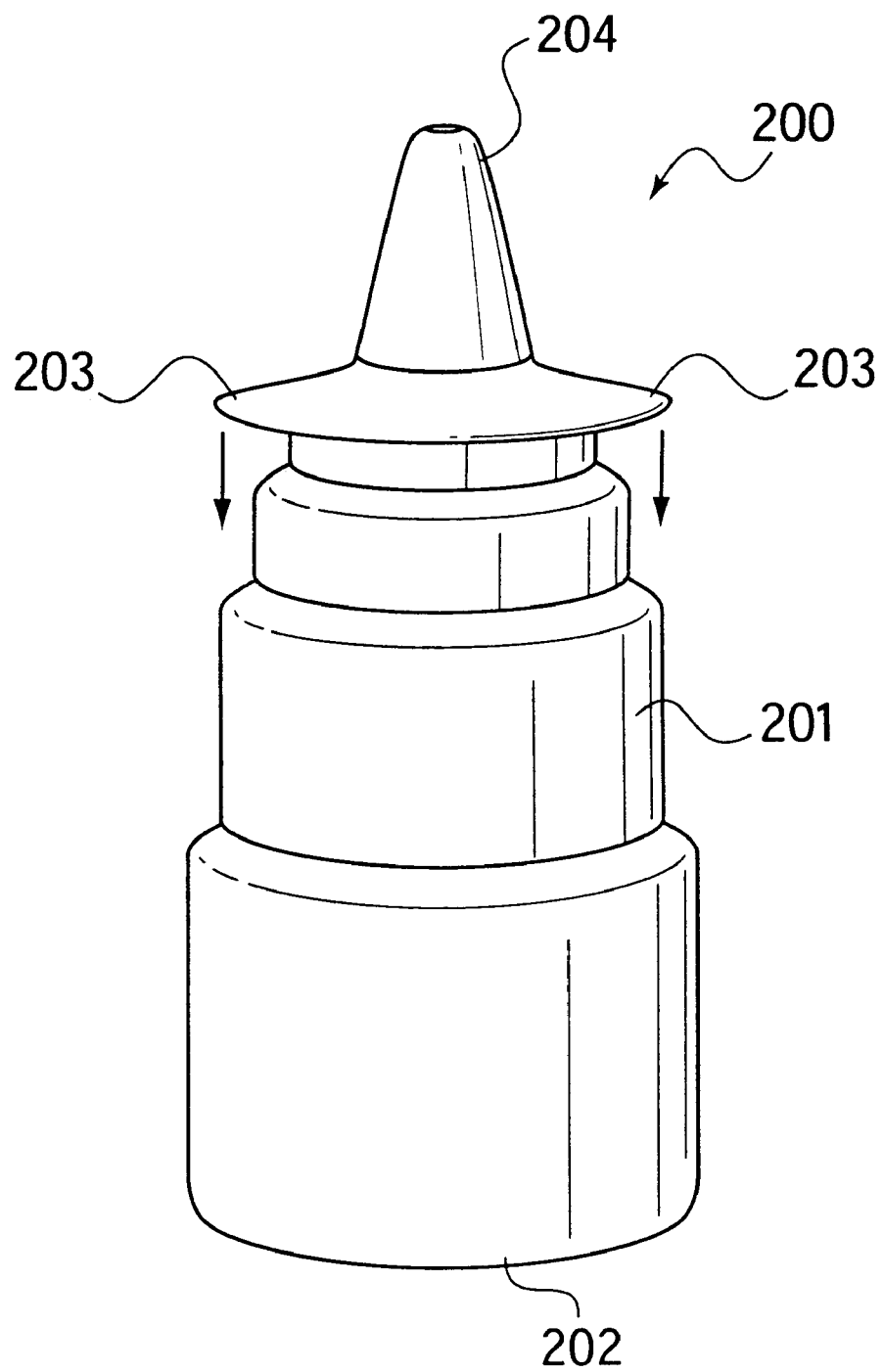
FIG. 2 is a front-elevation view of a prior art pump-type dispenser.

As shown in FIG. 1, an exemplary embodiment of the pump-type dispenser system 100 for dispensing nasal medicaments in accordance with the present invention has an exterior housing 101, an actuation trigger mechanism or button 103 on one side of the housing 101, a screen lid 102 hinged to the top portion of the housing 101 by means of an articulation hinge 105, and a nozzle housing portion 104. The screen lid 102 serves three primary functions. First, the lid serves as a guide for aligning the axis of the nozzle housing portion 104 with the axis of the nasal passage: by simply placing the interior surface of the lid 102 against the nasal ridge, the user is able to easily center the nozzle housing portion 104 within the nasal passage. Second, the lid 102 serves as a screen for hiding the nasal area from the public view, thereby enabling the user to apply the nasal medicament in a discrete manner. Third, when the lid 102 is folded down, it serves as a cover which isolates the nozzle housing portion 104 from the germs and other pollutants which may surround the nozzle housing portion 104. Furthermore, because the lid is not detachable from the exterior housing, this arrangement eliminates the possibility of misplacing the lid and risking contamination of the nozzle housing portion. In this manner, the lid 102 provides an excellent hygienic protection for the nozzle housing portion 104.

In the exemplary embodiment shown in FIG. 1, the actuation trigger button 103 is connected to a one-way actuation mechanism within the housing 101, and the one-way actuation mechanism is in turn connected to a pump mechanism. The one-way actuation mechanism and the pump mechanism are explained in further detail below. By depressing the actuation trigger button 103 transverse to the axis of the nozzle housing portion 104, the pump mechanism is operated in such a manner that the pump mechanism sequentially loads and dispenses a precalibrated amount of nasal medicament, all within a single continuous motion of the trigger mechanism. Because the one-way actuation mechanism accomplishes loading and dispensation of medicament in a single continuous motion of the trigger mechanism, there is no possibility of locking the pump mechanism in a compressed state, which would lead to "creeping," or permanent deformation, of the pump mechanism. Because the actuation trigger button 103 is operated transverse to the axis of the nozzle housing portion 104, there is substantially no risk of accidentally removing the nozzle housing portion 104 from the nasal area during operation of the pump-type dispenser 100 according to the present invention.

An exemplary pump mechanism which may be incorporated in the pump-type dispenser system according to the present invention is a three-piece phial-pump. The exemplary phial-pump, which will be explained further in connection with FIGS. 3–6E, is designed to eliminate the presence of air or the need for preservatives in the retained formulation and still prevent the contamination of this formulation. In addition, this type of exemplary phial-pump should be able to benefit from almost zero exposure to the air whilst the phial is being filled with the formulation, thus ensuring the sterility of the content without requiring preservatives.

Figure 3:
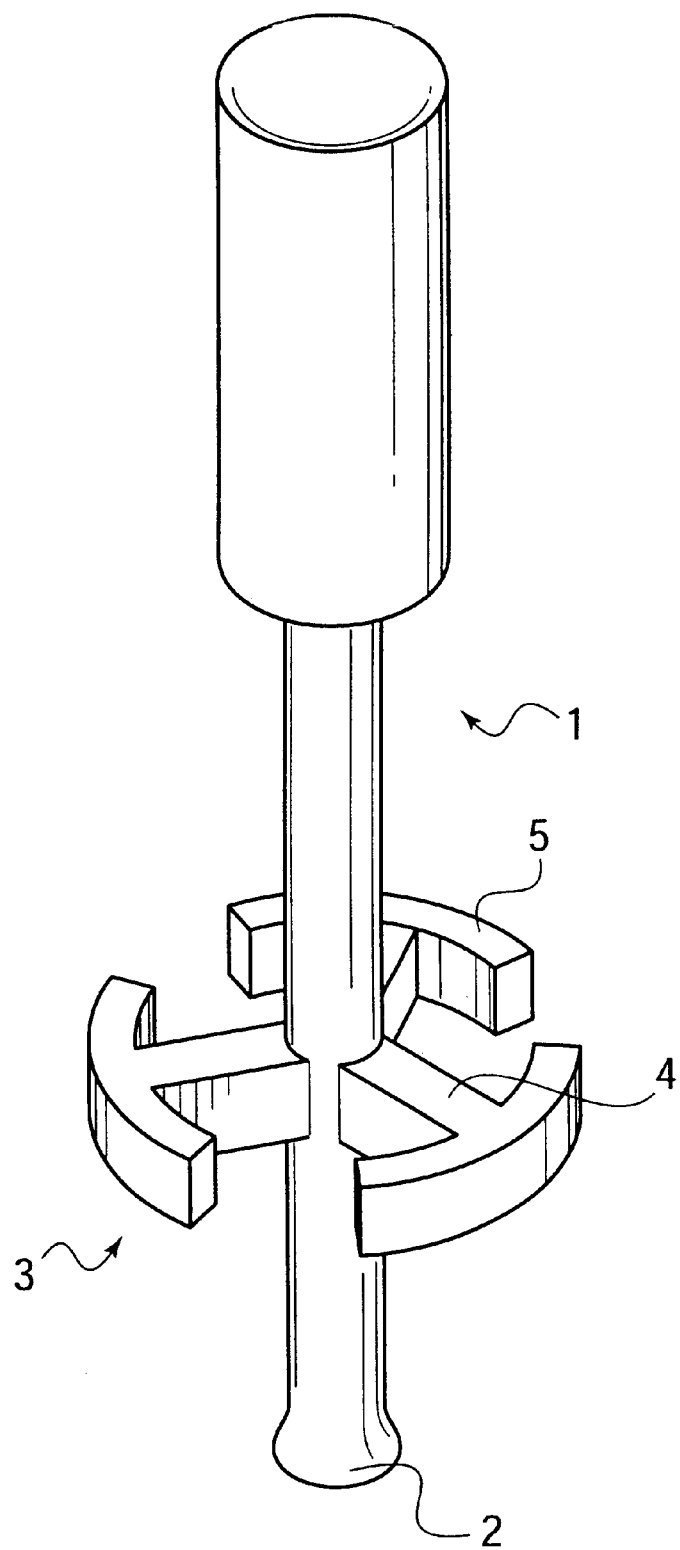
FIG. 3 is a perspective view of an embodiment of a piston to be incorporated as a part of an embodiment of the pump-type dispenser for nasal medicaments according to the present invention.

As shown in FIG. 3, the exemplary phial-pump has a piston which features: a large longitudinal plunger 1, at the front end of which is a flange 2 designed to ensure the seal of the cavity of the pump body when the piston increases the pressure therein; and ship's-anchor-shaped fins 3, of which there are three in this configuration. Each of the fins 3 has a spoke 4 at the end of which is an arc 5.

Figure 4:
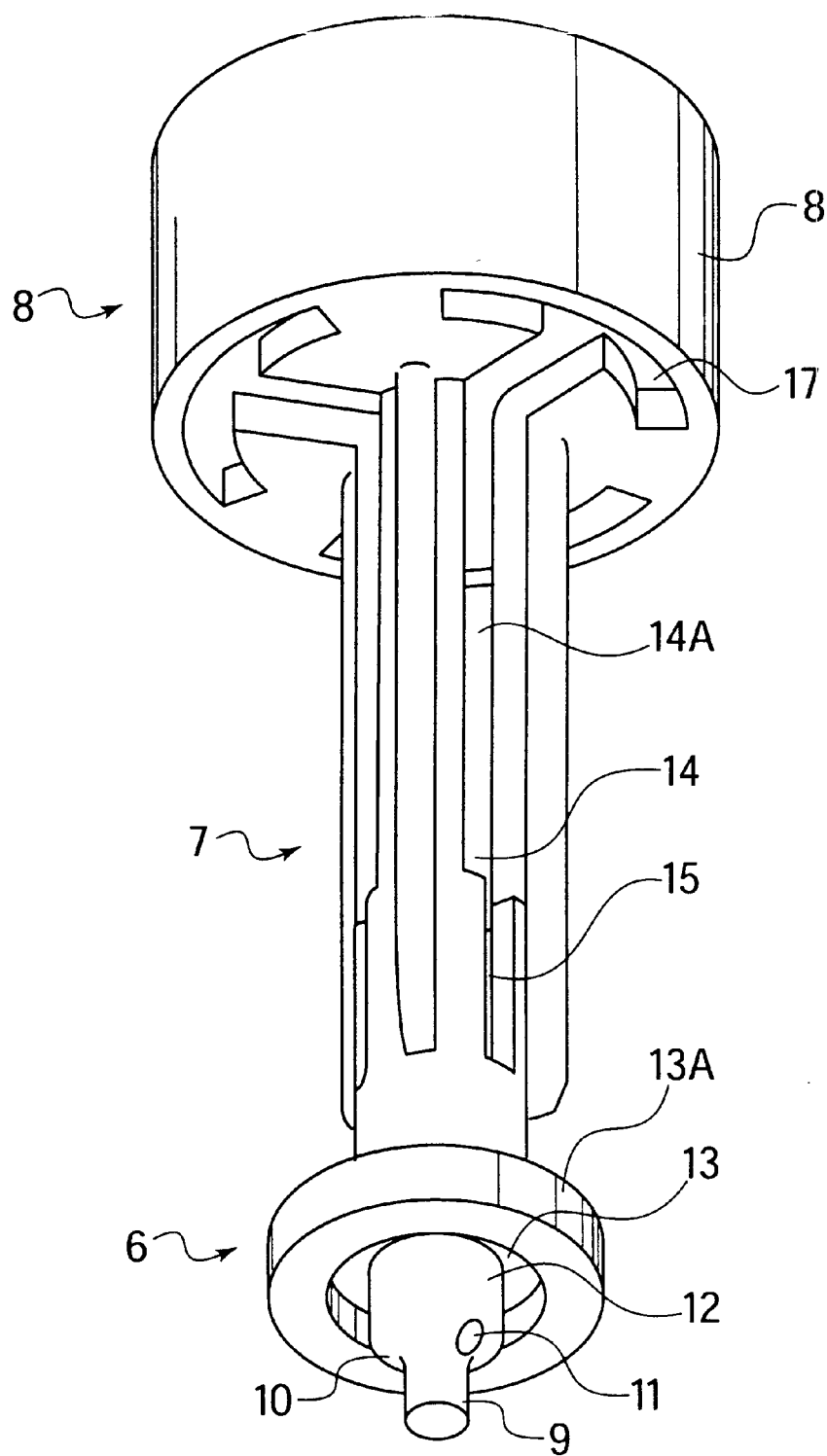
FIG. 4 is a perspective view of an embodiment of a pump body to be incorporated as a part of an embodiment of the pump-type dispenser for nasal medicaments according to the present invention, which pump body is intended to cooperate with the piston illustrated in FIG. 3.

As shown in FIG. 4, the exemplary phial-pump has a pump body made up of three main parts: the front part, or "nose" 6; the middle part, or "sleeve" 7; and the rear part, or "body" 8 of the pump. Nose 6 may have a purely cylindrical or truncated-cone configuration; here, it comprises a small cylinder 9 at the tip followed by a truncated-cone area 10, itself perforate by the evacuation orifice 11 of the pump. Behind the truncated-cone part is another cylindrical part 12 and, behind this cylindrical part 12, an annular groove 13 serving to seal an elastic envelope which will be described in further detail below; this annular groove separates the nose proper from a disc or "frontal disc" 13a.

As shown in FIG. 4, sleeve 7 is a cylindrical sleeve, inside of which is the pump cavity. The cylindrical wall of sleeve 7 is perforated by longitudinal slots 14, in each of which slides a corresponding piston spoke 4. Each slot has two portions: a wider rear portion 14 for the piston spokes 14 to slide along; and a narrower front portion constituting the communication orifice between the external liquid and the pump cavity, and forming an inlet orifice 15. The height of this pump cavity determines the level at which the piston will effect compression upon the fluid, and the height therefore determines the volume of the dose to be ejected.

Figure 5:
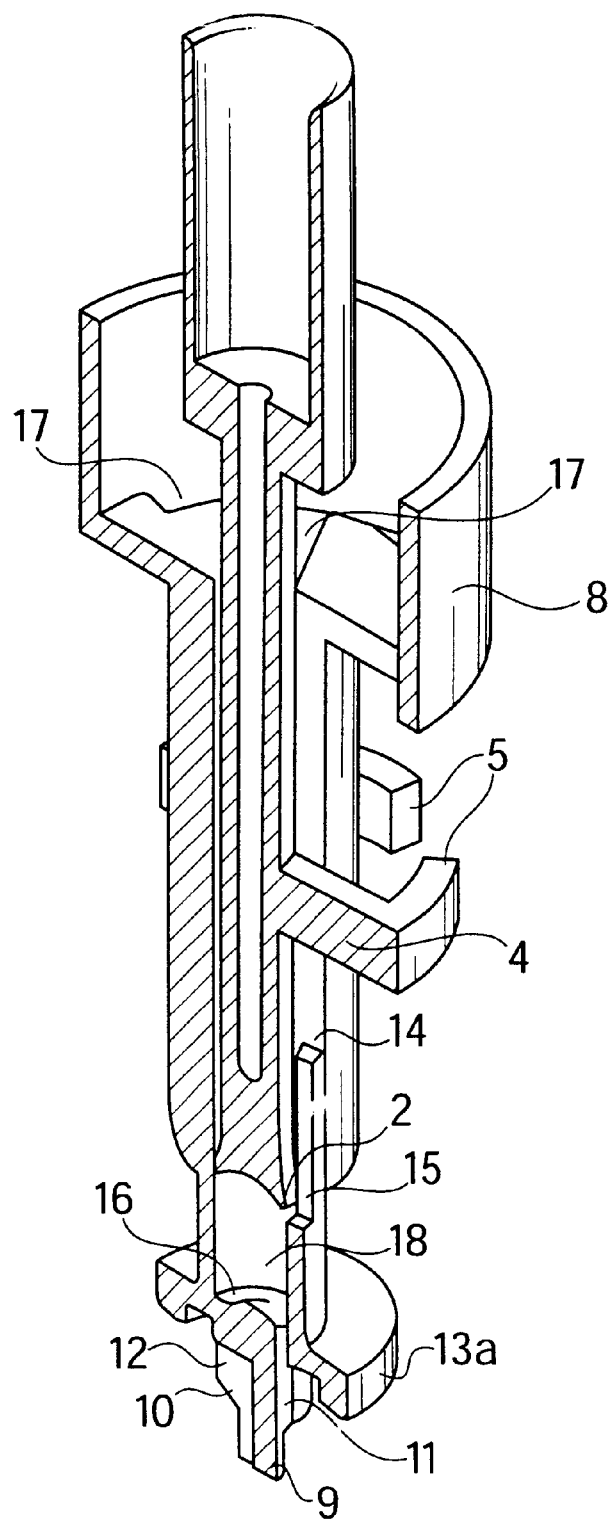
FIG. 5 is a lateral cross-sectional view of the piston shown in FIG. 3 fitted into the pump body shown in FIG. 4.

On the inner wall of this sleeve, in its frontmost part following the pump nose, is stop 16 comprising an annular undercut, shown in FIG. 5, which houses the annular flange of the piston when the pump is in the at-rest or closed position. This undercut 16 enables the front annular flange 2 of the piston to exert a very slight compression after initial assembly, so as to keep the rest of the pump in perfect occlusion without causing the front flange of the piston to creep whilst storing the pump prior to its use. It is thus impossible for the air or liquid contained in the evacuation orifice 11 of the nose, here an ejection channel, to come into contact with the liquid contained in the rest of the pump or phial.

Continuing with FIG. 4, the pump body 8 comprises a cylindrical cavity in continuity with the sleeve, and of a decidedly larger diameter, and will itself be housed in the rear ring of the envelope in order to activate the pump. In the front part of this element there are cutaway sections 17 enabling fins 3 to pass through so as to fit the piston into the pump body. In the example illustrated here, the pump body is movable whereas the piston will be held in a stationary position.

As shown in FIG. 5, the piston of FIG. 3 is fitted inside the pump body of FIG. 4. In addition to the elements described previously, the front stop 16 of the piston with its undercut is shown. Also shown is the inlet orifice 15, and the position of the piston inside the body is such that if the piston moves forward, it will block off, in a cavity (or "pump duct") 18, the preset volume of fluid admitted through orifice 15. Also shown is the spoke 4, installed in a longitudinal slot in which it is adapted to slide. In addition, on the rear side of the pump body, a cutaway section 17 enables a fin to pass through. It can be seen from above that the pump mechanism according to the present invention has three annular parts 12, 5 and 8.

Figure 6:
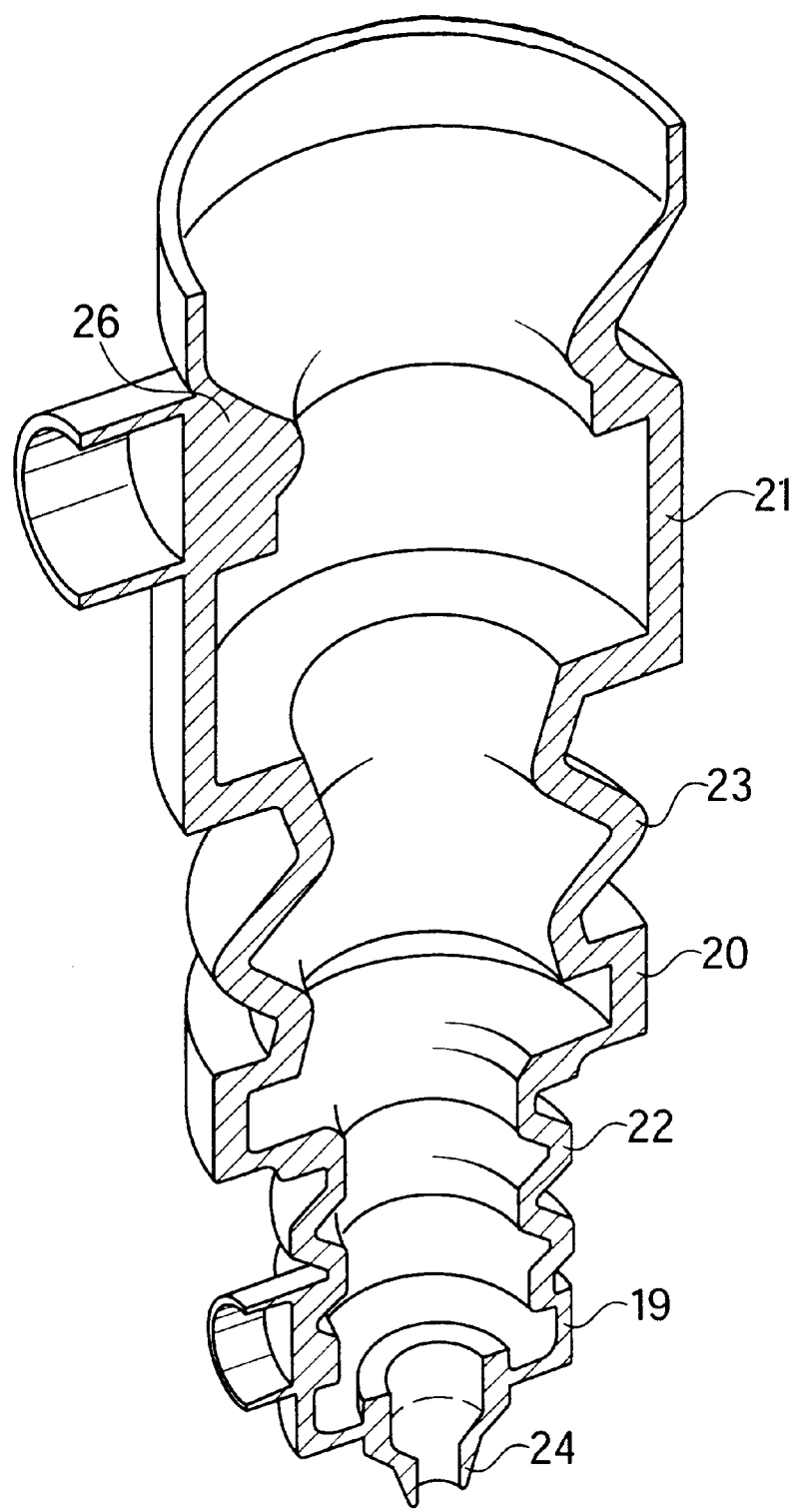
FIG. 6 is a lateral cross-sectional view of an embodiment of an envelope intended to cooperate with the piston shown in FIG. 3 and the pump body shown in FIG. 4 to form an embodiment of a phial-pump incorporated in the pump-type dispenser for nasal medicaments according to the present invention.

As shown in FIG. 6, the exemplary elastic envelope has three rings: a front ring 19, a middle ring 20 and a rear ring 21, amongst which are confined a front concertina 22 and a rear concertina 23. The front ring 19 cooperates with the ring 13a of the pump body, the middle ring 20 cooperates with the incomplete ring formed by the arcs 5 on the piston, and the rear ring 21 cooperates with the rear ring 8 of the pump body. These rings of the elastic envelope securely retain the rings of the other two pieces, i.e., the pump body and the piston; in particular, the assembly at the level of rings 13a and 19 is perfectly hermetic. Moreover, at the frontmost level of the envelope is an elastic membrane 24 forming a one-way valve towards the outlet which is defined by at least the elastic membrane and the complementary parts of the small cylinder 9 of the truncated-cone area 10.

It will also be seen from FIG. 6 that, in this exemplary configuration, the envelope comprises two parts which have been designed to enable the passage of hollow needles in an alternative method of filling the phial-pump with a fluid, liquid or gel, i.e., areas 25 and 26. These parts have a greater thickness than that of the surrounding areas, and filling needles penetrate these areas if the rear vial or phial section of the phial-pump doesn't have a filling opening and doesn't employ a mechanical closure element. Moreover, these areas each comprise a small cylinder capable for example of being heat-sealed under pressure between two heated jaws. Such a cylindrical device may be replaced for example by an extra thickness raised towards the outside of the envelope, thus protruding onto the outer wall, and onto which a heated piece may be applied so as to melt this raised part in order totally to seal the orifice having enabled the penetration of a needle. Lastly, it will be noted that in FIG. 6, the rear part of the envelope serving solely as a receptacle has not been shown here.

The above-described components of the exemplary phial-pump is assembled as follows. First, the piston is fitted into the pump body until the front annular flange reaches the stop, and the partially assembled "pump" is thus in the at-rest closed position. The partially assembled "pump" is then fitted into the elastic envelope whilst jets of compressed gas dilate the elastic envelope during assembly enabling the latter with a minimum of friction.

Figure 7:
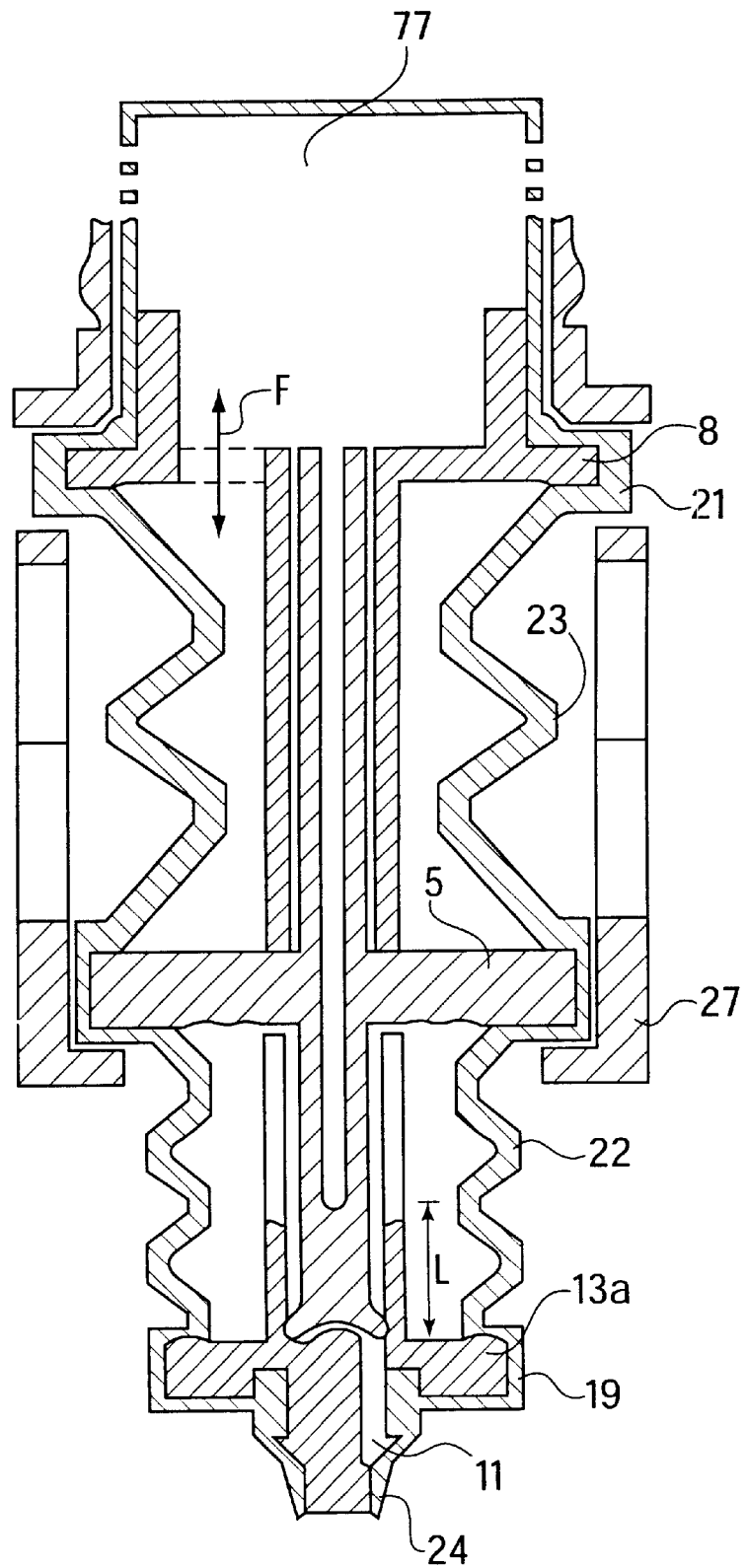
FIG. 7 is a cross-sectional view of an assembled phial-pump incorporating the piston, the pump body and the envelope shown in FIGS. 3, 4 and 6, respectively.
Figure 8:
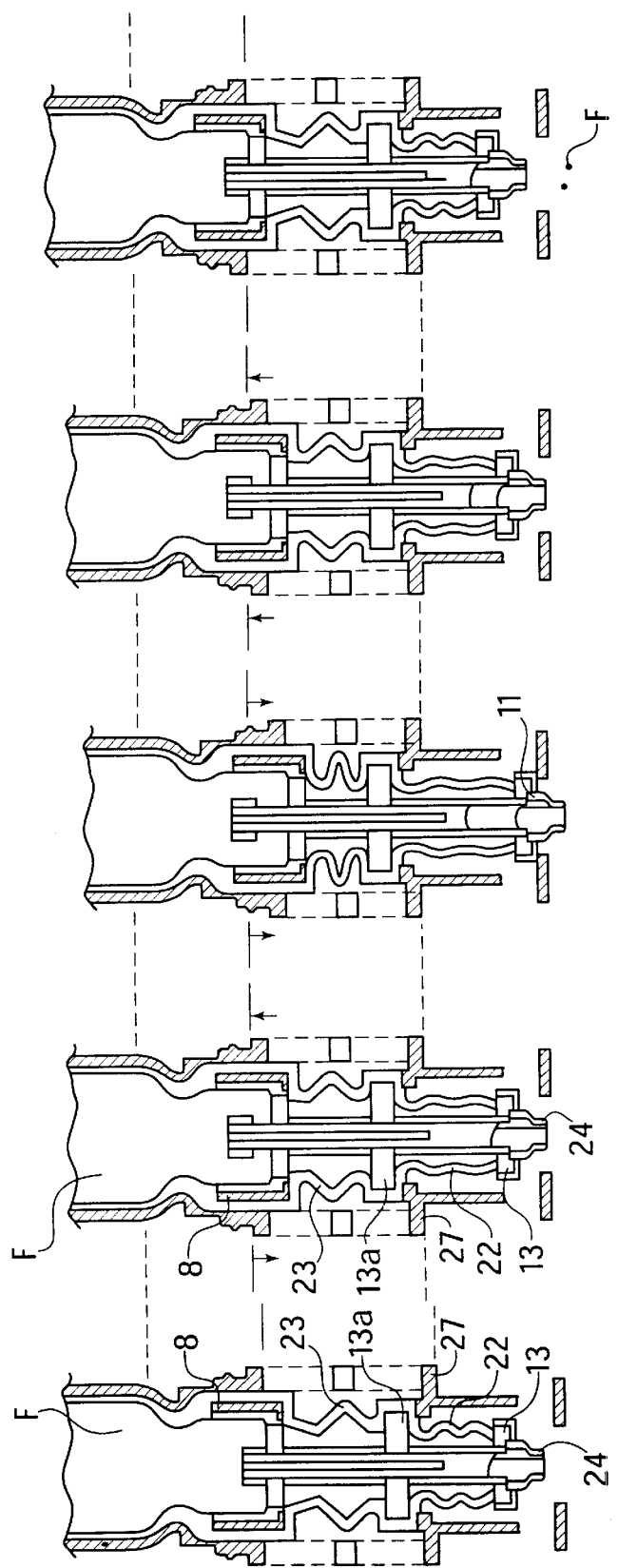
FIGS. 8A–8E show a sequence of cross-sectional views of the phial pump shown in FIG. 7, the sequence illustrating the operation of the phial-pump.

As shown in FIG. 7, an alternative embodiment of the phial-pump incorporates three pieces similar to the above pieces, but with a few minor differences. The embodiment of FIG. 7 incorporates the rings 13a, 5 and 8 respectively in the rings of the envelope numbered 19, 20 and 21. Also shown are the front 22 and rear 23 concertina springs. As can be seen from comparing FIGS. 5 and 7, length L corresponds to the backward travel of the piston inside the body enabling on the one hand the introduction of fluid into duct 18 of the pump and on the other determining, on the basis of the inside diameter of duct 18, the volume of fluid to be expelled. Furthermore, as shown in FIG. 7, fluid from a vial portion 77 is in communication (as indicated by the bidirectional arrow "F") with a bellows chamber contained within the bellows portion 23.

FIG. 7 also shows the phial-pump fitted inside a rigid shell 27. Also more clearly distinguishable is the annular under-cut. In the cases illustrated above, for projecting each individual dose of an ophthalmic liquid, the dimensions may be, for example, as follows: a) diameter of the channel constituting the outlet orifice, and its length—approximately 1.0 mm and 2.0 mm, respectively; b) thickness of the Kraton™ envelope at the level of valve 24 is approximately 0.8 mm, decreasing towards the fluid outlet end; and c) thickness of the Kraton envelope at the level of concertina 23 is 1 mm, and at concertina 22, 0.75 mm. Lastly, we can see that the rear part of the envelope, at the top of FIG. 7, has been enclosed for example by sealing, so that the pump body and piston are totally enveloped with the exception of the front end of the pump body.

It should be noted that two different types of phial-pump systems may be implemented in accordance with the present invention: a) a relative arrangement of the housing and the phial-pump vial which allows the rear part of the vial to be movable; or b) a relative arrangement in which the rear part of the phial-pump vial is fixed relative to the housing, and only the piston is movable. It should be noted that a given phial-pump may be incorporated as a part of either one of the above-described relative arrangements. Illustrated in connection with FIGS. 8A–8E are various steps involved in the operation of the first type of phial-pump system described above. In this series of FIGS. 8A–8E, the phial-pump has been assembled as shown in FIG. 7, inside a rigid shell. In the phial-pump described here, by using this rigid shell, the pump body is movable whilst the piston is held in a stationary position.

In FIGS. 8A–8E, "F" represents the fluid with which the elastic envelope has been filled. In the at-rest position shown in FIG. 8A, the piston is held in a stationary position by receptacle 27 of the pump, i.e., by a different structure to the three elements of the actual phial-pump. In the phial-pump system described here, the piston rings are held secure by the compression of rear concertina spring 23. In FIG. 8B, on activating the pump, the pump body is thrust forwards by its rear part 8 and transmits this thrust to the nose which is made integral with it by means of the sleeve. The effect of this is to create a cavity of drops in pump duct 18 in this space, which remained virtual during the pump's at-rest period and which is then of a volume determined by the height of the bottom lip of front groove 14 from sleeve 7, which places this cavity of drops 18 in communication with the cavity limited by the front concertina. This cavity of drops 18 is limited at the front by pump stop 16, at the sides by the front cylindrical par 18 of the sleeve not opened by the lateral slots 14 and, a the rear, by the front part 2 of the piston limited by front annular flange 2 of this piston.

Continuing with FIG. 8C, when the nose is pushed sufficiently far forward so that front flange 2 of the piston is then behind the front lips 15 of the front grooves of sleeve 7, the depression in the cavity of drops 18 is then made up for by the arrival of fluid F. The pump is then said to be in the filled or open position. This filled position may be locked by a ratchet system on receptacle 27 which itself will be unlocked if the user applies pressure to a pawl. The pawl may form a part of the receptacle case 27 in which this pump is housed. The locking/unlocking mechanism and operation will be explained in detail in a separate section below. During activation, rear spring concertina 23 is under compression and front concertina 22 is extended. Subsequently, as shown in FIG. 8D, during the stage of ejecting the drops of fluid F, i.e. when the nose and body return to their initial at rest position, rear spring concertina 23, initially compressed, extends and the assembly resumes the at-rest position shown in FIG. 8E.

Figure 29A:
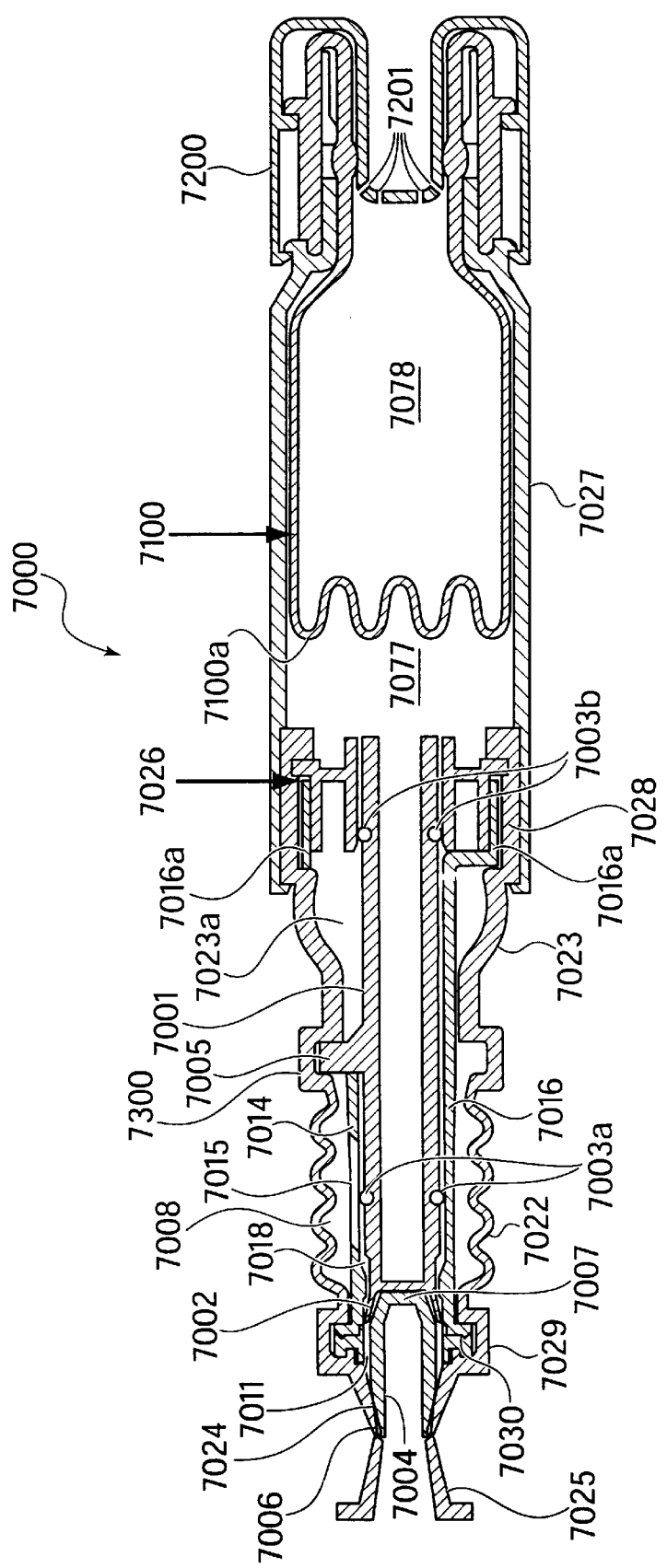
FIG. 29a is a cross-sectional view taken along the longitudinal axis of another exemplary embodiment of a phial pump in accordance with the present invention.

Illustrated in FIG. 29a is another exemplary embodiment of a type of phial pump in which the piston portion is movable and the rear part of the vial is fixed relative to the housing. The operation of the pump 7000 shown in FIG. 29a is similar to that of the phial pump illustrated in FIGS. 3–7 and 8a–8e, but several mechanical features distinguish the pump 7000. The pump 700 includes a main piston 7001 which is slidably engaged within a sleeve formed by a collet 7026 and longitudinally-extending portions 7014 and 7016. The piston 7001 is coupled via a radially-extending flange 7005 to an elastic envelope 7300 having a front concertina portion 7022, a rear bellows portion 7023, a rear portion 7028, a front ring 7029, an exterior nozzle portion 7006 and a front cone 7025. The front concertina portion 7022 and the rear bellows portion 7023 provide spring action to the coupled piston 7001. The rear portion 7028 of the elastic envelope 7300 securely retains the collet 7026 and the rear segment 7016a of the longitudinally-extending portion 7016, and in turn, rear portion 7028 is securely retained within the front segment of a vial portion 7027, inside of which defines a fluid reservoir 7077. The vial portion is made of a rigid material which substantially eliminates ingress of air into the fluid reservoir 7077.

Continuing with the exemplary embodiment of the pump shown in FIG. 29a, a fluid-outlet valve 7024 is defined by the interface of the exterior nozzle portion 7006 and a rigid interior nozzle portion 7004 which is secured via a radial protrusion 7030 to a complementary ring portion 7029 of the elastic envelope 7300. The exterior nozzle portion 7006 has a radial thickness that decreases along the longitudinal axis from the base of the nozzle portion to the tip. When the pump 7000 is at its ambient position, the piston 7001 rests against a base segment 7007 of the rigid interior nozzle portion 7004. During operation of the pump 7000, a cavity (or "pump duct") 7018 is defined between the base segment 7007 and a front end of the piston 7001 when the piston is initially withdrawn relative to the base segment 7007. Furthermore, an outlet orifice 7011 provides a fluid communication channel between the cavity 7018 and the fluid-outlet valve 7024.

The longitudinally-extending sleeve portion 7014 shown in FIG. 29a has an elongated slot 7015 which serves as the inlet orifice to the cavity 7018 and which is substantially similar to the slot 15 shown in FIG. 5. Furthermore, two O-shaped rings 7003a and 7003b are secured, or molded, around the circumference of the piston 7001 as shown in FIG. 29a, such that the O-shaped rings provide a fluid-tight seal between the piston 7001 and the surrounding sleeve formed by the collet 7026 and longitudinally-extending portions 7014 and 7016. The O-shaped rings 7003a and 7003b may be made of silicone, polyisoprene, Kraton™ or any rubber-like material. In addition, the base segment 7007 delimits the forward compressive movement of the piston 7001 and its front flange 7002 which ensures the seal of the cavity 7018 during the compressive movement.

Operation of the pump 7000 may be substantially similar to the operation illustrated in FIGS. 8a–8e. From the ambient position of the piston 7001 depicted in FIG. 29a, the relative movement of the piston away from the base segment 7007 of the rigid interior nozzle portion 7004 creates a suction, or depression, within the cavity 7018 defined by the space between the base segment 7007 and the front end of the piston 7001. The maximum relative movement of the piston 7001 away from the base segment 7007 is predefined. When the flange 7002 of the piston 7001 is positioned behind the slot 7015, a fluid communication channel is established through the slot 7015, and the depression in the cavity 7018 draws in the fluid to the cavity from a surrounding cavity 7008 defined between the front concertina portion 7022 and the front sleeve portion 7014. During this "filling" stage in which the pump piston 7001 is moved rearward relative to the base segment 7007, the front concertina 7022 is extended and the rear bellows portion 7023 is compressed.

During the fluid-ejection stage, the piston 7001 urged forward by the spring action of the front concertina 7022 and the rear bellows portion 7023. When the front flange 7002 has moved forward of the elongated slot 70015, the fluid in the cavity 7018 is compressed by the forward movement of the piston 7001, and the compressed fluid is channeled through the outlet orifice 7011 to the fluid-outlet valve 7024. When sufficient fluid pressure exists at the fluid-outlet valve 7024, the exterior nozzle portion 7006 is radially deformed and separated from the rigid interior nozzle portion 7004 to pass the fluid. Because the exterior nozzle portion 7006 has a radial thickness that decreases along the longitudinal axis from the rear or the base of the nozzle portion to the front or the tip, the front segment of the fluid-outlet valve 7024 is closed when the base segment of the valve is initially opened, and as the fluid passes through the valve 7024, the base segment of the valve is closed by the time the front segment of the valve 7024 is opened to emit the fluid. At the completion of the fluid-ejection stage, the piston 7001, the front concertina 7022 and the rear bellows 7023 return to the ambient position shown in FIG. 29a.

In the above-described pump 7000, the two O-shaped rings 7003a and 7003b provide a fluid-tight seal between the piston 7001 and the surrounding sleeve formed by the collet 7026 and longitudinally-extending portions 7014 and 7016, thereby maintaining the bellows chamber 7023a free of fluid. The absence of fluid in the bellows chamber substantially eliminates the possibility of fluid hindering the elastic deformation of the rear bellows portion 7023.

As previously noted above, the interior of the vial portion 7027 defines the fluid reservoir 7077. The interior of the vial portion 7027 also contains, however, an inner pouch 7100 made of an elastic material, e.g., Kraton™. As shown in FIG. 29a, the inner pouch 7100 is secured to the vial portion 7027 by means of a rear plug 7200, which will be described in further detail below. The interior 7078 of the inner pouch 7100 contains varying volume of air, depending on the amount of liquid contained in the fluid reservoir 7077. FIG. 29a depicts the fluid reservoir 7077 containing an amount of fluid which is about a third of the reservoir's maximum capacity. The elastic inner pouch 7100 is collapsible, or expandable, such that the exterior surface 7100a of the inner pouch conforms to the liquid level in the fluid reservoir 7077, i.e., when the vial portion 7027 is completely filled with fluid, the inner pouch is substantially completely collapsed and the volume of the interior 7078 is substantially zero.

As the liquid in the reservoir 7077 is gradually depleted as the result of the pump operation, the pouch 7100 expands correspondingly, drawn by the suction pressure in the reservoir 7077, thereby substantially eliminating the residual air inside the reservoir 7077, which residual air may adversely affect the operation of the pump. The volume of air in the interior 7078 is in turn regulated via air holes 7201 formed in the rear plug. In the above manner, the inner pouch functions as an effective air-regulation mechanism for the fluid reservoir 7077.

Figure 29B:
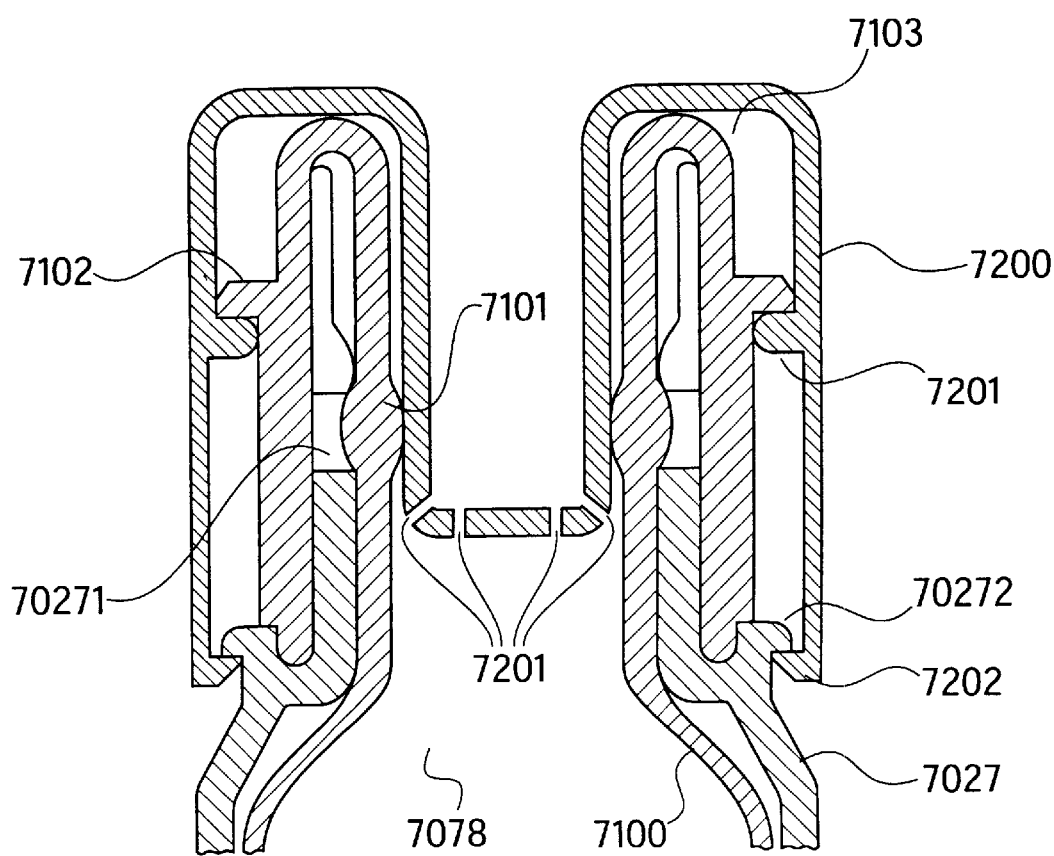

As shown in detail in FIG. 29b, the rear of the vial portion 7027 of the phial pump 7000 shown in FIG. 29a is sealed by means of the rear plug 7200. Furthermore, the inner pouch 7100 is secured to the vial portion 7027 by the rear plug 7200. As previously noted, the rear plug 7200 has a plurality of air holes 7201 which regulate the volume of air in the interior 7078 of the inner pouch 7100. A rear portion 7103 of the inner pouch 7100 has an inverted U shape, and the rear portion 7103 radially clasps the rear of the vial portion 7207. A radial protrusion 7101 of the inner pouch 7100 is seated in a complementary recess 70271 formed in the rear of the vial portion 7207. In addition, the rear plug 7200, which also has an inverted U shape, radially clasps the rear portion 7103 of the inner pouch 7100.

The rear plug 7200 has two notch portions 7201 and 7202 which protrude radially inward, and the notch portions 7201 and 7202 interact with a notch portion 7102 of the rear portion 7103 of the inner pouch and a notch portion 70272 of the rear of the vial portion 7207, respectively. When the rear plug is being placed into the sealing position, one interior surface of the rear plug compressively engages the radial protrusion 7101 of the rear portion 7103 of the inner pouch 7100, and the notch portions 7201 and 7202 of the rear plug slide over the notch portions 7102 and 70272, respectively, to firmly engage the underside of the notch portions 7102 and 70272. For this reason, the rear plug is also referred to as a "sliding plug." In this manner, the rear plug 7200 provides compression along both the radial and vertical directions to the rear portion 7103 of the inner pouch 7100 and the rear of the vial portion 7207 to provide a tight seal of the rear of the vial portion 7207 along both the radial and vertical directions.

Figure 30B:
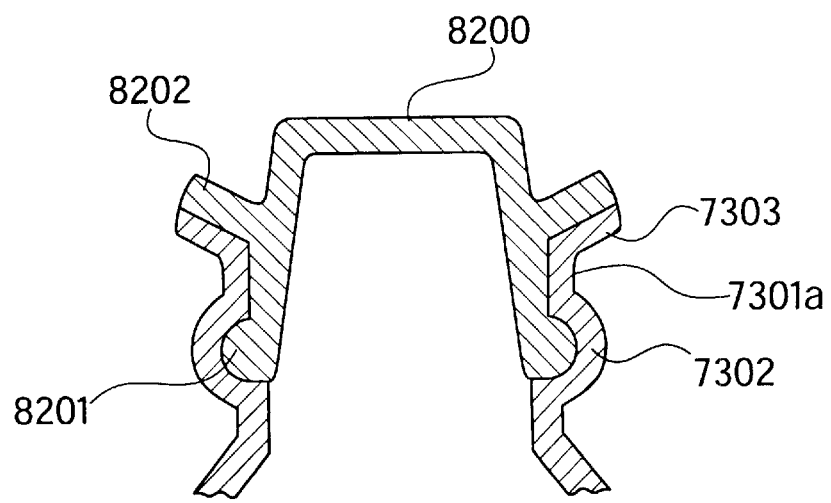
Figure 30A:
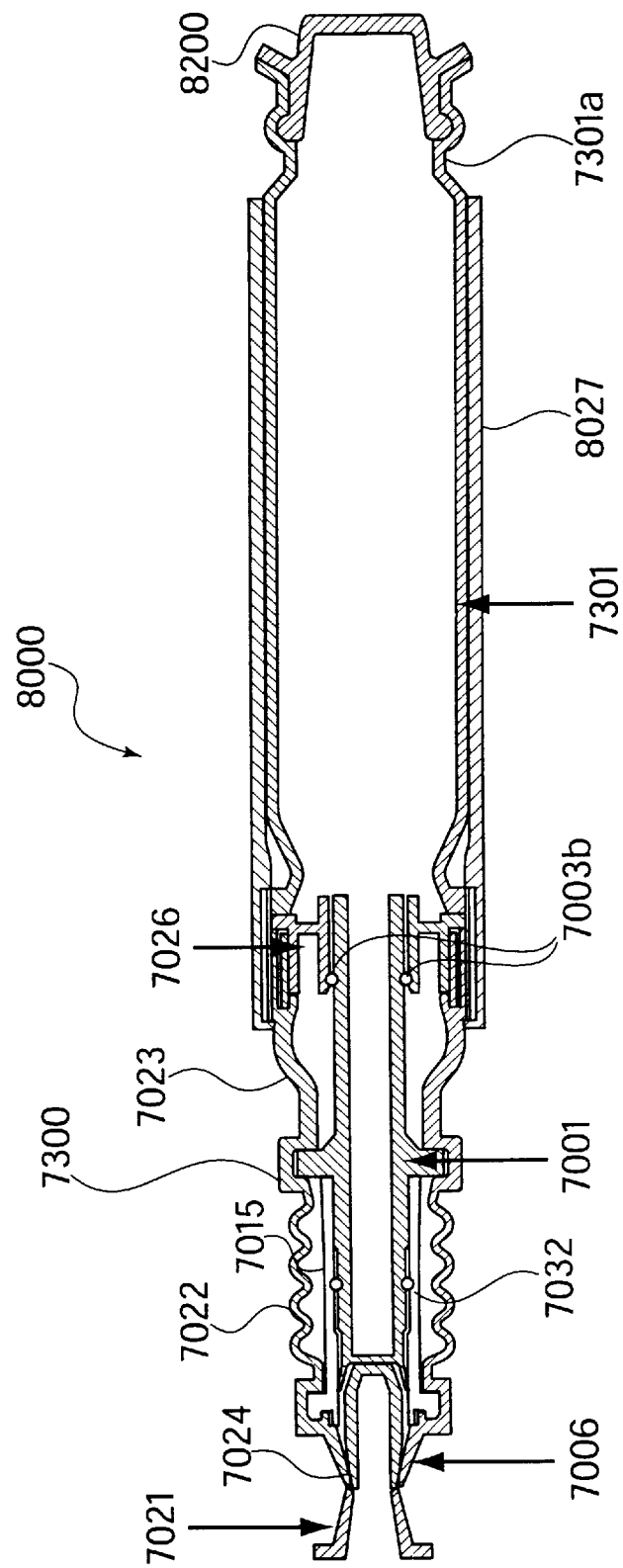
FIG. 30a is a cross-sectional view taken along the longitudinal axis of yet another exemplary embodiment of a phial pump in accordance with the present invention.

Illustrated in FIG. 30a is yet another exemplary embodiment of a type of phial pump in which the piston portion is movable and the rear part of the vial is fixed relative to the housing. The pump 8000 illustrated in FIG. 30a is substantially similar to the pump illustrated in FIG. 29a, except for a couple of differences. First, the pump 8000 does not have an inner pouch 7100. Instead, the elastic envelope portion 7300, which include the front concertina portion 7022 and the rear bellows portion 7023, extends into the rear to form a vial portion 7301. The vial portion 7301 is substantially enclosed within a rigid exterior housing 8027. Second, the rear plug 8200 incorporated in the exemplary embodiment of FIG. 30a is simpler than the rear plug 7200 incorporated in the pump 7000 shown in FIG. 29a.

As shown in further detail in FIG. 30b, the rear plug 8200 cooperates with the rear segment 7301a of the vial portion 7301 to provide a tight seal. The rear plug 8200 has an annular protrusion 8201 which is snap-fitted into a complementary annular recess 7302 formed in the rear segment 7301a of the vial portion 7301, thereby providing a radial seal along the annular recess 7302. The rear plug 8200 also has an annular flange 8202 which rests against an annular flange 7302 of the rear segment 7301a of the vial portion 7301. The annular protrusion 8201 and the annular flange 8202 act in concert to provide vertical compression of the rear segment 7301a. In this manner, the rear plug 8200 provides a tight seal of the rear segment 7301a of the vial portion 7301 along both the radial and vertical directions.

Figure 9:
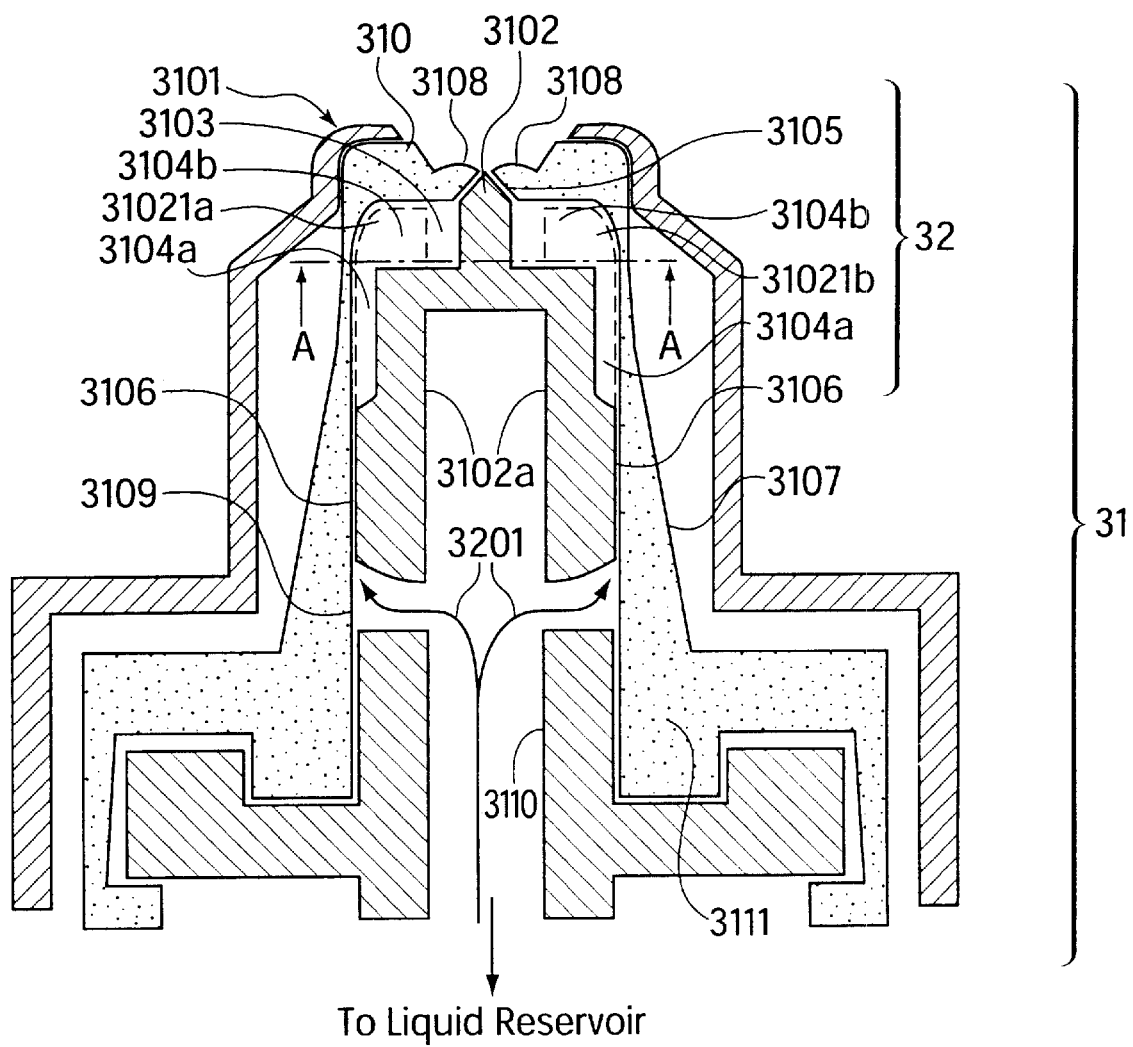
FIG. 9 is a cross-sectional view along the length of aerosol dispenser including one embodiment of a nozzle mechanism according to the present invention.
Figure 11:
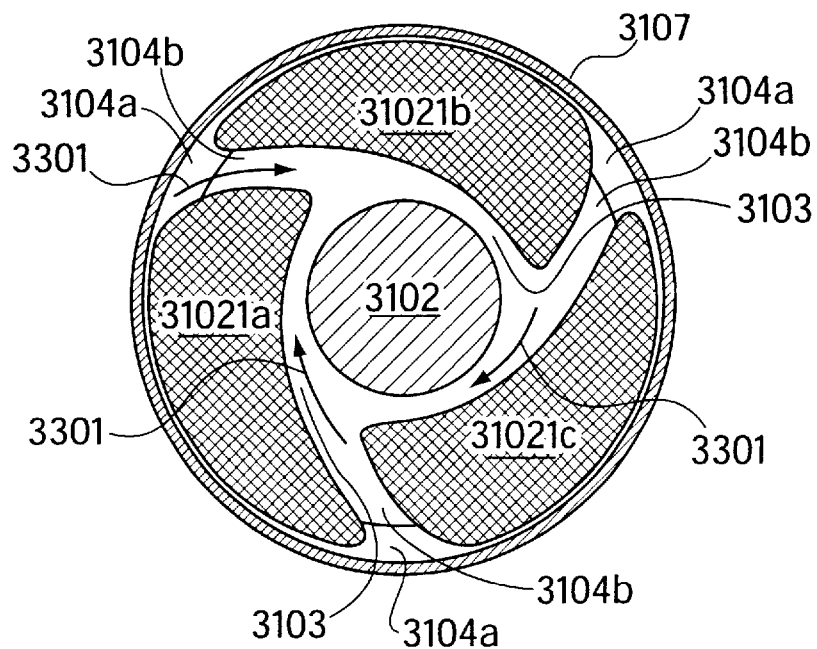
FIG. 11 is a cross-sectional view along line A—A shown in FIG. 9.

Turning to FIGS. 9 and 11, shown in these figures is a first exemplary embodiment of an aerosol tip or nozzle mechanism 32 which may be incorporated in the nasal dispenser system according to the present invention indicated generally by numeral 31. The first exemplary embodiment of the aerosol tip mechanism 32 includes a flexible nozzle portion 310 having an outlet portion 3108 and fluid channels (or feed channels) 3104, a rigid shaft 3102 received within the flexible nozzle portion 310, and a rigid external housing 3101 surrounding the flexible nozzle portion 310 and exposing the outlet portion 3108. The rigid shaft 3102 interfaces the interior of the outlet portion 3108 to form a first normally-closed valve 3105, as well as to define a swirling chamber or collecting chamber 3103 for liquid which has been channeled from a liquid reservoir, e.g., a vial container, prior to being discharged via a pinhole formed at the end of the outlet portion 3108 of the aerosol tip mechanism 32.

As shown in FIGS. 9 and 11, for the first exemplary embodiment of the aerosol tip mechanism, the fluid channels (also referred to as "feed channels") 3104 initially extend longitudinally (vertically) along the walls 31021a, 31021b and 3102c, which walls circumferentially surround the rigid shaft 3102, then the fluid channels continue horizontally (radially) to deliver fluid into the swirling chamber 3103. It should be noted that wall 31021c is only shown in FIG. 11, and not shown in FIG. 9, for the sake of clarity of illustration. The vertical portion of the feed channels is designated as 3104a, and the horizontal portion is designated as 3104b. The fluid channels 3104 are described in further detail in later sections.

A brief description of the fluid mechanics involved in the fluid channels 3104 and the swirling chamber 3103 is helpful here. The swirling chamber 3103 is used to create a spray pattern for the discharged medicament, and several factors affect the physical characteristics of discharged spray pattern. First, the length of the pinhole formed at the end of the outlet portion 3108 is the main parameter controlling the cone angle of the spray pattern, i.e., the shorter the length of the pinhole at the end of the outlet portion 3108, the wider the spray pattern. Second, the greater the pressure differential between the outside and the inside of the pinhole opening at the end of the outlet portion 3108, the greater the homogeneity of the particles and the smaller the particle size. Third, the smaller the diameter of the pinhole at the end of the outlet portion 3108, the smaller the particle size in the spray.

In order to increase the homogeneity of the spray-particle size and generally reduce the particle size, the dispensing system according to the present invention maximizes the relative pressure differential between the outside and the inside of the pinhole opening at the end of the outlet portion 3108 by means of minimizing the resistance sources in the fluid path, also referred to as "head loss" in fluid mechanics. In this regard, the length of the fluid channel 3104 incorporated in the present invention is minimized, as well as the rate of reduction of the fluid-channel width as the fluid channel approaches the swirling chamber 3103, and the rate of change of the fluid-channel angle relative to the swirling chamber, i.e., the transition from the vertical portion 3104a to the horizontal portion 3104b is made as gradually as possible without unduly extending the overall length of the fluid channel 3104. Using the embodiment of the dispensing system incorporating the fluid channels and the swirling chamber shown in FIGS. 9 and 11, the average particle size of the discharged spray pattern was 40 $\mu$m.

Figure 28:
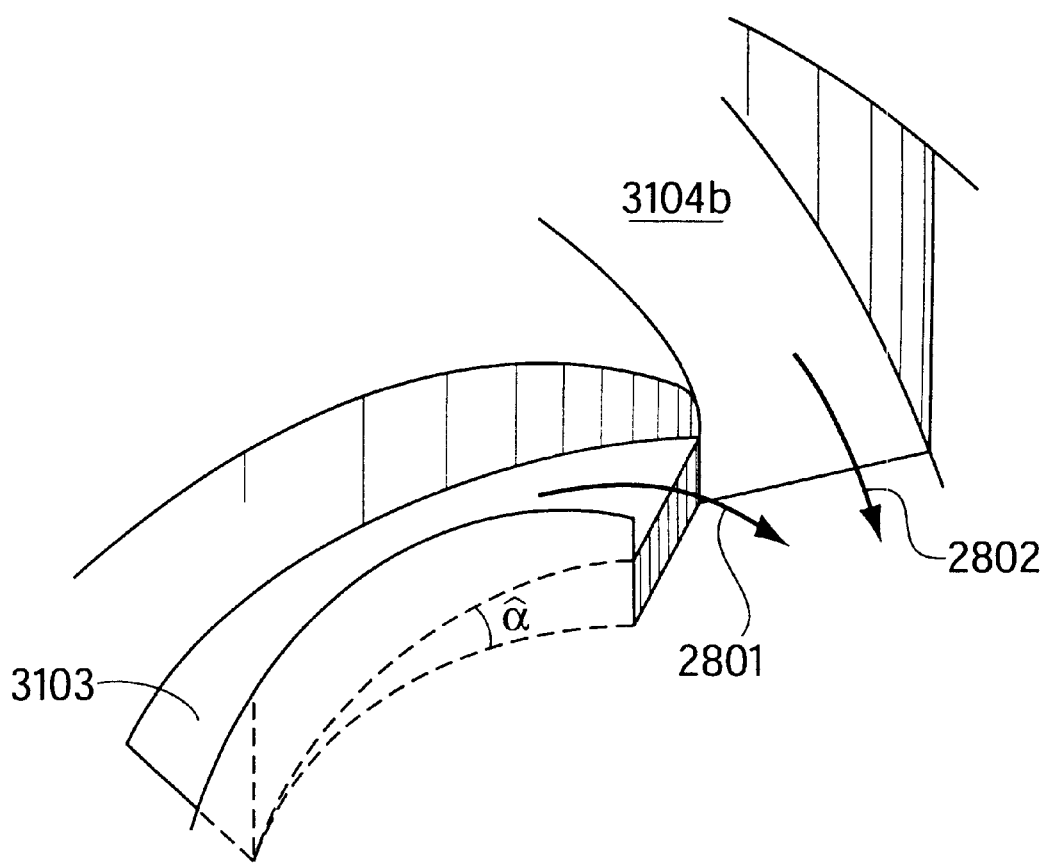
FIG. 28 is a perspective view illustrating the difference in height between a portion of the swirling channel and a converging fluid channel in an exemplary embodiment of the nozzle mechanism according to the present invention shown in FIGS. 9 and 11.

As shown in FIGS. 9 and 11, three separate horizontal channel portions 3104b merge into the swirling chamber 3103. In this configuration, additional reduction in head loss can be achieved by creating a relative difference in ramp slope $\alpha$ between the swirling chamber 3103 and the converging channel portions 3104b, as shown in FIG. 28, such that the liquid 2801 already swirling in the swirling chamber 3103 is already halfway to the top of the swirling chamber when this liquid merges with the liquid 2802 entering the swirling chamber 3103 from an adjacent horizontal channel portion 3104b.

Figure 14B:
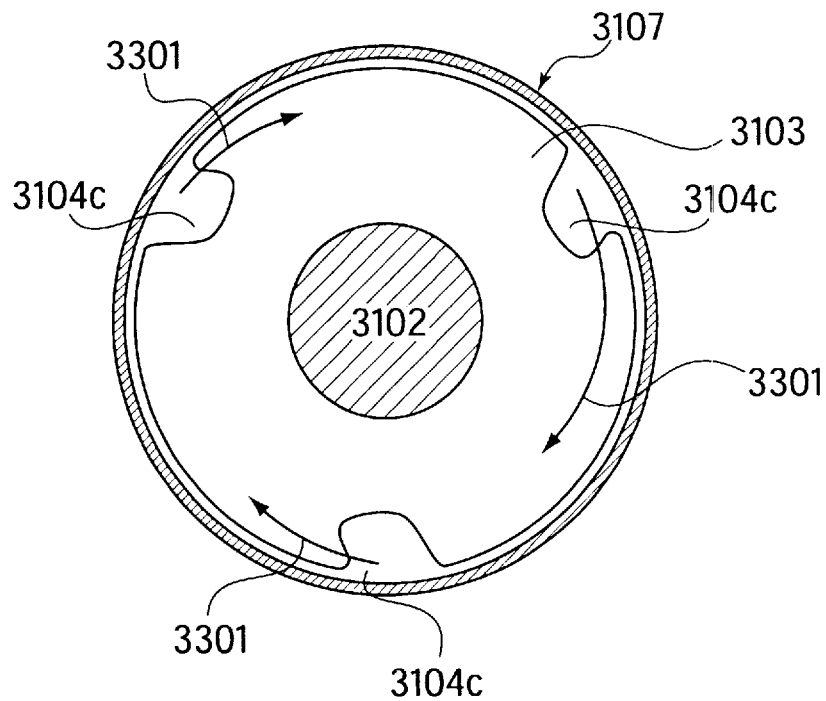
FIG. 14B is a cross-sectional view along line B—B shown in FIG. 14A.
Figure 14A:
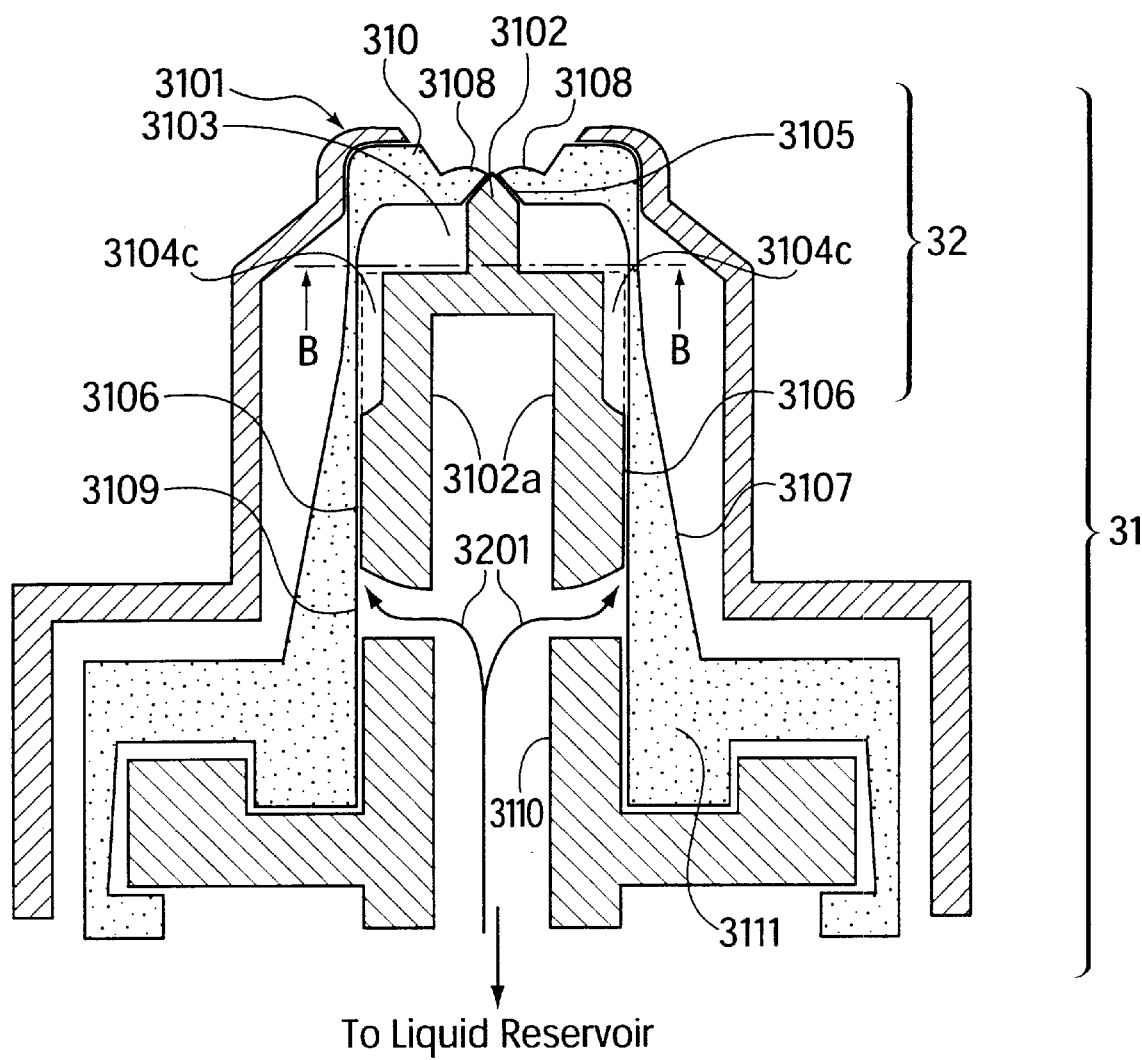
FIG. 14A is a cross-sectional view showing a second embodiment of the nozzle mechanism according to the present invention.

A second exemplary embodiment of the aerosol tip or nozzle mechanism 32 according to the present invention is shown in FIGS. 14A and 14B. The second exemplary embodiment is substantially similar to the first exemplary embodiment, with one exception. In contrast to the first exemplary embodiment shown in FIGS. 9 and 11, the second exemplary embodiment of the aerosol tip or nozzle mechanism does not include walls 31021a, 31021b and 31021c circumferentially surrounding the rigid shaft 3102, and the feed channel 3104 solely consists of obliquely vertically oriented channel extending along the interface of the exterior of the second portion 3102a of the rigid shaft and the interior surface of the flexible body portion 3107. Accordingly, in the second embodiment, the obliquely vertically oriented feed channel 3104 is connected directly to the swirling chamber 3103.

As shown in FIG. 9, the first exemplary embodiment of the aerosol tip or nozzle mechanism 32 according to the present invention is coupled to a flexible body portion 3107 which has a substantially tubular shape and a wall thickness which decreases from the bottom of the body portion toward the flexible nozzle portion 310, along the elongated axis of symmetry of the body portion. The rigid shaft 3102 received within the flexible nozzle portion 310 extends down into the flexible body portion 3107 so that a second portion 3102a of the rigid shaft interfaces the flexible body portion 3107 to form a second normally-closed valve 3106.

Figure 10:
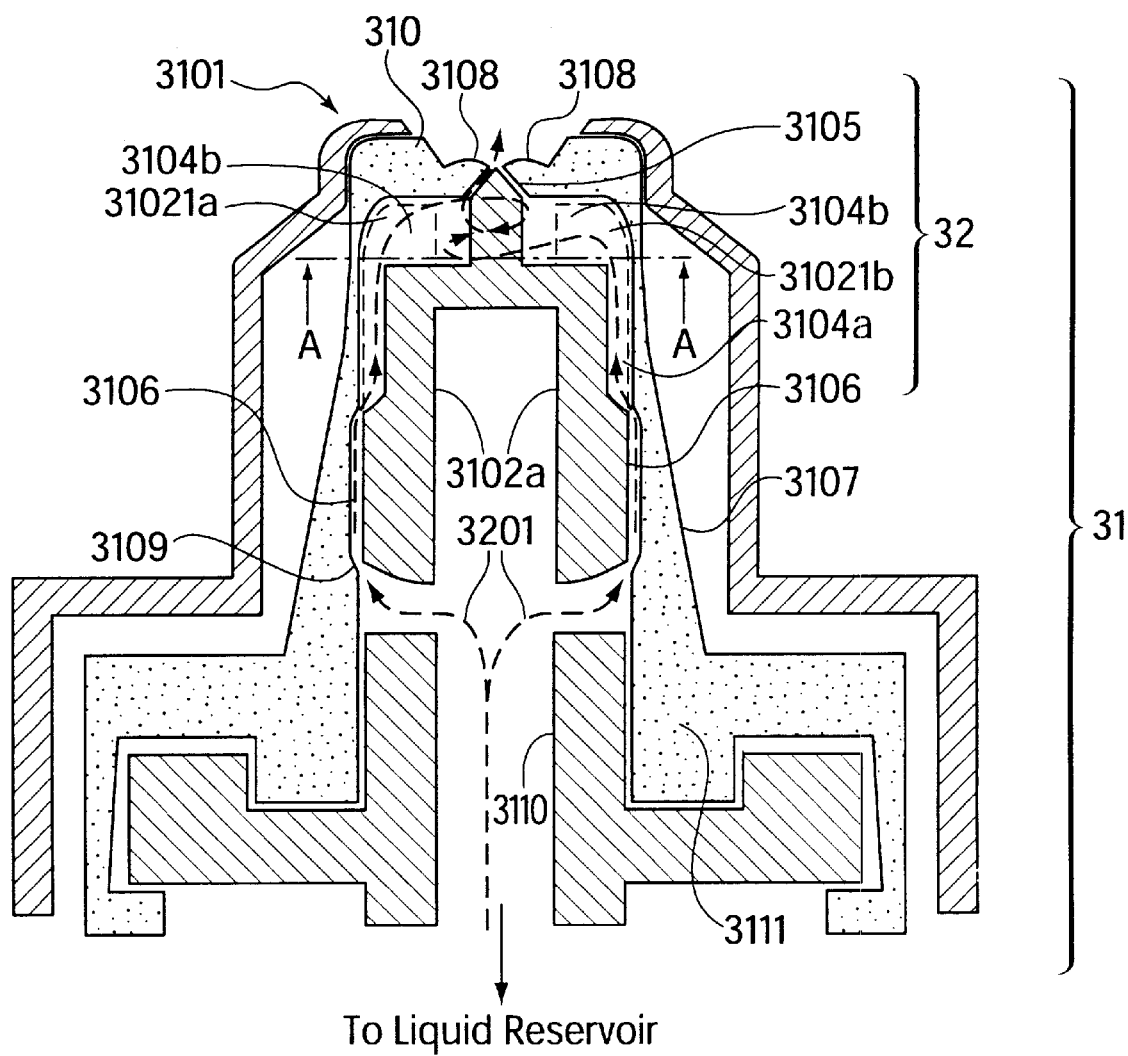
FIG. 10 is a cross-sectional view illustrating the flow path of liquid through the fluid communication path between the liquid reservoir and the nozzle mechanism of the aerosol dispenser shown in FIG. 9.

Referring generally to FIGS. 9 and 10, the fluid communication path 3201 of liquid from the liquid reservoir to the outlet portion 3108 successively traverses the first normally-closed valve 3106 and the second normally-closed valve 3105. A pump mechanism 3110 of the nasal dispenser system generally indicated by reference numeral 31, acting in concert with a pump-body portion 3111 of the dispenser system, channels the liquid from the liquid reservoir along the fluid communication path 3201 by application of pressure. A segment of the pump-body portion 3111 defines a portion of the first normally-closed valve 3106, which prevents the outflowing liquid from reversing direction and flowing back towards the liquid reservoir. It should be noted that the nozzle mechanism according to the present invention is intended to be used in conjunction with a wide variety of liquid dispensing systems, one example of which was illustrated previously in connection with FIGS. 3–8E. It should be understood that the pump mechanism 3110 and the pump-body portion 3111 of the dispenser system shown in FIGS. 9 and 10 are merely exemplary and generic representation of a wide variety of dispensing systems.

Figure 13A:
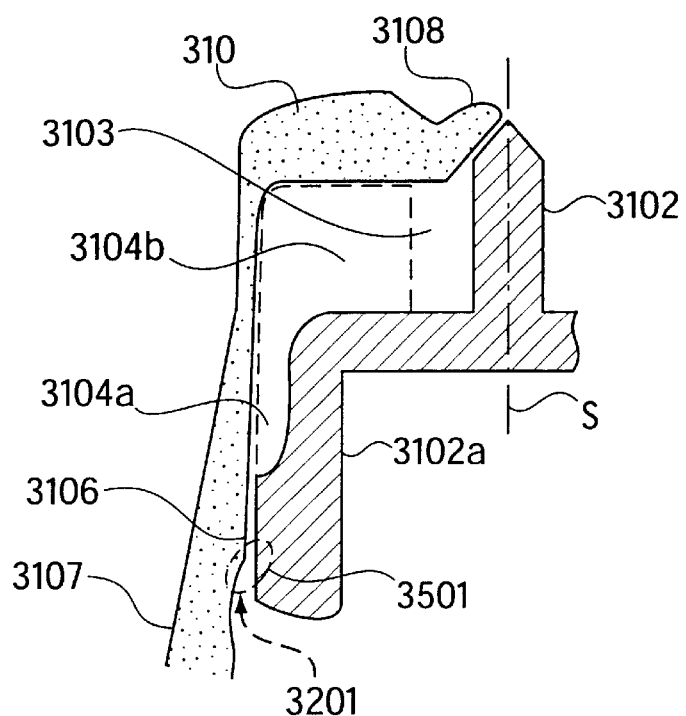
FIG. 13A is an enlarged cross-sectional view showing one stage of deformation of a valve in the body portion of the aerosol dispenser shown in FIG. 9.

As shown in FIGS. 9 and 10, the liquid from the liquid reservoir is initially channeled along the fluid communication path 3201 to the entrance point of the first normally-closed valve 3106 which regulates the liquid flow to the vertical portion 3104a of the feeding channel 3104 formed along the interface of the exterior of the second portion 3102a of the rigid shaft and the interior surface of the flexible body portion 3107. Once the pressure on the liquid in the fluid communication path reaches a threshold pressure sufficient to radially deform the flexible body portion 3107, a portion 3501 of the flexible body portion 3107 forming a lower segment of the first normally-closed valve 3106 is radially deformed by the liquid, thereby opening the first normally-closed valve 3106, as shown in FIG. 13A. As the liquid passes through the first normally-closed valve 3106 toward the vertical portion 3104a of the feeding channel 3104, sequential segments of the flexible body portion 3107 forming the first normally-closed valve 3106 are radially deformed, as shown in FIGS. 13A and 13B, until the liquid finally traverses the upper-most segment 3502 of the flexible body portion 3107 forming the first normally-closed valve 3106 and passes into the vertical portion 3104a of the feeding channel 3104.

Figure 13B:
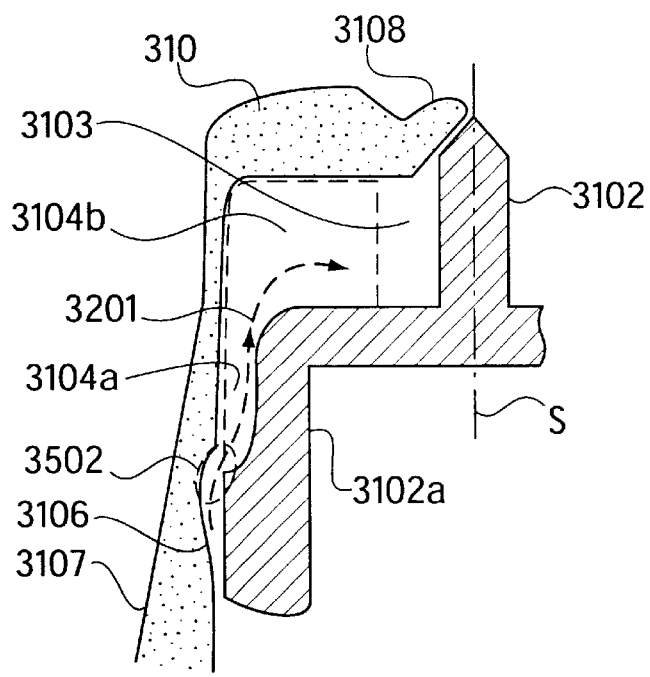
FIG. 13B is an enlarged cross-sectional view showing another stage of deformation of the valve in the body portion of the aerosol dispenser shown in FIG. 9.

As shown in FIGS. 13A and 13B, because the wall thickness of the flexible body portion 3107 decreases from the lower segment 3501 to the upper segment 3502 of the first normally-closed valve 3106, i.e., along the elongated axis of symmetry S of the nozzle mechanism, the lower segment 3501 of the valve 3106 is substantially closed by the time the liquid has reached the upper segment 3502. FIG. 13A illustrates the initial opening action of the segment 3501, and FIG. 13B illustrates the subsequent opening of the upper segment 3502. Because the energy required to open the lower segment 3501 of the valve 3106 is greater than the energy required to open the upper segment 3502, the liquid is naturally biased to maintain its forward movement through the first valve 3106 in the flexible body portion 3107 once the lower segment 3501 has been opened. In this manner, the first normally-closed valve 3106 ensures liquid movement only in the direction towards the vertical portion 3104a of the feeding channel 3104.

Once the liquid in the fluid communication path 3201 has traversed the first normally-closed valve 3106, the liquid then enters the vertical portion 3104a of the feed channel 3104 extending along the interface of the exterior of the second portion 3102a of the rigid shaft and the interior surface of the flexible body portion 3107 of the first embodiment of the aerosol tip mechanism 32, as shown in FIGS. 9, 10 and 11. The feed channel 3104 defines the portion of the fluid communication path 3201 between the first normally-closed valve 3106 and the swirling chamber 3103, and the vertical portion 3104*a* of the feed channel is connected to a horizontal, i.e., radial, portion 3104*b* of the feed channel which in turn is connected tangentially to the cylindrical swirling chamber 3103 within the flexible nozzle portion 310, as shown in FIGS. 11, 13A and 13B. The tangential connector of the horizontal portion 3104*b* of the feed channel 3104 to the cylindrical swirling chamber 3103 creates a swirling action of the liquid in the swirling chamber as indicated in FIG. 11 by the directional arrow 3301.

In the second embodiment of the aerosol tip mechanism shown in FIGS. 14A and 14B, the feed channel 3104 consists of only the obliquely vertical portion, designated 3104*c*, extending along the interface of the exterior of the second portion 3102*a* of the rigid shaft and the interior surface of the flexible body portion 3107. Accordingly, in the second embodiment of the aerosol tip mechanism, the liquid directly enters the swirling chamber 3103 via the obliquely vertically oriented feed channel 3104*c* once the liquid in the fluid communication path 3201 has traversed the first normally-closed valve 3106. The swirling action of the liquid, which is indicated by the directional arrow 3301 and is induced by the tangential (oblique) orientation of the feed channel 3104*c* relative to the swirling chamber 3103, is maintained in the swirling chamber until the liquid is discharged via the outlet portion 3108, the mechanics of which discharging action is described in detail below.

Referring generally to FIGS. 9, 12A and 12B, the liquid in the swirling chamber is discharged via the outlet portion 3108 when the liquid pressure reaches a threshold pressure sufficient to radially deform the outlet portion 3108 forming the second normally-closed valve 3105. As with the first normally-closed valve 3106 described above, the liquid movement through the second normally-closed valve 3105 involves sequential deformation of segments of the outlet portion 3108. As shown in FIG. 12A, a portion 3401 of the outlet portion 3108 forming a lower segment of the second normally-closed valve 3105 is radially deformed by the liquid, thereby opening the second normally-closed valve 3105. As the liquid passes through the second normally-closed valve 3105 toward the tip of the outlet portion 3108, sequential segments of the outlet portion 3108 forming the second normally-closed valve 3105 are radially deformed, as shown in FIGS. 12A and 12B, until the liquid finally passes through the upper-most segment 3402 of the outlet portion 3108 forming the second normally-closed valve 3105.

As shown in FIGS. 9, 12A and 12B, the wall thickness of the outlet portion 3108 decreases from the lower segment 3401 towards the upper segment 3402 of the second normally-closed valve 3105, i.e., along the elongated axis of symmetry S of the aerosol tip or nozzle mechanism. Due to this steady decrease in wall thickness, the lower segment 3401 of the valve 3105 is substantially closed by the time the liquid has reached the upper segment 3402, as shown in FIGS. 12A and 12B. Because the energy required to open the lower segment 3401 of the valve 3105 is greater than the energy required to open the upper segment 3402, the liquid is naturally biased to maintain its forward movement through the second valve 3105 in the outlet portion 3108 once the lower segment 3401 has been opened. Accordingly, the valve 3105 ensures liquid movement only in the direction towards the exterior tip of the nozzle portion 310.

During the discharge of liquid through the outlet portion 3108, the only segment of the flexible nozzle portion 310 which experiences deformation along the elongated axis of symmetry S of the aerosol tip or nozzle mechanism is the outlet portion 3108. The remaining segments of the flexible nozzle portion are prevented by the rigid housing 3101 from deformation along the elongated axis of symmetry S. Even the outlet portion 3108 experiences only minimal deformation along the axis S; the significant deformation is along the radial direction. Furthermore, the outlet portion 3108 does not exert a force along the axis S on the rigid shaft 3102, i.e., the outlet portion 3108 does not rub the rigid shaft during opening or closing of the second valve 3105. Accordingly, because of the absence of any rubbing contact between the outlet portion 3108 and the rigid shaft 3102, the chances of contaminants entering the swirling chamber 3103 are minimized.

Figure 12A:
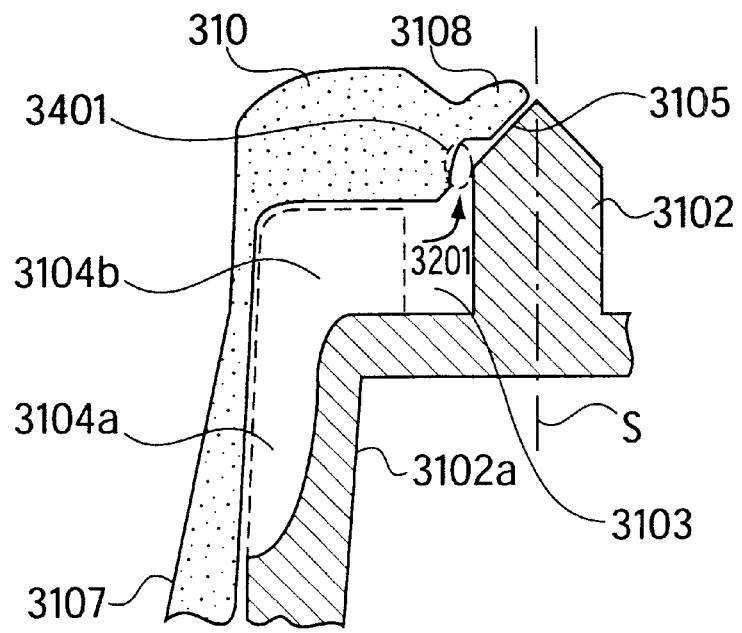
FIG. 12A is an enlarged cross-sectional view showing one stage of deformation of a valve in the nozzle mechanism according to the present invention shown in FIG. 9.
Figure 12B:
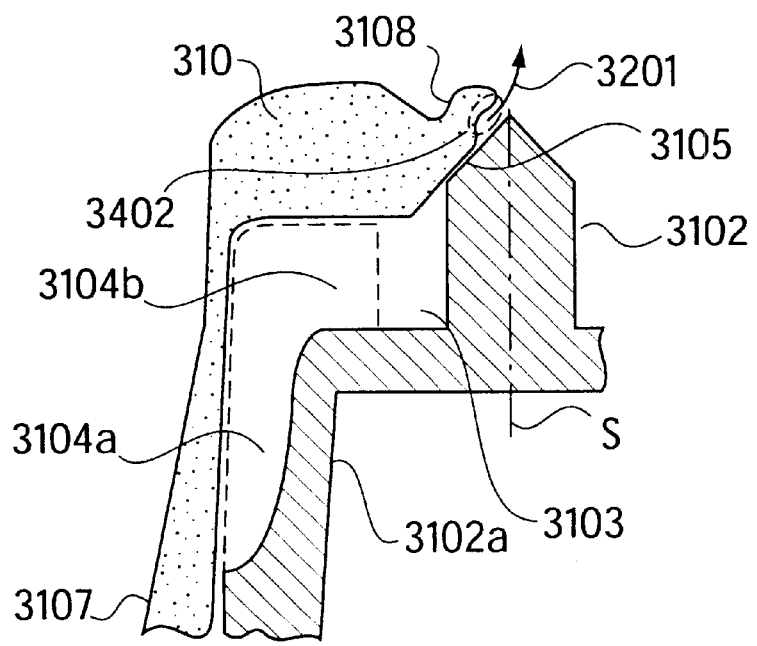
FIG. 12B is an enlarged cross-sectional view showing another stage of deformation of the valve in the nozzle mechanism according to the present invention shown in FIG. 9.

One advantage of the aerosol tip or nozzle mechanism according to the present invention is the above-described prevention of axial deformation of the flexible nozzle portion 310 by the rigid housing 3101. Because the flexible nozzle portion 310, with the exception of the outlet portion 3108, experiences substantially no deformation along the elongated axis of symmetry S shown in FIG. 12A, the physical profile of the fluid channel 3104, which induces swirling action of the liquid channeled into the swirling chamber 3103, is maintained during liquid discharge. An axial deformation of the flexible nozzle portion 310 along the direction of liquid discharge would deform the fluid channel 3104, which in turn would prevent the swirling action from occurring.

In the above-described embodiment of the aerosol tip or nozzle mechanism according to the present invention, the flexible nozzle portion 310, the flexible body portion 3107 and the pump-body portion 3111 may be made of any one of several materials well known in the art, including butadiene polyethylene styrene (KRATON™), polyethylene, polyurethane or other plastic materials, thermoplastic elastomers or other elastic materials. KRATON™ is particularly well suited for this purpose because of its characteristic resistance to permanent deformation, or "creep," which typically occurs with passage of time.

Another advantage of the aerosol tip or nozzle mechanism according to the present invention is that the number of parts which constitute the nozzle mechanism and, in turn, the nasal dispenser system which includes a pump mechanism in combination with the nozzle mechanism, is significantly reduced in comparison to conventional nozzle mechanisms. As can be seen from FIG. 9, a nasal dispenser system incorporating the nozzle mechanism according to the present invention can be made using only three discrete parts: the rigid housing 3101; an integral, flexible piece encompassing the flexible nozzle portion 310, the flexible body portion 3107 and the pump-body portion 3111; and the rigid shaft 3102 formed integrally with the pump mechanism 3110. Because only three discrete parts are required, the cost and complexity of manufacturing the nasal dispenser system is significantly reduced.

Yet another advantage of the aerosol tip or nozzle mechanism according to the present invention is that the second normally-closed, one-way valve 3105 with its decreasing wall thickness of the outlet portion 3108 substantially eliminates the possibility that liquid in the nozzle mechanism will come in contact with ambient air and subsequently return to the interior portion of the nozzle mechanism, i.e., that the liquid will be "sucked back." Due to the decreasing wall thickness of the outlet portion 3108, the liquid is naturally biased to maintain its forward movement through the second valve 3105 in the outlet portion 3108 once the thicker base portion of the valve has been opened. Accordingly, the outlet portion 3108 has a substantially zero "dead volume," i.e., a space in which liquid that has been previously exposed to ambient air can remain.

Still another advantage of the aerosol tip or nozzle mechanism according to the present invention is that the outlet portion 3108 does not rub the rigid shaft 3102 during opening or closing of the second valve 3105. Accordingly, because of the absence of any rubbing contact between the outlet portion 3108 and the rigid shaft 3102, the chances of contaminants entering the swirling chamber 3103 are minimized.

Still another advantage of the aerosol tip or nozzle mechanism according to the present invention is the presence of multiple valves along the fluid communication path leading to the outlet portion 3108. In addition to the second normally-closed valve, the first normally-closed valve positioned along the fluid communication path between the liquid reservoir and the outlet adds further assurances that liquid in the liquid reservoir will not be contaminated by liquid that may have been accidentally exposed to ambient air and subsequently reintroduced into the nozzle mechanism. Because the first and second normally-closed valves are positioned along the fluid communication path to open sequentially, and hence asynchronously, during fluid communication leading to discharge through the outlet, failure of either one of the valves will not affect the integrity of the nozzle mechanism to prevent contamination of the liquid in the liquid reservoir.

The medicament-dispensing system according to the present invention also incorporates a one-way actuation release mechanism, shown in FIGS. 15–17, in connection with the housing 101, shown in FIG. 1, which is adapted to house and work in conjunction with the accordion-like or piston-like vial-dispenser 4200, also shown in FIGS. 15–17. It should be understood that the vial-dispenser 4200 depicted in FIGS. 15–17 is a generalized representation of a system combining the pump system shown in FIGS. 3–8 and the nozzle mechanism shown in FIGS. 9–14, and the description of the components shown in FIGS. 15–17 will also be a generalized description of the corresponding components shown in FIGS. 3–14. Although the present invention is described in conjunction with the vial-dispenser generally depicted in FIGS. 15–17 and specifically depicted in FIGS. 3–14, the present invention is not limited to this particular type of dispenser, i.e., the pump system and the nozzle mechanism may be different from the ones described herein.

As shown in FIG. 15, the vial-dispenser generally depicted at 4200 includes a nozzle 42, a front ring 43, a front bellows portion 44, a rear ring 46, a rear bellows portion 47 and a rear vial section or liquid storage chamber 48 containing a storage supply of liquid medicament. The vial-dispenser 4200 is compressible in the longitudinal direction along the bellows. For this purpose, the front and rear bellows portions 44 and 47, respectively, are constructed of a soft flexible plastic material such as Kraton®. Resiliency of the dispenser is provided by the spring action of the front and rear bellows made of Kraton®, which has an excellent memory and serves as an excellent spring. It should be noted that the rear bellows portion 47 shown in FIG. 15 has a dome shape, and this dome shape may be incorporated into the front bellows portion 44. Similarly, the shape of the front bellows portion 44 shown in FIG. 15 may be incorporated into the rear bellows portion 47.

As shown in FIG. 16, the vial-dispenser 4200 further includes a drop cavity, or dosage cavity, 431 therein which holds, when the dispensing system is activated, a predetermined volume of fluid to be emitted through the nozzle 42. In addition, a pump piston 49 within the vial-dispenser is anchored to the rear ring 46 such that the piston 49 moves in unison with the rear ring 46. Furthermore, as shown in FIGS. 15 and 16, conduit channels 410, which connect the rear vial section 48 to the front bellows portion 44, and circumferential channels 411 within the front bellows portion 44, are provided to serve as conduits for supplying medicament to the drop cavity 431 upon actuation of the dispensing system. As will be described in further detail below, a single actuation motion of the trigger mechanism of the dispensing system sequentially accomplishes filling, or loading, of the drop cavity with medicament from the rear vial section 48, and subsequent discharge of the medicament from the drop cavity via the nozzle 42.

Figure 15:
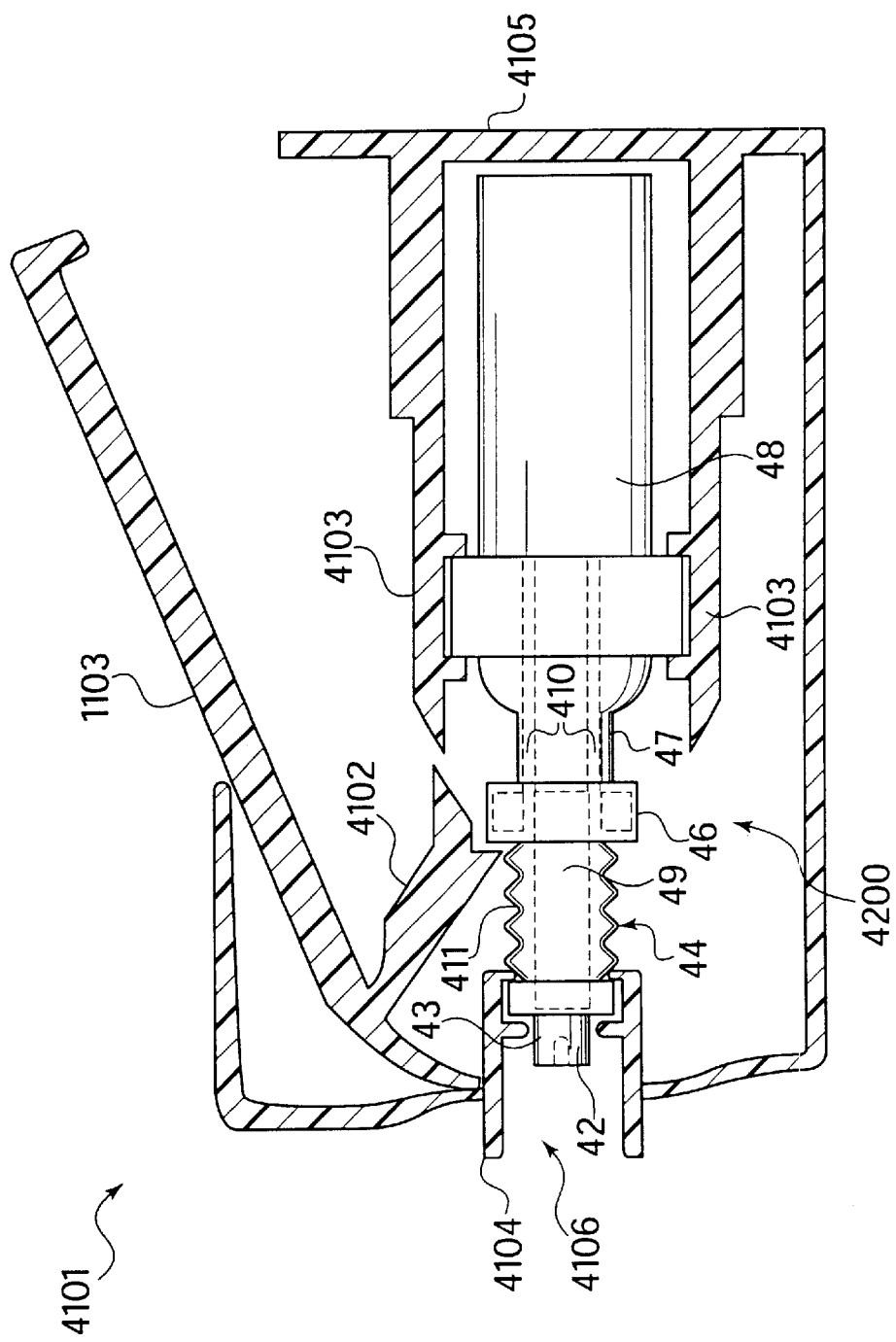
FIG. 15 is a detailed cross-sectional side view of a the dispensing system including the cartridge and the vial-dispenser in accordance with the present invention, which dispensing system is shown in a rest position.

As illustrated in FIG. 15, which represents a cross sectional view taken along the longitudinal axis of the dispensing system shown in FIG. 1, contained within the housing exterior housing 101 (not shown) is a cartridge 4101 of the dispensing system that includes an anterior wall 4104 which has an aperture 4106 for the discharge of medicament from the nozzle 42, a posterior wall 4105, wedge-shaped arms 4103 which extend internally from the posterior wall 4105, a trigger 1103 and an internal notched lever 4102 which acts in concert with the trigger 1103. It should be noted that although this particular embodiment is illustrated as having a separate external housing 101 and an internal cartridge 4101, some or all components of the external housing and the internal cartridge may be combined, e.g., the trigger button 103 of the external housing 101 shown in FIG. 1 may be the same component as the internal trigger 1103 shown in FIG. 15.

As shown in FIG. 15, the vial-dispenser 4200 is positioned within the cartridge 4101 such that in resting position the front ring 43 rests against the anterior wall 4104, the rear vial section 48 rests against the posterior wall 4105, and the notched lever 4102 engages the rear ring 46. Preferably, the cartridge 4101 is dimensioned such that the dispenser 4200 can fit snugly within the cartridge, with the nozzle 42 completely receded within the aperture 4106 of the anterior wall 4104, thereby preventing accidental contact of the nozzle 42 with the eye, as well as preventing contamination of the outside of the nozzle. In addition, the posterior wall 4105 may form, in conjunction with the wedge-shaped arms 4103, a rear chamber for accommodating the rear vial section 48.

Figure 16:
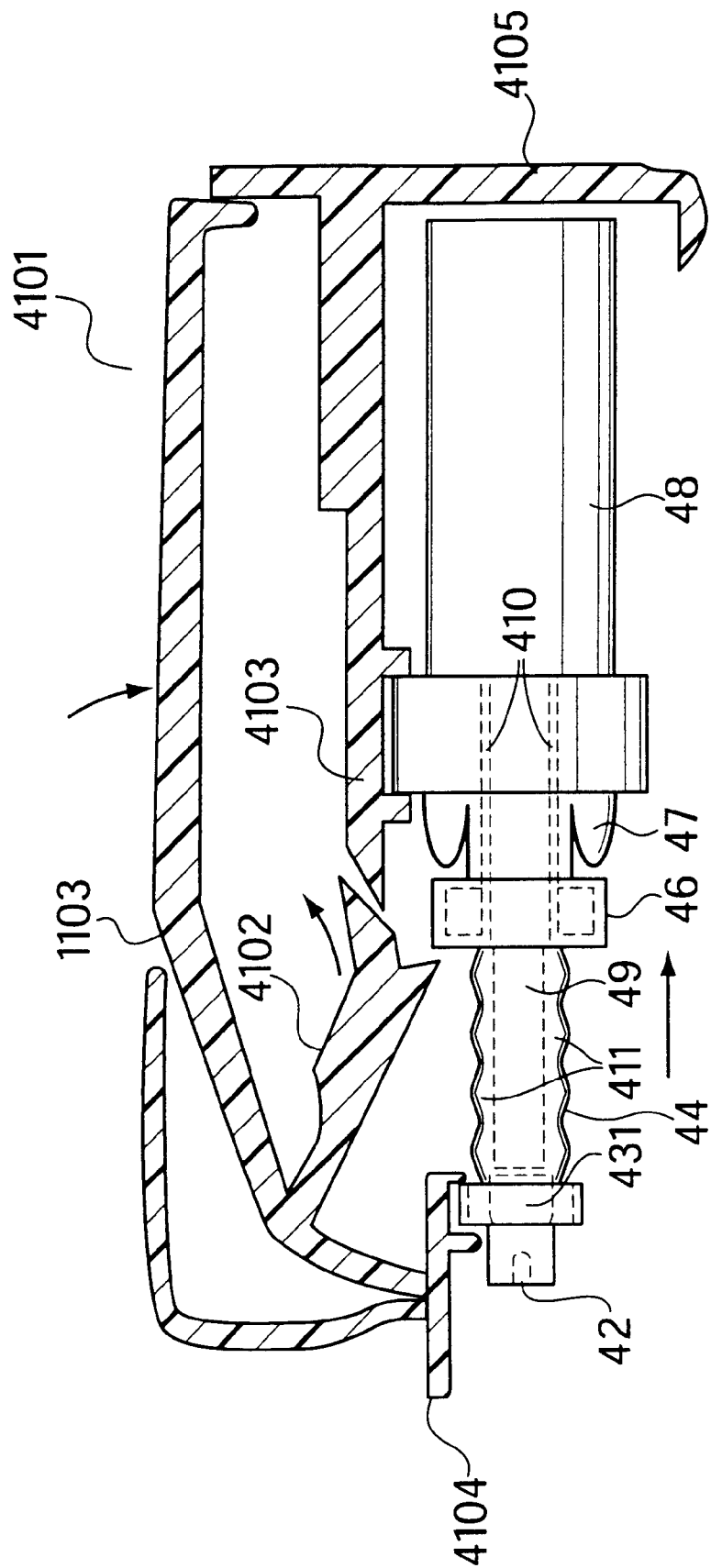
FIG. 16 is a detailed cross-sectional side view of the dispensing system including the cartridge and the vial-dispenser in accordance with the present invention, which dispensing system is shown in an intermediate position during actuation of the trigger mechanism.

From the rest position illustrated in FIG. 15, the dispensing system according to the present invention is actuated by depressing the trigger 1103. In concert with the depression of trigger 1103, the notched lever 4102 moves laterally towards the posterior wall 4105 while engaged to the rear ring 46, thereby extending the front bellows portion 44 and compressing the rear bellows portion 47 along the longitudinal axis of the vial-dispenser 4200, as shown in FIG. 16. As can be seen from FIGS. 15 and 16, when the front bellows portion is extended by the notched lever 4102 which is engaged to the rear ring 46, the internal pump piston 49 is also moved laterally towards the posterior wall 4105. The combined movement of the front bellows 44, the pump piston 49 and the rear bellows 47 causes drop in pressure in the drop cavity 431, and the drop cavity is filled, or "loaded," with medicament channeled from the rear vial section 48 via the conduit channels 410 and circumferential channels 411.

Figure 17:
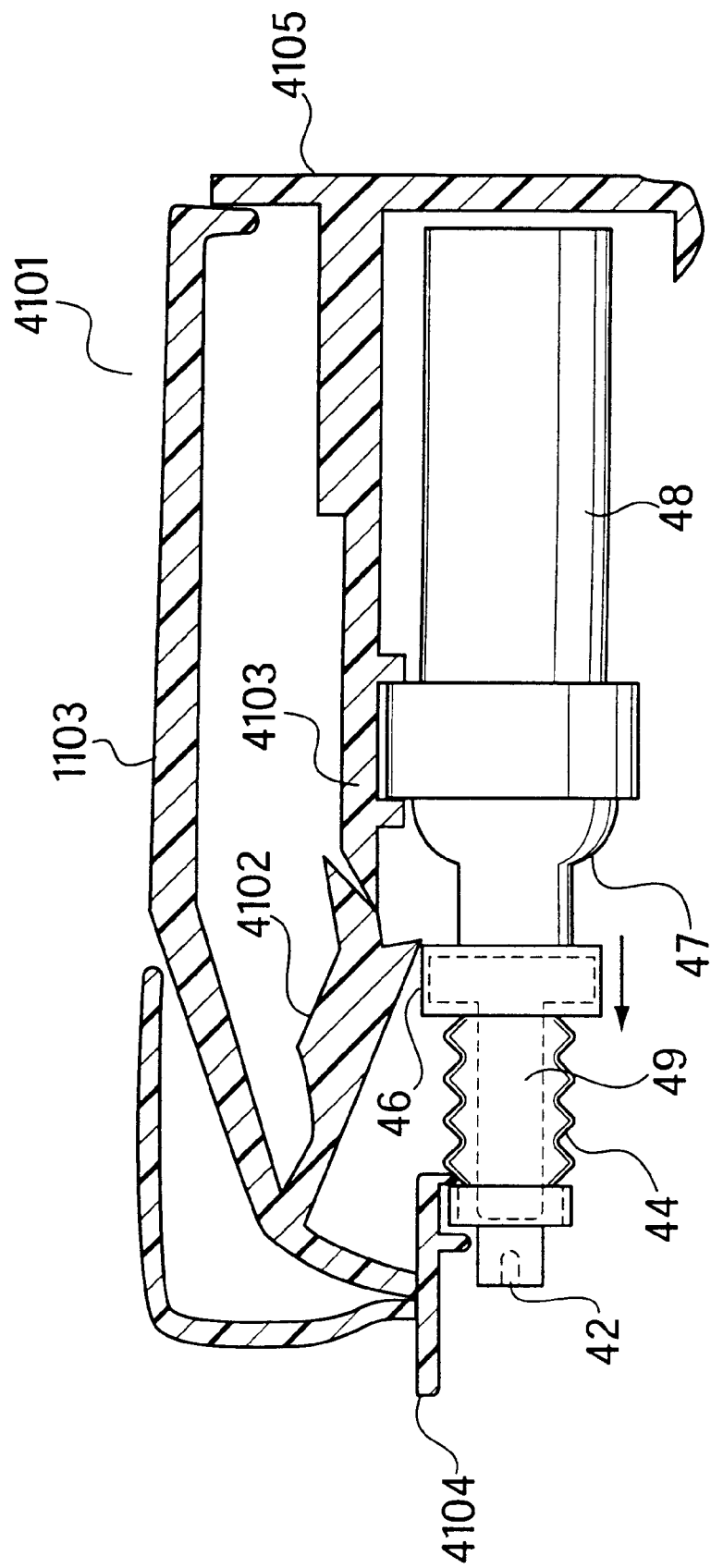
FIG. 17 is a detailed cross-sectional side view of the dispensing system including the cartridge and the vial-dispenser in accordance with the present invention, which dispensing system is shown in a release position during actuation of the trigger mechanism.

Continuing with the actuation sequence, further depression of the trigger 1103 causes the notched lever 4102 to eventually reach a position where the notched lever comes in contact with the wedge-shaped arm 4103. At this point, the wedge-shaped arm engages the notched lever 4102 and lifts the notched lever clear of the rear ring 46, as shown in FIG. 17. Upon release from the notched lever 4102, the spring action of the front bellows portion 44 and the rear bellows portion 47 causes the rear ring 46 and the pump piston 49 to move towards the anterior wall 4104, as shown in FIG. 17. The movement of the pump piston 49 creates pressure which forces the medicament to be discharged from the drop cavity 431 via the nozzle 42. Subsequently, when the trigger 1103 is released, the notched lever 4102 is disengaged from the wedge-shaped arm 4103, and the spring action of the notched lever 4102 allows the notched lever to snap back into the resting position shown in FIG. 15.

As can be seen from the above description, one advantage of the dispensing system according to the present invention is that there is virtually no possibility of the front and rear bellows portions exhibiting hysteresis of spring characteristics since the front and rear bellows portions are never "locked" in a deformed state for an extended period of time. Accordingly, the dispensing system according to the present invention ensures that the discharged dosages do not substantially deviate from the calibrated dosage. The consistency of the dispensed dosages is also ensured by the fact that the actuation spring force is independent of the force applied to the actuation mechanism by the user.

Another advantage of the dispensing system according to the present invention is that the actuation motion of the trigger 1103 is perpendicular to the longitudinal axis of the dispensing system. Accordingly, there is little danger of accidental poking of the nasal passage with the nozzle 42 since the motion to depress the trigger is not in the direction of the nasal passage.

Yet another advantage of the dispensing system according to the present invention is that a single actuation motion of the trigger 1103 perpendicular to the longitudinal axis of the dispensing system enables the user to both load the drop cavity and subsequently discharge the precalibrated amount of medicament. The dispensing system according to the present invention is particularly useful for arthritic patients and young children because the trigger mechanism is a lever which allows for very easy actuation and release of a medicament drop, thereby enabling more accurate delivery of the medicament drop to the nasal passage.

Figure 18:
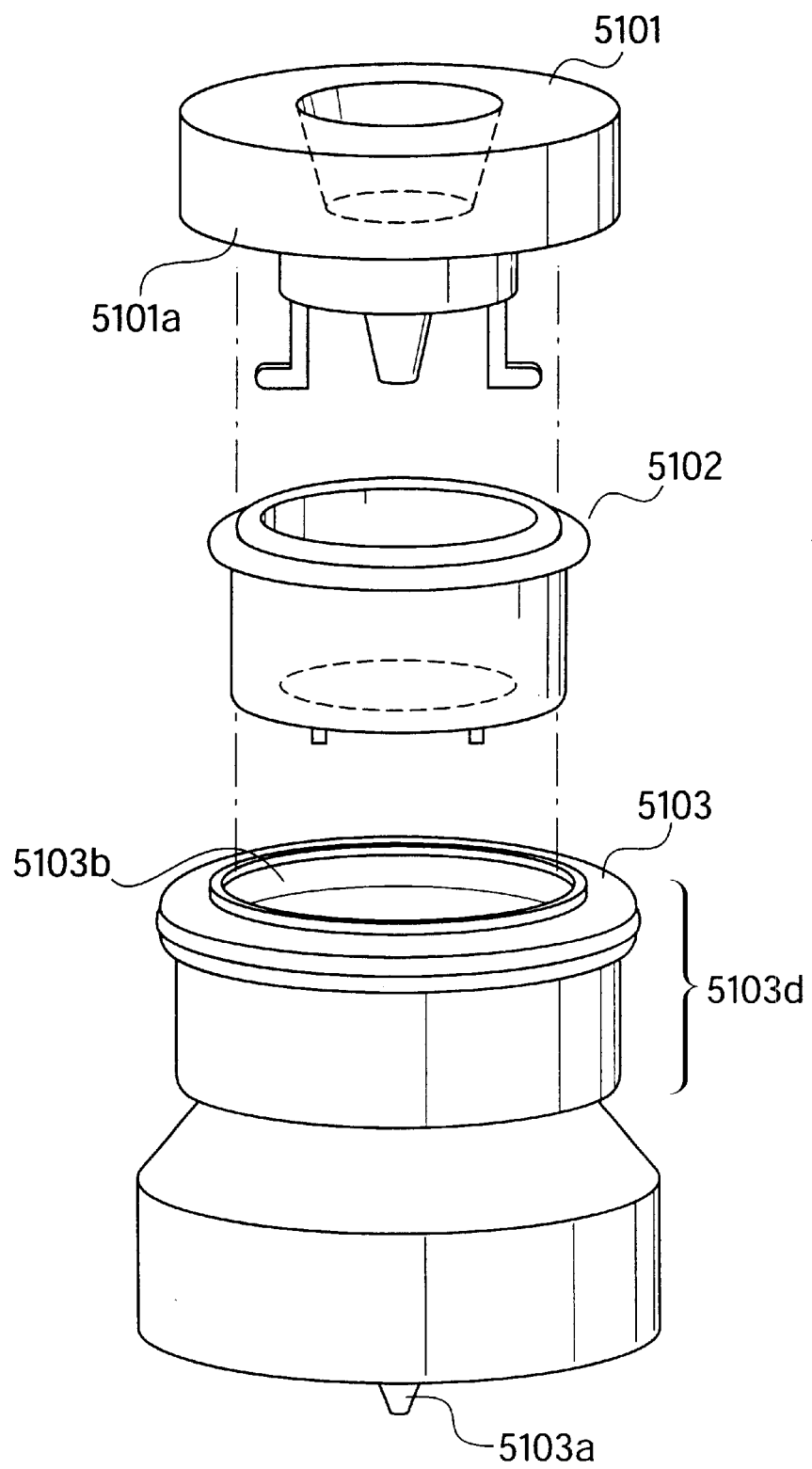
FIG. 18 is an exploded view of components of one preferred embodiment of the mechanical closure system incorporated in the dispensing system according to the present invention.

In order to facilitate fast, efficient and aseptic filling, the nasal dispenser system according to the present invention may incorporate a mechanical closure system for the liquid container portion of the system, e.g., the rear vial section generally indicated by reference numeral 48 in FIG. 15. As shown in FIG. 18, which is an exploded view of a first exemplary embodiment of a mechanical closure system according to the present invention, the first embodiment includes a mechanical lid or plug 5101 and a rigid annular ring 5102, both of which interact with a neck region 5103d near an opening 5103b of a pouch or container 5103 to tightly seal the opening 5103b. The pouch or container 5103 may be made of any one of several materials well known in the art, including butadiene polyethylene styrene (KRATON™), polyethylene, polyurethane or other plastic materials, thermoplastic elastomers or other elastic materials. As shown in FIG. 18, the container 5103, which has a nozzle 5103a, is a generalized representation of a medicament dispensing system with a nozzle, for example, the vial dispenser 4200 shown in FIG. 15. However, it should be noted that the neck region 5103d near the opening 5103b of the nozzle 5103 is a more detailed, exemplary depiction of the corresponding portion of the rear vial section 48 shown in FIG. 15, i.e., the end portion facing the wall 4105, which end portion is shown without a mechanical closure element.

Figure 19:
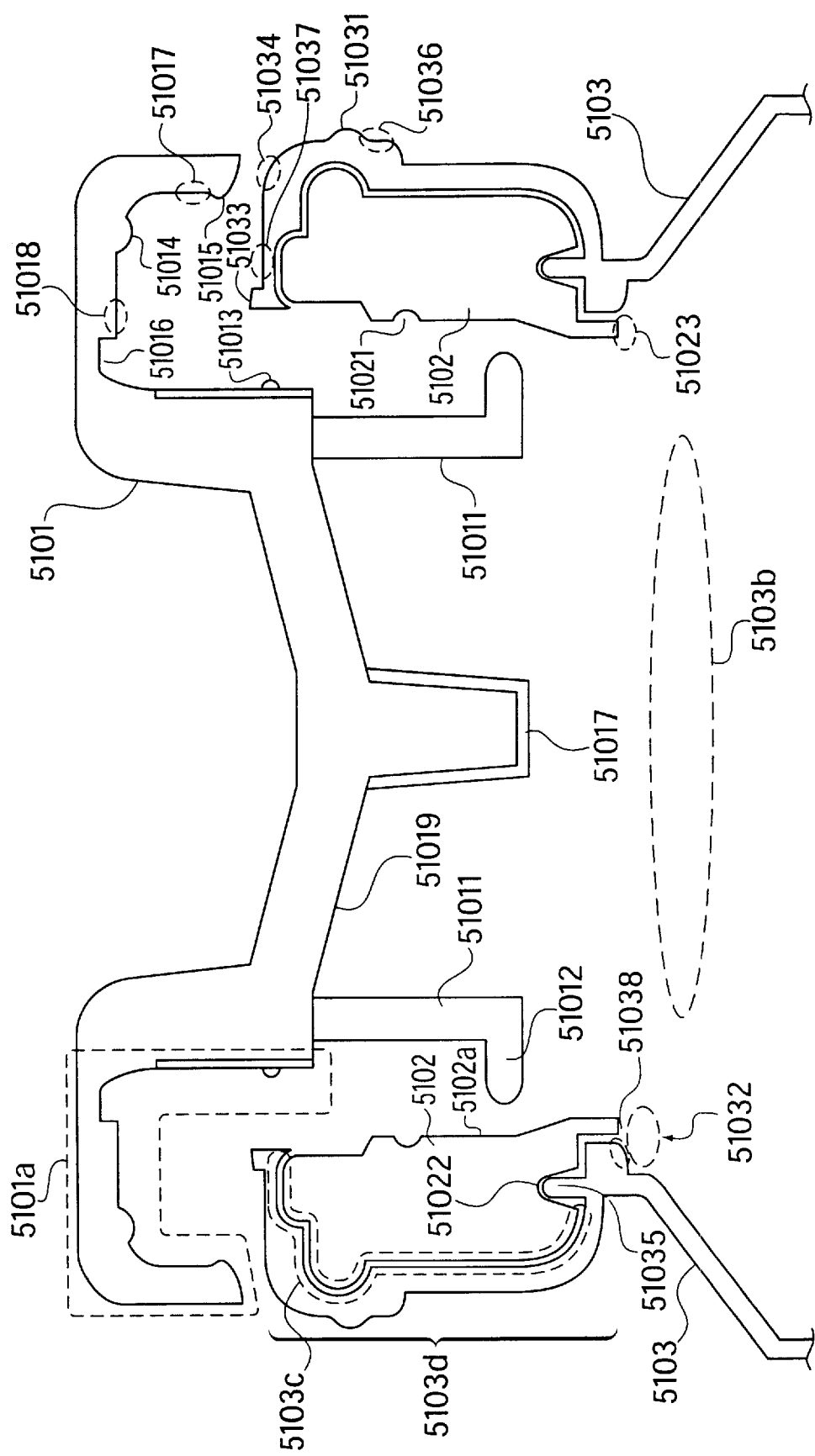
FIG. 19 is an exploded cross-sectional view of components of the preferred embodiment of the mechanical closure system according to the present invention shown in FIG. 18.

As shown in FIG. 18, which is an exploded cross-sectional view of the first embodiment of the mechanical closure system according to the present invention, the contour of the rigid ring 5102 is complementary to the inside contour 5103c of the neck region 5103d of the container 5103 near the opening 5103*b*, thereby allowing the rigid ring 5102 to be snapped into the inside contour 5103*c* of the neck region 5103*d*. Similarly, as shown in FIGS. 18 and 19, radial edge 5101*a* of the mechanical plug 5101 is formed as a U-shaped region which extends around the plug and complements the exterior contour of the combination of the rigid ring 5102 and the neck region 5103*d*. After the rigid ring 5102 has been snapped into the inside contour 5103*c* of the neck region 5103*d*, the mechanical plug 5101 is subsequently snapped into place around the container opening 5103*b* such that the U-shaped region 5101*a* tightly engages the neck region 5103*d* of the pouch 5103 and the interior surface of the rigid ring 5102.

As shown in FIG. 19, the U-shaped region 5101*a* of the mechanical plug 5101 has protrusions 51013, 51014 and 51015, and at least one recess 51016. Similarly, the exterior surface of the neck region 5103*d* of the mechanical plug has protrusions 51031 and 51033, and the interior surface of the neck region has a protrusion 51035. In addition, the rigid ring 5102 has recesses 51021 and 51022 at the vertical interior surface 5102*a* and the bottom surface, respectively. The recess 51022 of the rigid ring 5102 accommodates the protrusion 51035 of the neck region 5103*d*, thereby securely engaging the rigid ring to the neck region of the container 5103 once the rigid ring has been snapped into place. The protrusions 51013, 51014 and 51015, as well as a portion 51018, of the U-shaped region 5101*a* of the mechanical plug engage the recess 51021 of the rigid ring and portions 51034, 51036 and 51037 of the exterior surface of the neck region 5103*d*, respectively. In addition, the protrusions 51031 and 51033 of the exterior surface of the neck region 5103*d* engage a portion 51017 and the recess 51016 of the U-shaped region 5101*a* of the mechanical plug.

In addition to the above-described combinations of interlocking protrusions and recesses, attached to the lower surface of the mechanical plug 5101 are at least two legs 51011 which extend perpendicularly to the lower surface of the mechanical plug, as shown in FIG. 19. Each of the legs 51011 has a hook-shaped end portion 51012 adapted to engage a recess region 51032 at the bottom interior of the assembled combination of the rigid ring 5102 and the neck region 5103*d* of the mechanical plug. The legs 51011 are flexible enough such that, during assembly of the mechanical closure system according to the present invention, the legs 51011 slide down the vertical interior surface 5102*a* of the rigid ring and snap into place at the recess region 51032, against a portion 51038 of the neck region 5103*d* of the container.

The combination of the U-shaped region 5101*a* and the legs 51011 of the mechanical plug 5101 facilitates both vertical and radial compression of the neck region 5103*d* of the container and the rigid ring against the mechanical plug. For example, as shown in FIG. 19, the portion 51012 of the legs 1011 interact with the portion 51023 of the rigid ring and the portion 51038 of the neck region 5103*d* of the container, and portions 51014 and 51018 of the mechanical plug interact with portions 51034 and 51037 of the neck region 5103*d* of the container, respectively, to vertically compress the neck region between the mechanical plug 5101 and the rigid ring 5102. Similarly, the portions 51013, 51015 and 51017 of the U-shaped region 5101*a* of the mechanical plug 5101 interact with the portions 51021, 51036 and 51031, respectively, to radially compress the neck region 5103*d* between the mechanical plug and the rigid ring 5102. In this manner, a substantially hermetic seal of the container opening 5103*b* is achieved, as shown in FIG. 20.

Figure 20:
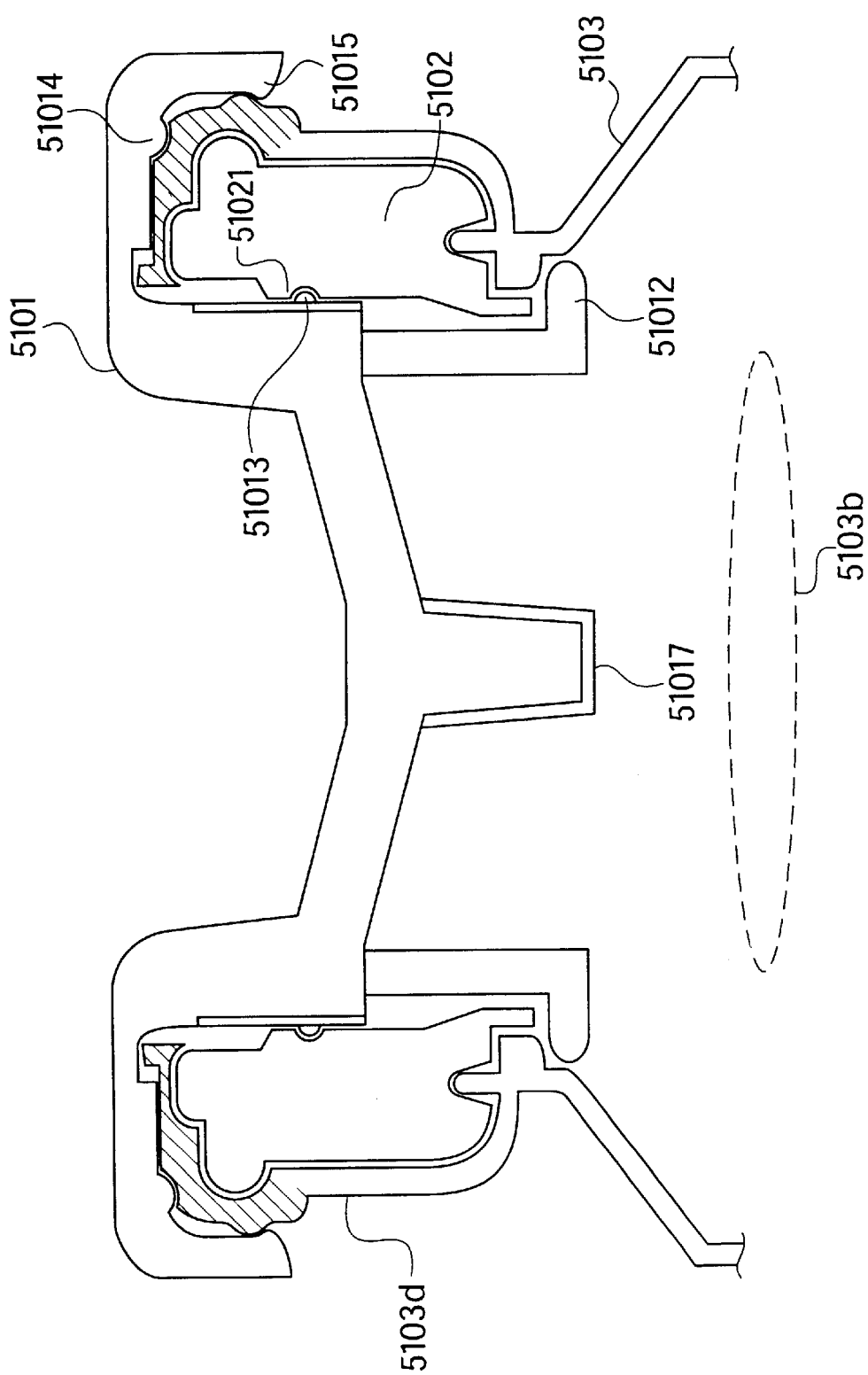
FIG. 20 is a cross-sectional view of assembled components of the preferred embodiment of the mechanical closure system according to the present invention shown in FIG. 18.

As can be understood from the above description and FIGS. 19 and 20, the first embodiment of the mechanical closure system according to the present invention achieves two types of mechanical seals. First, a seal extending along the horizontal direction of the neck region, e.g., the area extending between the portions 51034 and 51037, as well as the interface of the regions 51022 and 51035, is achieved by the vertical compression of the neck region 5103*d* by the mechanical plug against the rigid ring 5102. Second, a seal extending along the vertical direction, e.g., the area extending between the portions 51036 and 51034, as well as the interface of the regions 51021 and 51013, is achieved by the horizontal compression of the neck region 5103*d* by the mechanical plug against the rigid ring 5102.

Once the mechanical plug has been snapped into the container opening, the resulting compression of the container material tends to cause displacement, or "creep," of the compressed material towards areas of lesser compression. The protrusions force the container material displaced by compression to be confined within a restricted area, thereby ensuring the tightness of the seal for a prolonged period of time. For example, the protrusions 51014 and 51015 of the mechanical plug 5101 delimits the protrusion 51031 on the exterior surface of the neck region 5103*d* of the container. Accordingly, when the material of the protrusion 51031 is initially compressed by the portions 51015 and 51017, the displaced material of the protrusion 51031 is forced towards the protrusion 51014, which limits any further movement of the displaced material, thereby maintaining a tight seal. In effect, the relative arrangement of protrusions 51014, 51015 and 51031 constructively guides the creeping phenomenon for sealing enhancement.

As shown in FIGS. 19 and 20, the central portion of a lower surface 51019 of the mechanical plug 5101 is preferably equipped with an extension or a plunger 51017 which is adapted to extend into the liquid content of the container before the mechanical plug 5101 has been snapped into place around the container opening 5103*b*. The inserted plunger 51017 forces the liquid level to rise, hence allowing air or gas bubbles to rise along with the liquid level and escape through the container opening 5103*b* which is not yet sealed by the mechanical plug 5101. In this manner, the plunger 51017 substantially reduces the residual air bubbles which may otherwise remain between the surface of the liquid and the lower surface of the mechanical plug. The configuration and dimensions of the mechanical plug 5101, the neck region 5103*d* and the rigid ring 5102 are such that the U-shaped region 5101*a* and the legs 51011 of the mechanical plug interact with the neck region 5103*d* and the rigid ring 5102 to form a tight seal only after the plunger 51017 has forced the liquid level to rise to approximately the upper edge of the neck region 5103*d*, thereby obviating the need for a vacuum condition normally utilized for an air-less filling process.

The lower surface 51019 of the mechanical plug 5101 is sloped in order to ensure that the air or gas bubbles which have been forced up to the surface level of the liquid by the insertion of the plunger 51017 are not trapped between the liquid level and the lower surface of the mechanical plug. The sloped surface 51019 facilitates radially upward movement of the air bubbles which eventually escape through the opening 5103*b* of the container, via the area between the two legs 51011.

Figure 21:
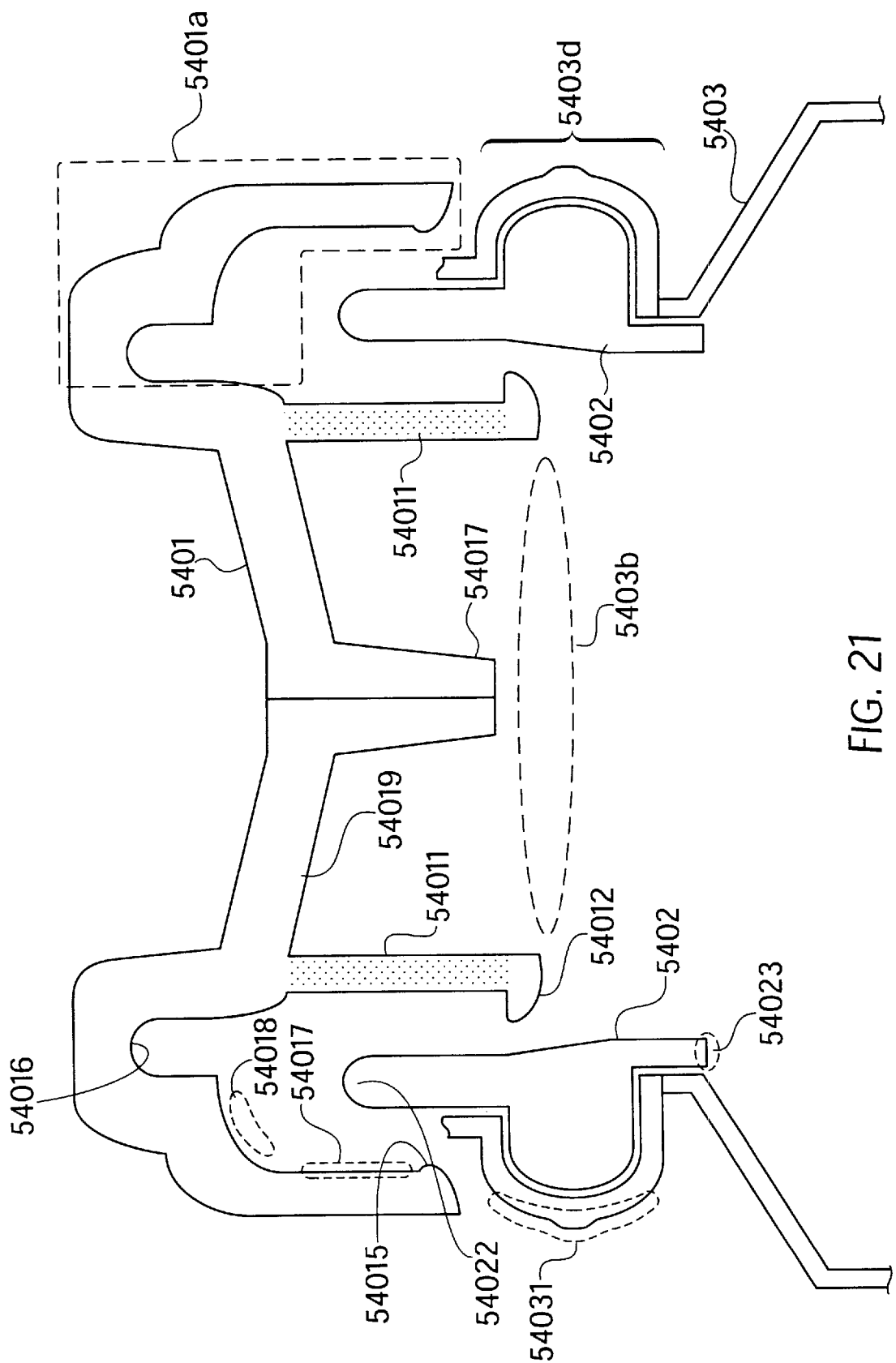
FIG. 21 is an exploded cross-sectional view of components of another preferred embodiment of the mechanical closure system according to the present invention.

As shown in FIG. 21, which is an exploded cross-sectional view of a second exemplary embodiment of a mechanical closure system according to the present invention, the second embodiment of the present invention is substantially similar to the first embodiment and includes a mechanical plug or plug 5401 and a rigid annular ring 5402, both of which interact with a neck region 5403d of a pouch or container 5403. As in the first embodiment described in conjunction with FIGS. 18–20, the contour of the rigid ring 5402 is complementary to the inside contour of the neck region 5403d of the container 5403, thereby allowing the rigid ring 5402 to be snapped into the inside contour of the neck region 5403d. In addition, radial edge 5401a of the mechanical plug 5401 is formed as an arch-shaped region which extends around the plug and complements the exterior contour of the combination of the rigid ring 5402 and the neck region 5403d. After the rigid ring 5402 has been snapped into the inside contour of the neck region 5403d, the mechanical plug 5401 is subsequently snapped into place around the container opening 5403b defined by the neck region 5403d such that the arch-shaped region 5401a tightly engages the neck region 5403d of the pouch 5403 and the rigid ring 5402, as shown in FIG. 22.

As with the first embodiment of the mechanical closure system, the lower surface 54019 of the mechanical plug 5401 of the second embodiment is sloped, or tapered, in order to ensure that the air or gas bubbles which have been forced up to the surface level of the liquid by the insertion of the plunger 54017 are directed radially upward and eventually escape through the opening 5403b of the container, via the area between the two legs 54011.

Figure 22:
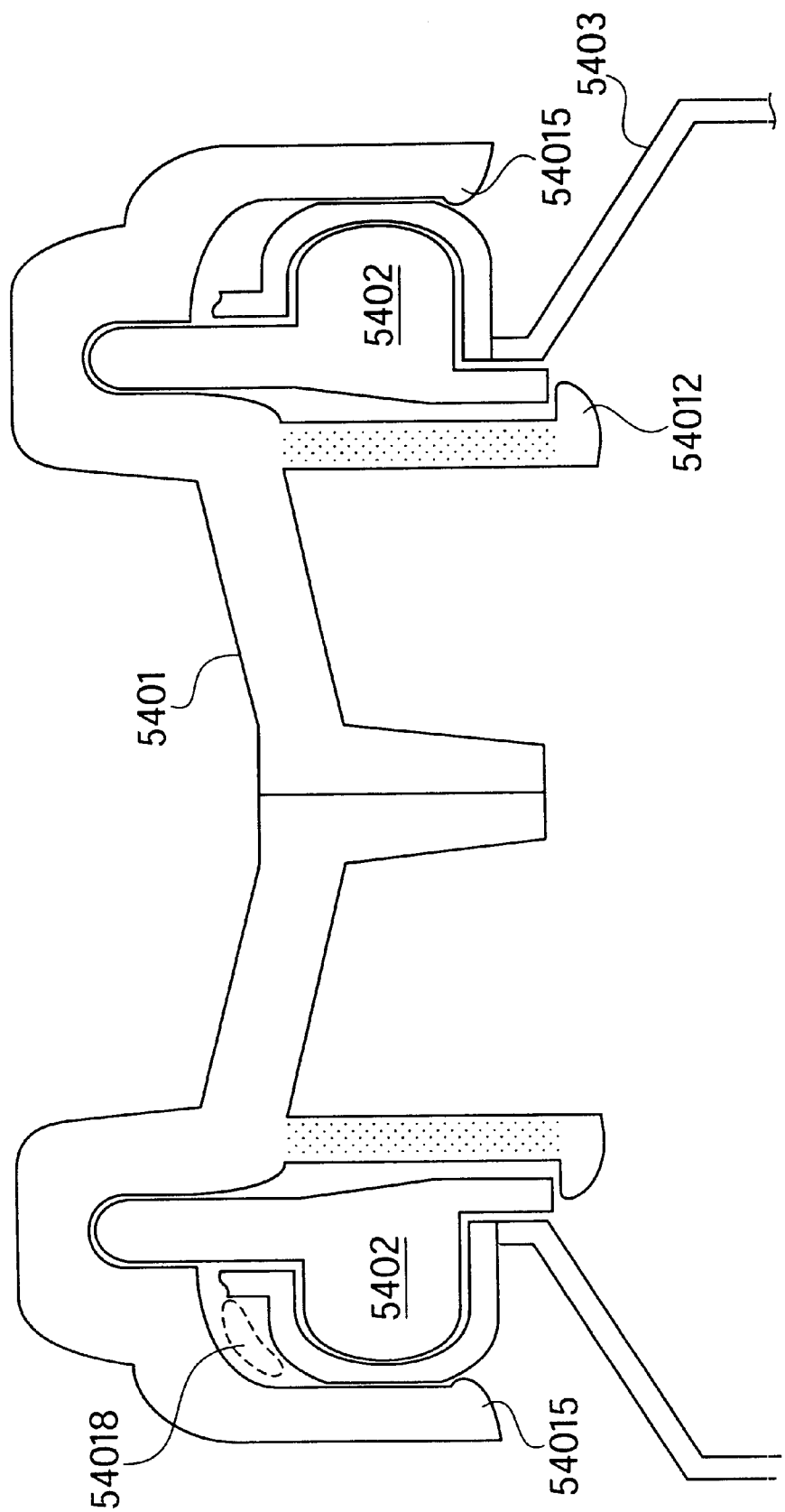
FIG. 22 is a cross-sectional view of assembled components of the preferred embodiment of the mechanical closure system according to the present invention shown in FIG. 21.

In addition, similar to the first embodiment of the mechanical closure system, the second embodiment shown in FIGS. 21 and 22 preferably have at least two legs 54011 attached to the lower surface of the mechanical plug 5401, each of the legs having a hock-shaped region 54012 at the end. The hook-shaped region 54012 is adapted to engage a region 54023 at the bottom surface of the rigid annular ring 5402. In addition, attached to the central lower surface of the mechanical plug 55401 is an extension or a plunger 54017 which is adapted to extend into the liquid content of the container before the mechanical plug 5401 is snapped into place around the container opening 5403b, thereby substantially reducing the residual air bubbles which may otherwise remain between the surface of the liquid and the lower surface of the mechanical plug.

The second embodiment of the mechanical closure system according to the present invention utilizes fewer protrusions on the surfaces of the mechanical plug 5401 and the neck region 5403d than the number of protrusions found on the corresponding parts of the first embodiment. However, the unique arrangement of the interacting components, i.e., the mechanical plug 5401, the rigid ring 5402 and the neck region 5403d, ensures a substantially hermetic seal of the pouch 5403. As shown in FIGS. 21 and 22, a protrusion 54015 and a region 54017 of the mechanical plug interact with a region 54031 of the neck region 5403d, which region 54031 includes a protrusion from the regular contour of the exterior surface of the neck region 5403d, and a portion 54016 of the mechanical plug interacts with the region 54022 of the rigid ring 5402, thereby achieving radial compression of the rigid ring 5402 and the neck region 5403d. In addition, portions 54016 and 54012 of the mechanical plug interact with regions 54022 and 54023 of the rigid ring 5402 to vertically compress the neck region 5403d and the rigid ring 5402.

In order to ensure that the displacement or creep of the container material around the points of compression does not result in reduced tightness of the seal, the second embodiment of the mechanical closure system provides the protrusion 54015 at the radial edge of the mechanical plug 5401. As shown in FIGS. 21 and 22, the protrusion 54015 forces the container material of region 54031 displaced by compression to be channeled upwards, towards a space 54018 delimited by the annular rigid ring 5402. Accordingly, the protrusion 54015 and the rigid ring 5402 confine the displaced material of the region 54031 of the container 5403, thereby maintaining a tight seal for a prolonged period of time.

Figure 23A:
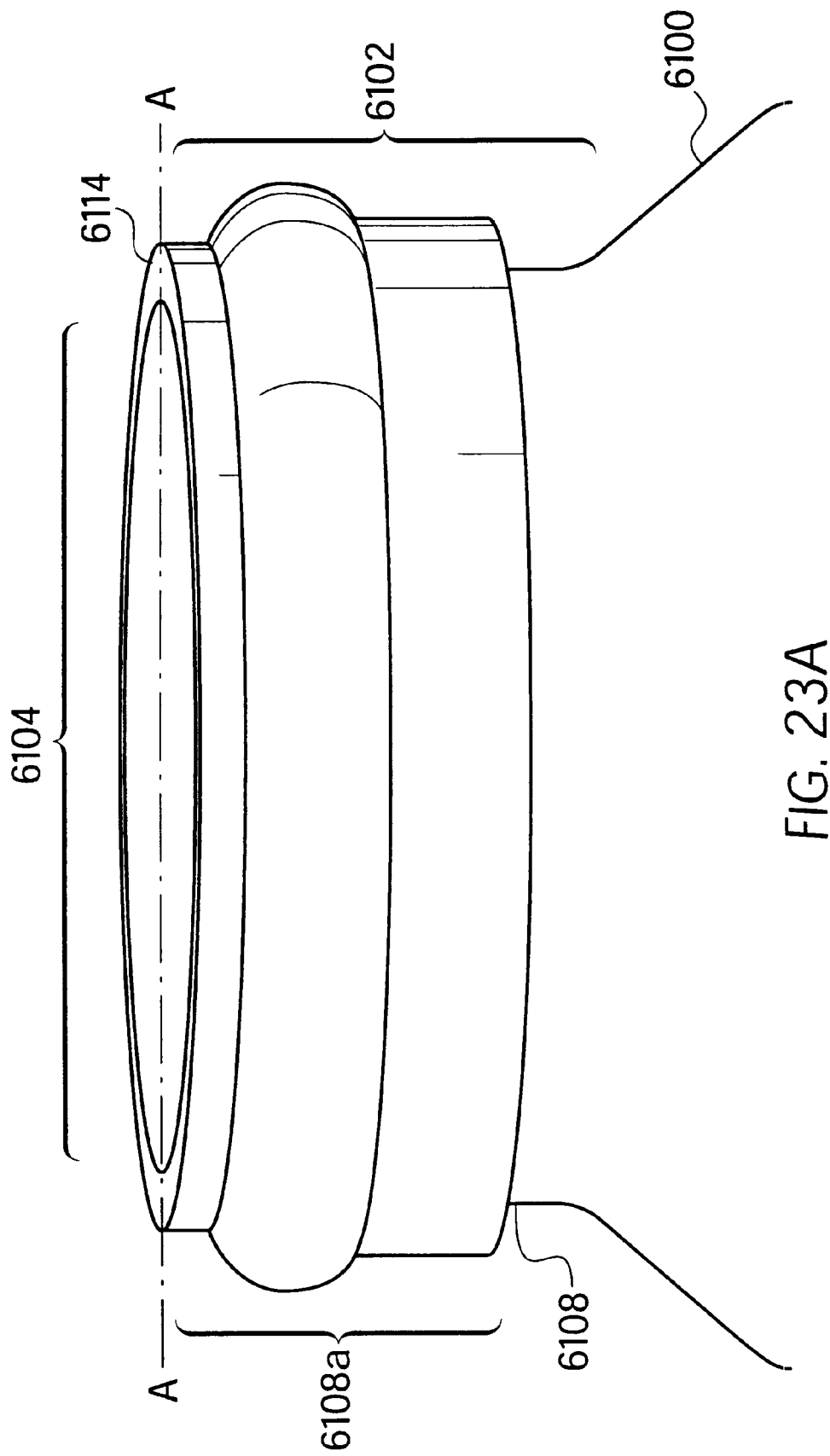
FIG. 23a is a perspective view of a neck of a container of an exemplary embodiment of the mechanical closure system according to the present invention.

As an alternative means of facilitating an efficient and aseptic filling and closure of the phial-type pump mechanism incorporated in the nasal dispenser system according to the present invention, a "self-crimping" mechanical closure system may be utilized. FIG. 23a shows a perspective view of a neck 6102 of a container or pouch 6100 adapted for use in connection with an exemplary embodiment of the self-crimping mechanical closure system. The container 6100 is another generalized depiction of the rear vial section 48 shown in FIG. 15, and the neck 6102 is a more detailed, exemplary depiction of the corresponding portion of the rear vial section 48, i.e., the end portion facing the wall 4105, which end portion is shown without a mechanical closure element.

Figure 23B:
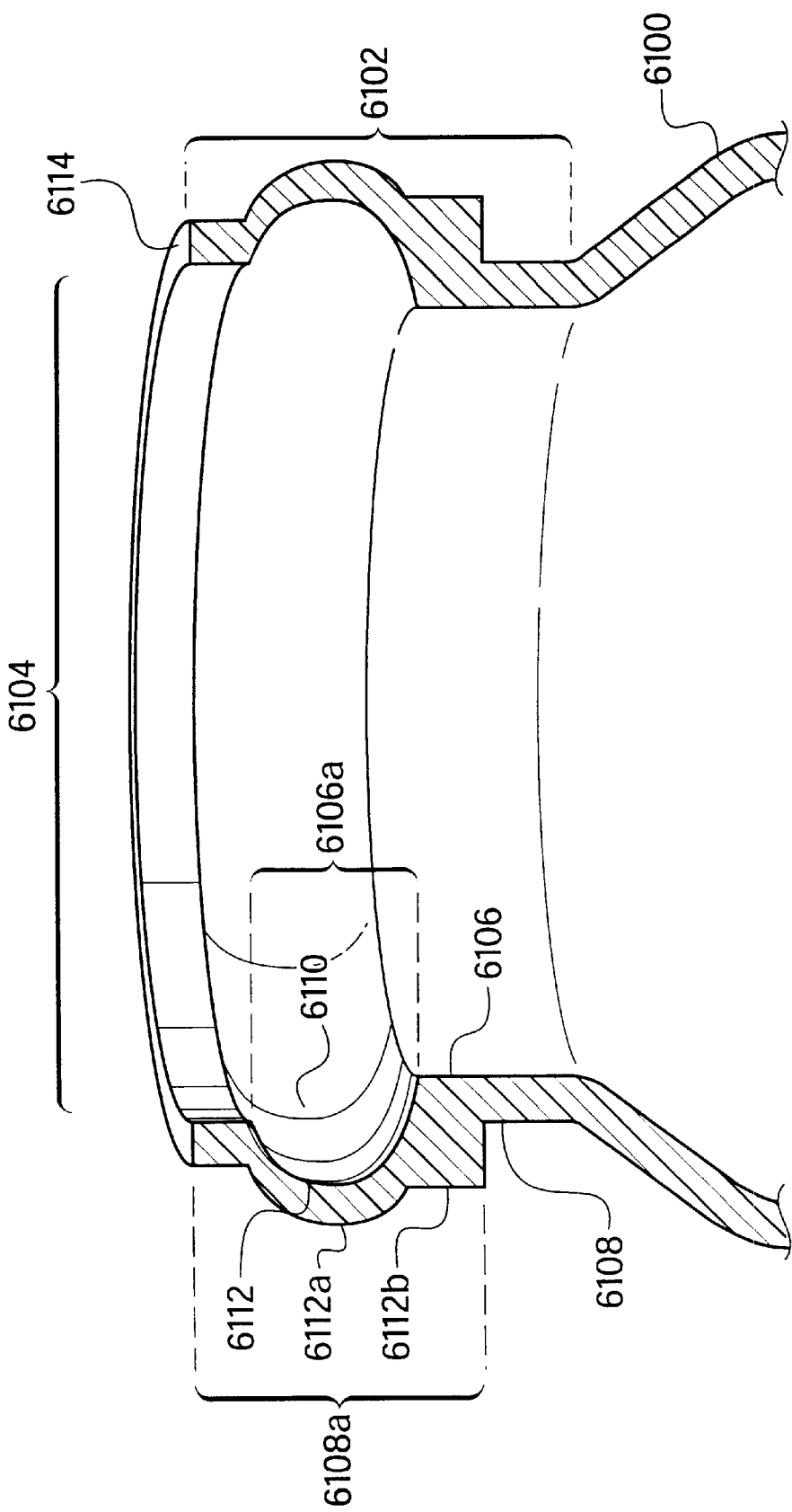
FIG. 23b is a cut-away view of the neck of the container of FIG. 23a taken along line A—A.

As shown in the cut-away view of the container 6100 illustrated in FIG. 23b, the neck 6102 includes an inner face 6106 and an outer face 6108. A substantially semicircular first recess or groove 6110 is provided on the inner face 6106 of the neck 6102 near an opening 6104 of the container 6100. The first groove 6110 may extend substantially around the entire circumference of the inner face 6106 of the neck 6102.

A first protrusion 6112 is provided on the outer face 6108 of the neck 6102, and extends substantially around the entire circumference of the outer face 6108. The first protrusion 6112 includes a substantially semicircular upper portion 6112a and a substantially angular lower portion 6112b. The upper portion 6112a of the first protrusion 6112 may be substantially vertically aligned with the substantially semi-circular first groove 6110 located on the inner face 6106 of the neck 6102 so that, in a cross-sectional view as shown in FIG. 23b, a substantially semicircular shell is formed by the first groove 6110 and the upper portion 6112a of the first protrusion 6112.

An annular rim 6114 may be provided on top of the substantially semicircular shell formed by the first groove 6110 and the first protrusion 6112. The annular rim 6114 is outwardly offset in relation to the neck 6102 of the container 6100, and the annular rim 6114 defines the opening of the container 6100.

Figure 24A:
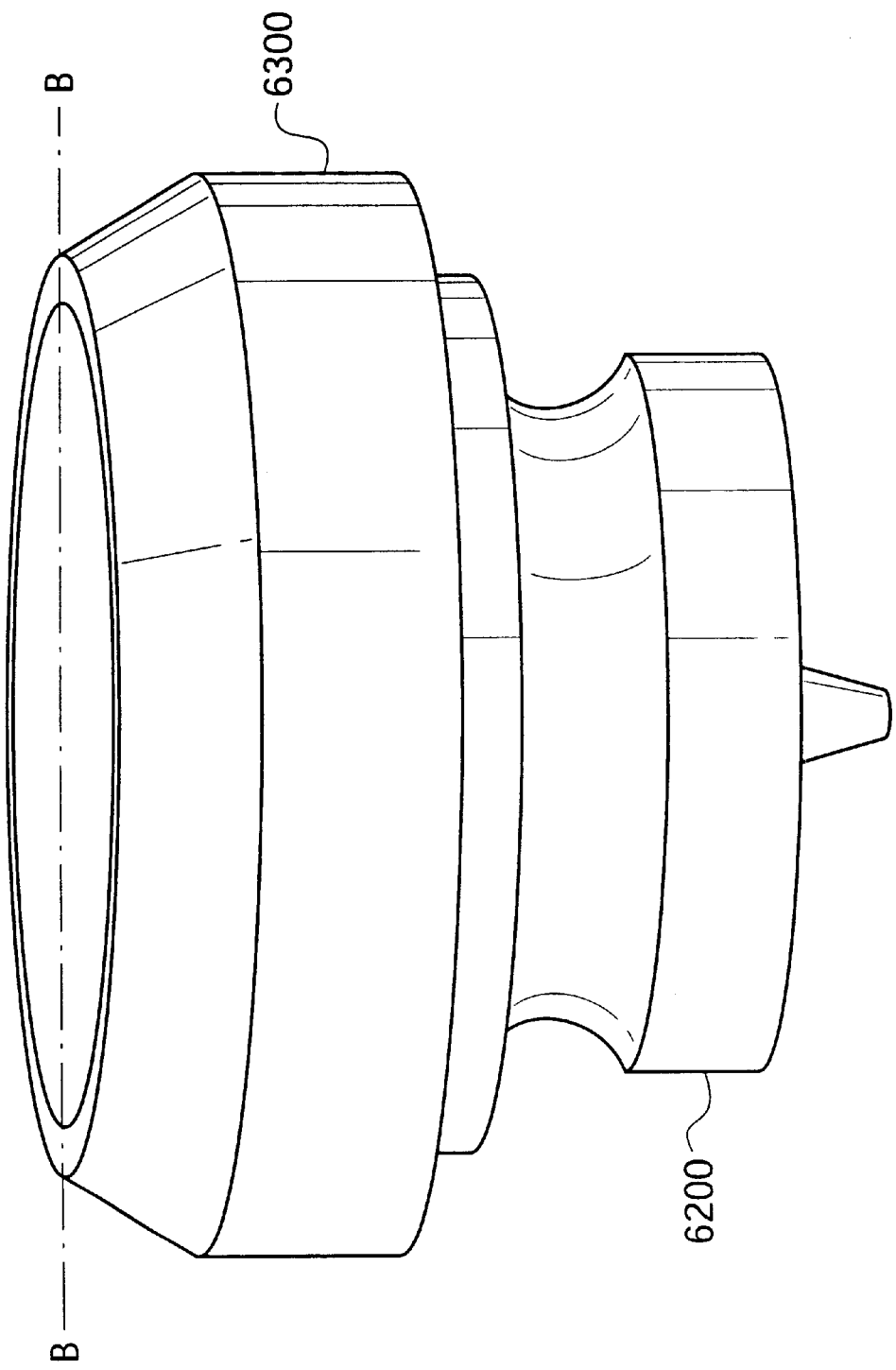
FIG. 24a is a perspective view of a mechanical plug and crimping element in accordance with the exemplary embodiment of the mechanical closure system according to the present invention.

FIG. 24a shows a further perspective view of the exemplary embodiment of the self-crimping mechanical closure system according to the present invention, which includes a rigid mechanical plug 6200 and a rigid crimping element 6300. As shown in the cut-away view of FIG. 24b, the mechanical plug 6200 is coupled to the crimping element 300 via a breakaway flange 6400. The mechanical plug 6200 includes a floor 6202, and a plug wall 6204 that extends normal to and surrounds the entire circumference of the floor 6202.

Since the mechanical plug 6200 is detachably coupled to the crimping element 6300 via the breakaway flange 6400, the mechanical plug 6200 and crimping element 6300 may be manufactured as a single-piece element. This simplifies the handling process, and the sealing process since the mechanical plug 6200 and the crimping element 6300 may be handled together. The breakaway flange 6400 may be designed or constructed of a certain material to allow for the removal and reinsertion of the mechanical plug 6200/crimping element 6300 combination from the neck 6102 of the container, and only breaking upon an application of a predetermined amount of force. Although this exemplary embodiment includes the mechanical plug 6200 and the crimping element detachably coupled together via the breakaway flange 6400, those skilled in the art will understand that other coupling mechanisms, e.g., a hinged flange, may also be implemented without departing from the scope of the present invention.

The floor 6202 of the mechanical plug 6200 has a substantially flat top surface 6202a and a bottom surface 6202b that is tapered from a radial outer edge 6202c towards a center portion 6202d of the floor 6202, so that the vertical thickness of the floor 6202 increases from the radial outer edge 6202c to the center portion 6202d. As the mechanical plug 6200 is inserted in the container 6100, the tapered shape of the bottom surface 6202b allows for any liquid content in the container to be directed towards the radial outer edge 6202c of the floor 6202. A plunger 6500 may also be provided at the center portion 6202d of the bottom surface 6202b of the floor 6202, extending substantially perpendicular to the floor 6202. This plunger 6500 would allow for further displacement of the liquid content towards the radial outer edge 6202c of the floor 6202.

As discussed above, the plug wall 6204 surrounds the circumference of the floor 6202. A substantially semicircular second protrusion 6212 is formed in an exterior surface 6210a of a lower portion 6210 of the plug wall 6204. The second protrusion 6212 may extend substantially completely around the entire circumference of the exterior surface 6210a.

Figure 24B:
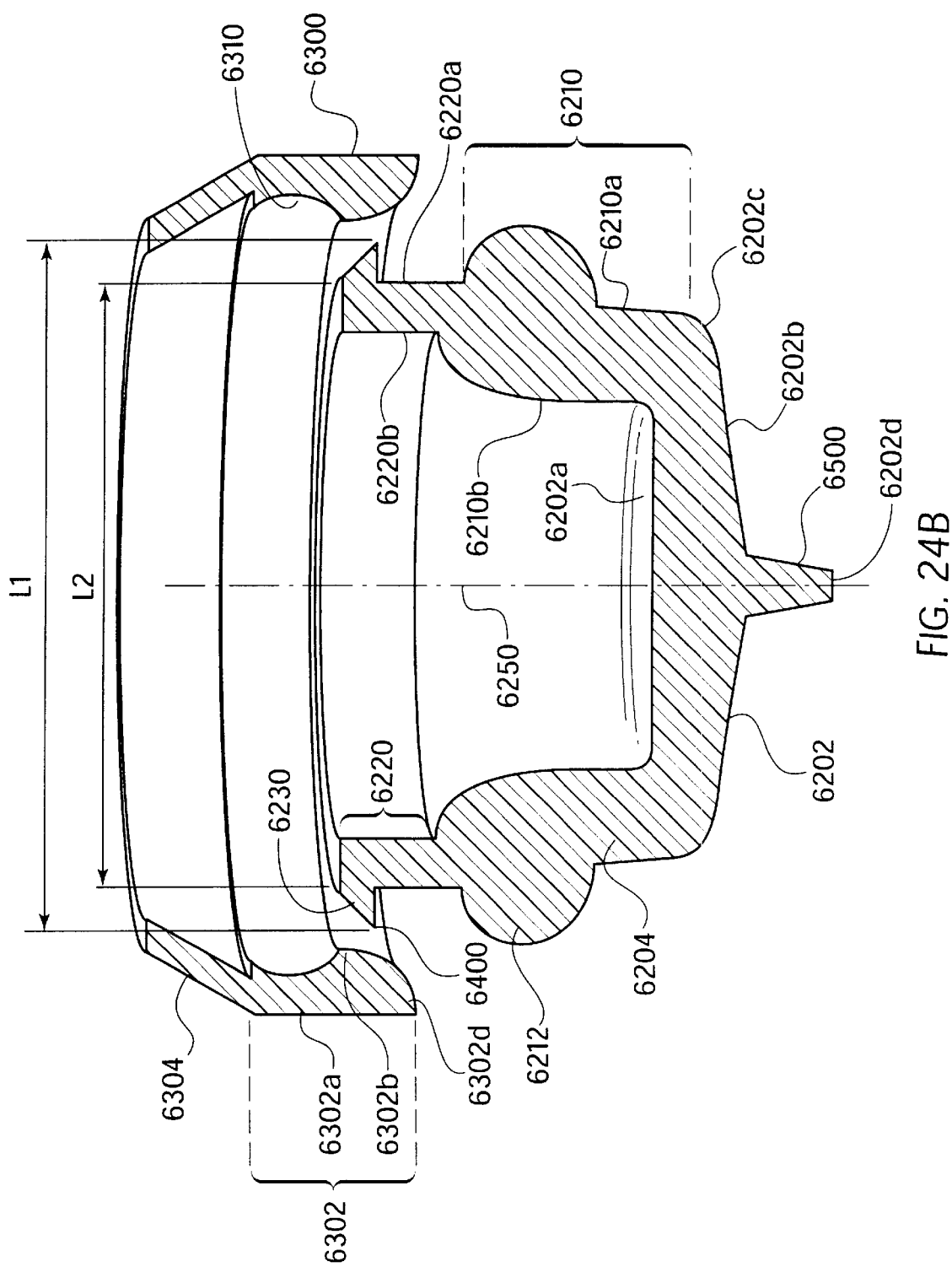
FIG. 24b is a cut-away view of the mechanical plug and crimping element of FIG. 24a taken along line B—B.

As shown in FIG. 24b, an interior surface 6210b of the lower portion 6210 of the plug wall 6204 may be initially perpendicular to the top surface 6202a of the floor 6202, and then curve away from a radial center 6250 of the floor 6202 to adjoin an interior surface 6220b of an upper portion 6220 of the plug wall 6204. The upper portion 6220 of the plug wall 6204 is substantially parallel to but offset radially outward from the interior surface 6210b of the lower portion 6210 of the plug wall.

Continuing with FIG. 24b, a cross-sectionally substantially triangular overhanging shoulder 6230 may extend from the top of the exterior surface 6220a of the plug wall 6204. A breakaway flange 6400 may be provided on the overhanging shoulder 6230 to detachably couple the mechanical plug 6200 to the crimping element 6300.

The crimping element 6300 includes a compressing ring 6302 and a conical-shaped brim 6304. An exterior surface 6302a of the compressing ring 6302 may be substantially parallel to the upper portion 6220 of the plug wall 6204. A bottom portion 6302d of the interior surface 6302b of the compressing ring 6302 may be tapered and adjoin a substantially semicircular second groove 6310 formed in the interior surface 6302b of the compressing ring 6302. The second groove 6310 may extend substantially around the entire circumference of the interior surface 6302b of the compressing ring 6302.

As shown in FIG. 24b, the brim 6304 extends from the compressing ring 6302 of the crimping element 6300 and angles into the interior of the crimping element 6300. The brim 6304 may have an inner diameter L1 that is slightly smaller than an outer diameter L2 of the overhanging shoulder 6230 on the mechanical plug 6200. L1 and L2 should be dimensioned so that the brim 6304 may be slid over the overhanging shoulder 6230 of the mechanical plug 6200 with a sufficient downward force, but then the brim 6304 will then be positioned underneath the shoulder 6230 to prevent substantial upward movement of the crimping element 6300.

Figure 25:
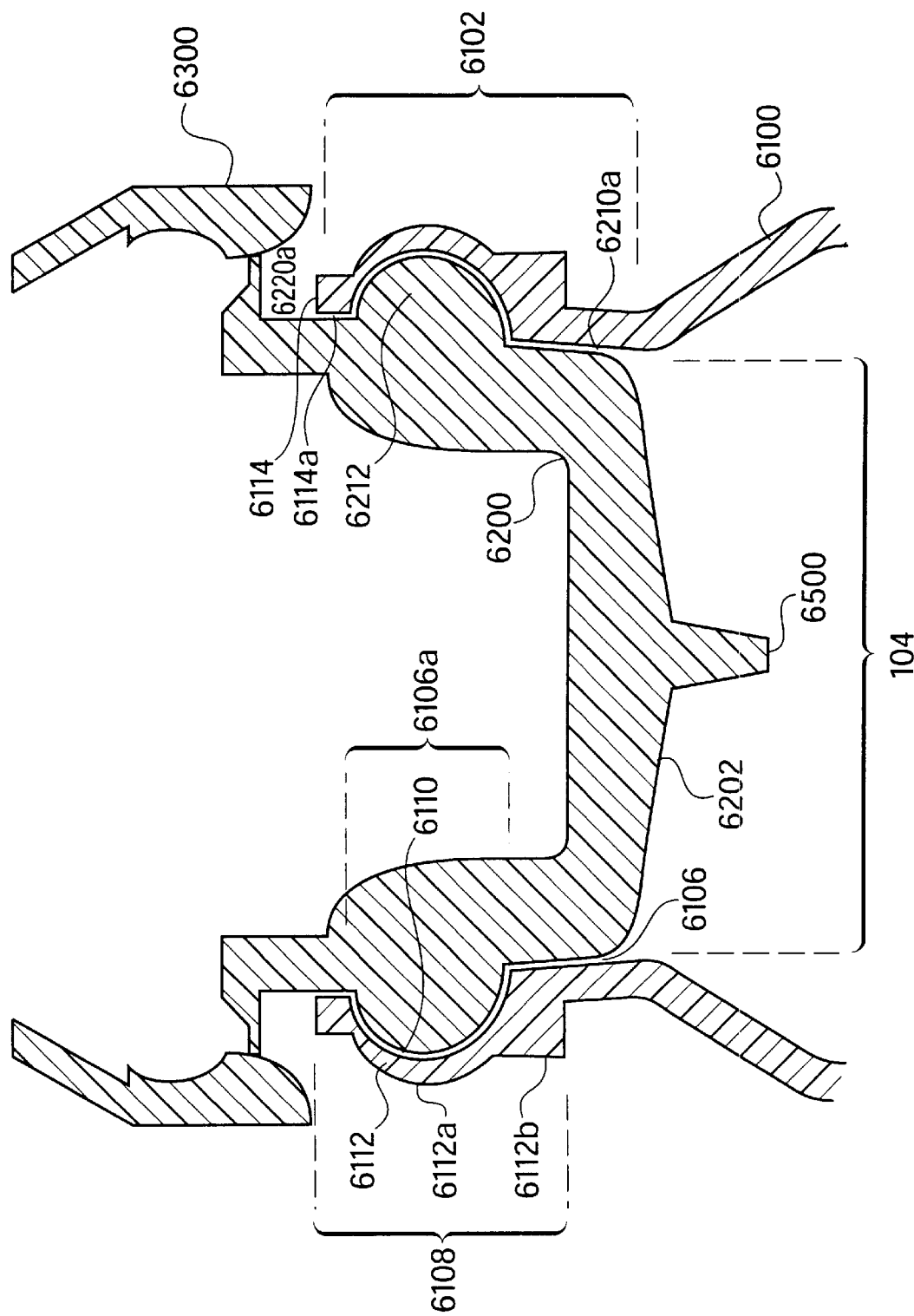
FIG. 25 is a cross-sectional view showing an interaction of the container of FIG. 23a with the mechanical plug of FIG. 24a in accordance with the present invention.

As shown in FIG. 25, which is a cross-sectional view of the mechanical plug 6200 inserted into the opening 6104 of the neck 6102 of the container 6100, the mechanical plug 6200 is inserted into the opening 6104 until the semicircular first groove 6110 on the interior surface 6106 of the neck 6102 is mated with the second protrusion 6212 on the exterior surface 6210a of the mechanical plug 6200. As discussed above, the interior surface 6106 of the neck 6102, including an interior portion 6114a of the rim 6114, and the exterior surface 6210a of the mechanical plug 6200 have been designed and proportioned so that these elements interlock as shown in FIG. 25.

The exterior surface portions 6210a, 6220a and the second protrusion 6212 of the mechanical plug 6200 may preferably be dimensioned so that, when the mechanical plug 6200 is inserted within the neck 6102 of the container, they directly abut the interior portions 6114, 6106 of the neck 6102 of the container 6100 and the first groove 6110 on the neck 6102 of the container is mated with the second protrusion 6212 of the mechanical plug. Thus, as shown in the configuration illustrated in FIG. 25, the rigidity of the mechanical plug 6200 provides substantial resistance to any inward compression of the neck 6102 of the container 6100. In addition, the interaction between the first groove 6110 on the neck 6102 and the second protrusion 6212 of the mechanical plug 6200 provides resistance to any vertical movement of the mechanical plug 6200 within the neck 6102 of the container 6100.

Of course, since the crimping element 6300 has not yet been locked into place in the configuration shown in FIG. 25, a predetermined amount of force in an upwards direction may dislodge the mechanical plug 6200 from within the neck 6102 of the container 6100. This allows the container 6100 to be transferred through potentially contaminated areas and then opened for operations such as, for example, filling the container 6100. Upon completion of the operation necessitating the removal of the mechanical plug 6200, the mechanical plug 6200 may then be re-inserted into the neck 6102 of the container 6100 and "snapped" into place as shown in FIG. 25.

In the process of inserting the mechanical plug 6200 into the neck 6102 of the container 6100, the plunger 500 on the bottom surface 6202b of the floor 6202 will also be inserted into any material, e.g., liquid, disposed within the container 6100. The insertion of the plunger 6500 into the material within the container 6200 will cause a displacement within the material which may be taken advantage of in an exemplary process according to the present invention by setting the amount of material in the container 6100 to a predetermined level so that the displacement caused by the insertion of the plunger 6500 causes the top level of the material to rise to a point directly adjacent to the bottom portion 6202 of the mechanical plug 6200. Thus, the insertion of the mechanical plug 6200 with the plunger 6500 attached thereto may cause any air bubbles or excess gas to be displaced from within the container 6100, thereby achieving a substantially airless condition within the container 6100.

Figure 26:
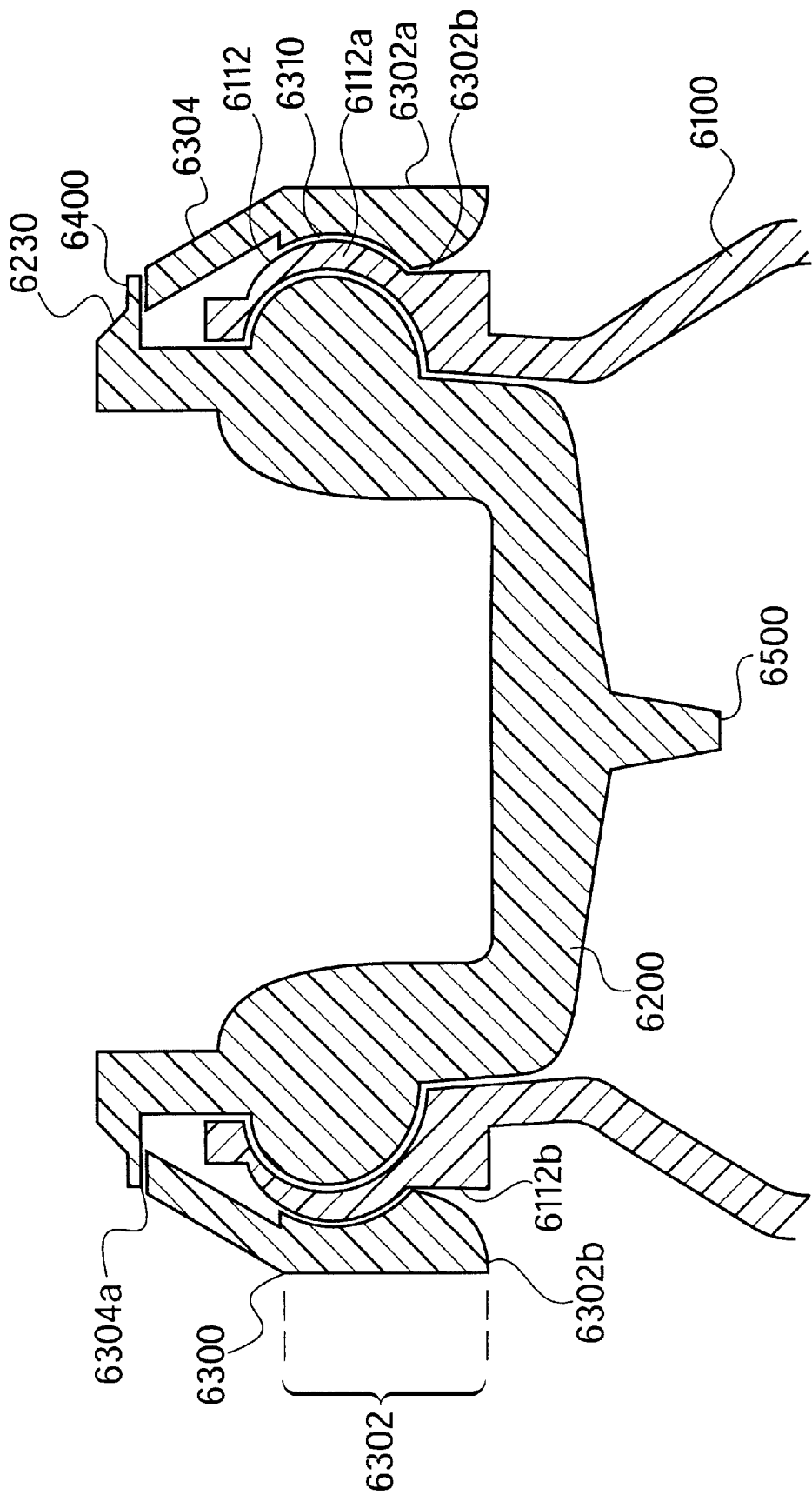
FIG. 26 is a cross-sectional view showing an interaction of the container of FIG. 23a with the mechanical plug and crimping element of FIG. 24a in accordance with the present invention.

FIG. 26 shows a cross-sectional view of a sealed configuration of the mechanical closure system according to the present invention. Starting with the configuration as shown in FIG. 25, a sufficient downward force is applied to the crimping element 6300 to break the flange 6400 that couples the crimping element 6300 to the mechanical plug 6200. The downward force applied to the crimping element 6300 should also be sufficient to slide the crimping element 6300 over the neck 6102 of the container 6100 and simultaneously "snap" the upper portion 6112a of the first protrusion 6112 on the neck 6102 of the container 6100 into the second groove 6310 on the interior surface 6302b of the crimping element 6300. The tapered shape of the bottom portion 6302d of the crimping element 6300 facilitates sliding the crimping element 6300 over the upper portion 6112a of the first protrusion 6112. Once the crimping element 6300 is slid over the neck 6102, the bottom portion 6302d of the crimping element 6300 rests against the angular bottom portion 6112b of the first protrusion 6112 on the neck 6102.

The crimping element 6300 may preferably be composed of a substantially rigid material and dimensioned to snugly encircle the neck 6102 of the container 6100. Thus, as shown in FIG. 26, the neck 6102 of the container 6100 will then be compressed between the crimping element 6300 and the plug wall 6204 of the mechanical plug 6200, thereby creating a tight, hermetic seal for the container 6100.

In the configuration shown in FIG. 26, the substantially conical shape of the brim 6304 of the crimping element 6300 and the dimensions of the brim 6304 and the overhanging shoulder 6230 on the mechanical plug 6200 allow a top section 6304a of the brim 6304 to extend underneath the overhanging shoulder 6230. This substantially prevents the crimping element 6300 from sliding up and off the neck 6102 of the container 6100, thereby further maintaining the crimping element 6300 on the neck 6102 of the container 6100.

Figure 27A:
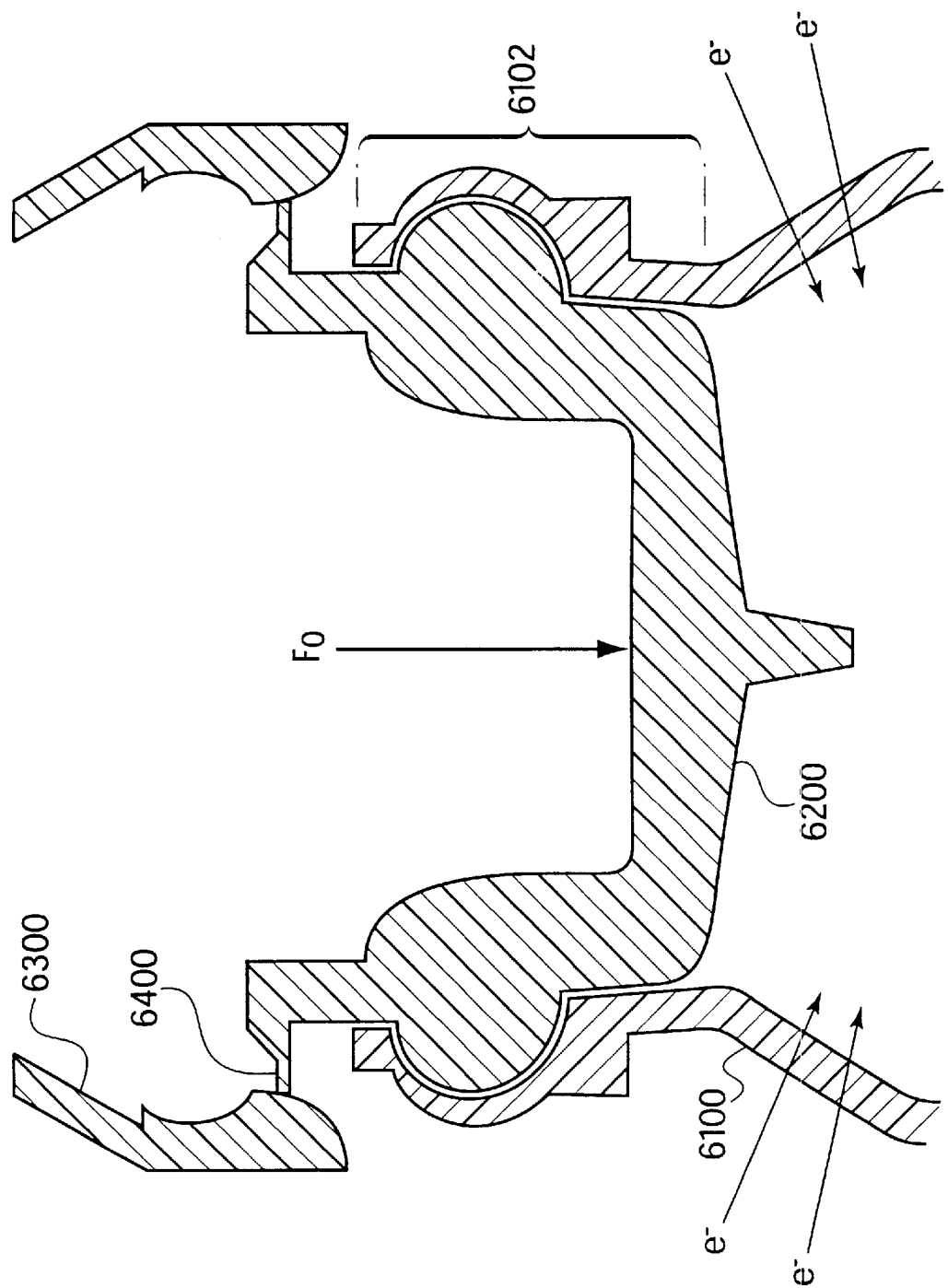
FIG. 27a shows a first step in an exemplary process for filling and sealing the container of FIG. 23a with the exemplary embodiment of the mechanical closure system according to the present invention shown in FIG. 25.

FIGS. 27a–27e illustrate, via a sequence of cross-sectional views, an exemplary process for filling and sealing the container 6100 in accordance with the present invention. FIG. 27a shows a first step in the exemplary process in which a predetermined downward force $F_0$ is applied to the mechanical plug 6200 so that the mechanical plug 6200 (with the crimping element 6300 attached via the breakaway flange 6400) is inserted into the neck 6102 of the container 6100. Although FIG. 27a shows the force $F_0$ being applied to the center of the mechanical plug 6200, those skilled in the art will understand that the force may be applied to any portion(s) of the mechanical plug 6200. This also applies to any forces illustrated in any of the drawings. Those skilled in the art will also understand that any "downward" and "upward" direction for applying the forces is relative to the orientation of the container 6100.

Once the mechanical plug 6200 has been fully inserted, the container 6100 may then be irradiated to sterilize the container. The container 6100 with the mechanical plug 6200 inserted therein may then be conveyed to, for example, a filling machine, which is not shown. Since the mechanical plug 6200 is still inserted within the neck 6102 of the container 6100, the interior of the container 6100 is protected from outside contaminants during the transfer.

Figure 27B:
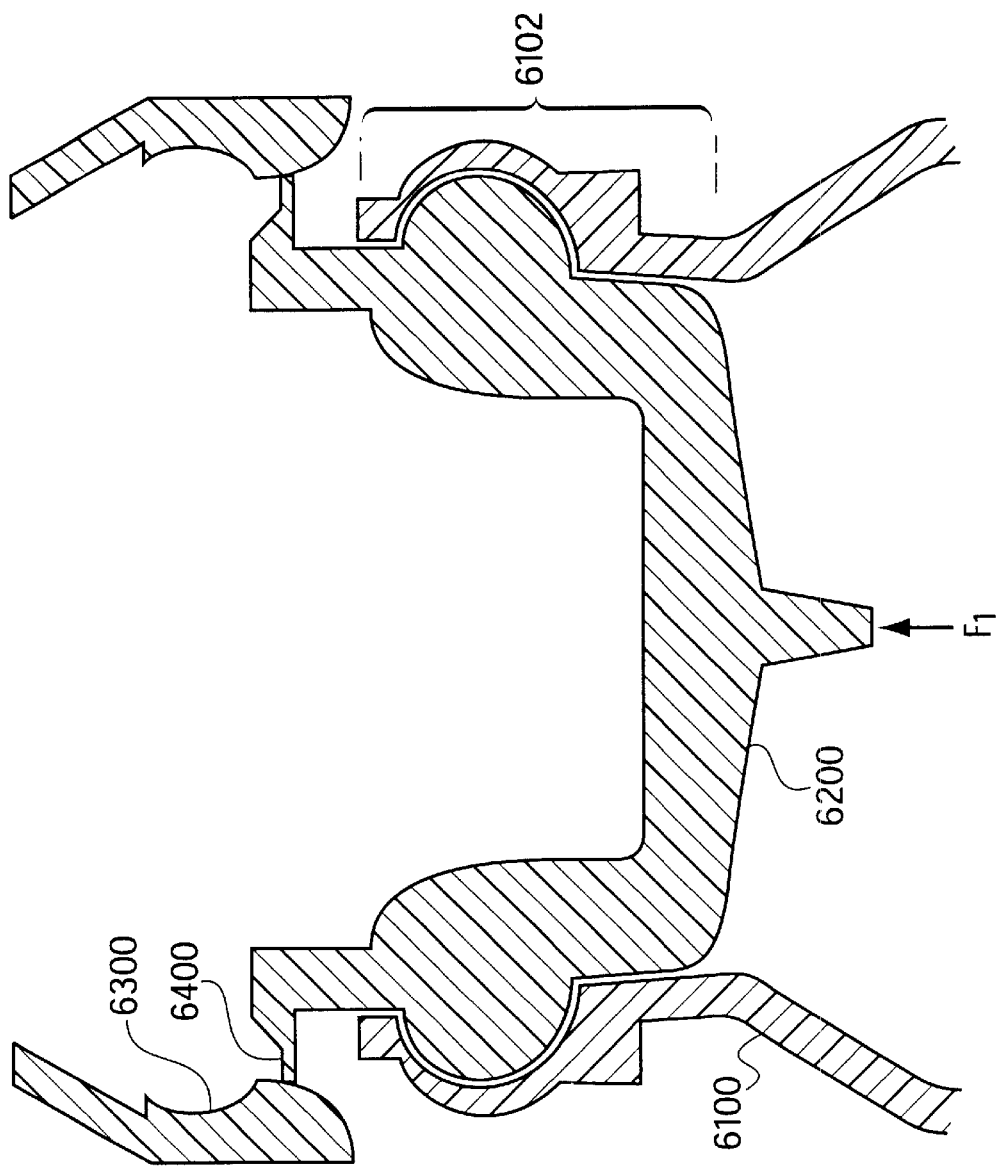
FIG. 27b shows a second step in the exemplary process for filling and sealing the container of FIG. 23a with the exemplary embodiment of the mechanical closure system according to the present invention shown in FIG. 25.
Figure 27C:
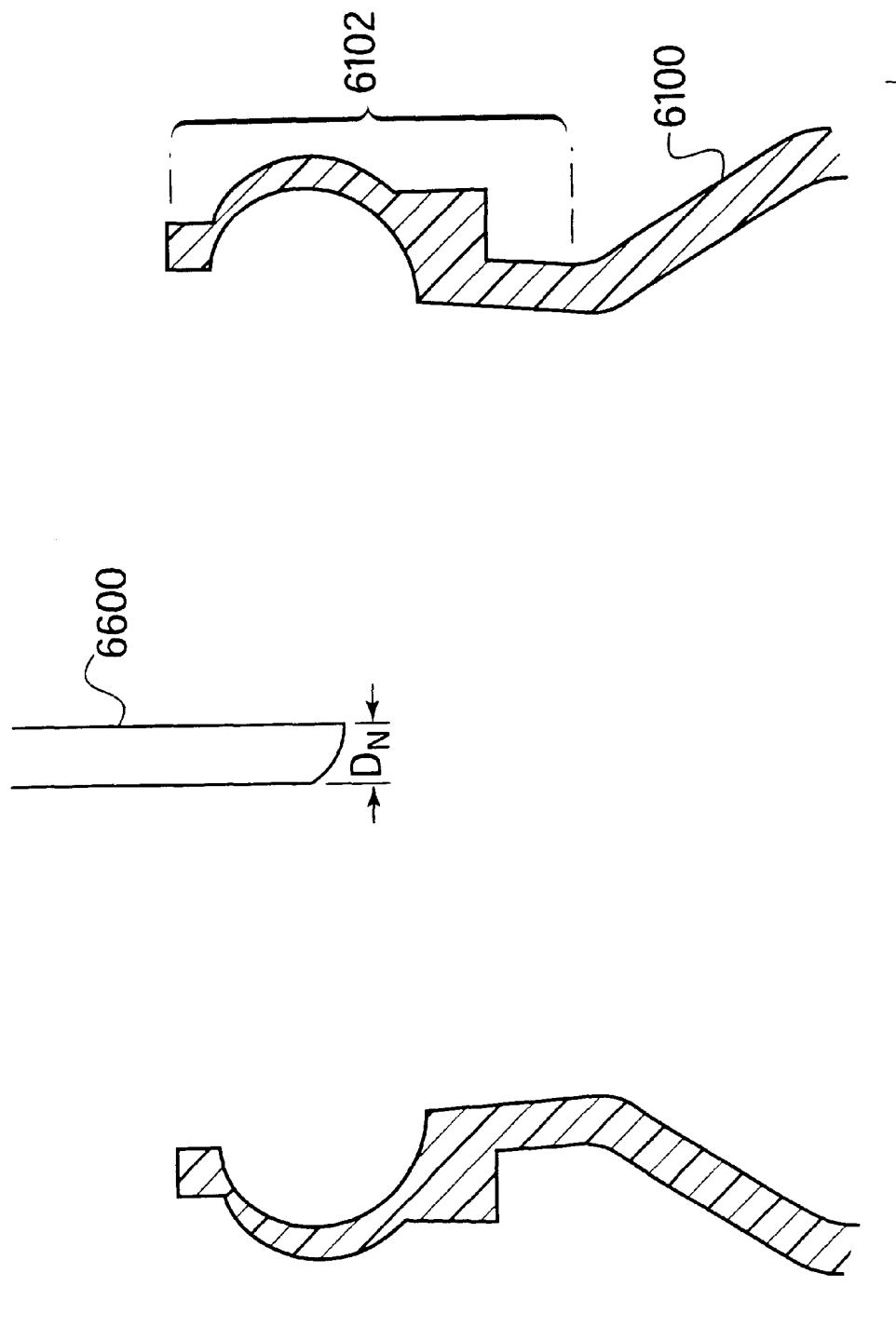
FIG. 27c shows a third step in the exemplary process for filling and sealing the container of FIG. 23a with the exemplary embodiment of the mechanical closure system according to the present invention shown in FIG. 25.

In the next step, shown in FIG. 27b, a predetermined upwards force $F_1$ is applied to the mechanical plug 6200 in order to remove the mechanical plug 6200 from the container 6100. The removal of the mechanical plug 6200 is possible because the crimping element 6300 has not been slid over the neck 6102 of the container at this stage. Then, in the next step, shown in FIG. 27c, a conventional needle 6600 of the filling machine, which is not shown, may be used to fill the container 6100 with whatever desired material.

In conventional filling machines, a diameter $D_N$ of the needle 6600 needs to be minimized to reduce the size of the puncture point through the mechanical plug 6200 because the puncture point needs to be then sealed with an external sealing agent. However, since the mechanical plug 6200 is removable in the mechanical closure system according to the present invention and there is no puncture point, the diameter $D_N$ of the needle 6600 can be almost as wide as the opening 6104 of the container 6100. This enables faster filling times than in conventional systems, which allows for faster cycle times for filling multiple containers 6100.

Figure 27D:
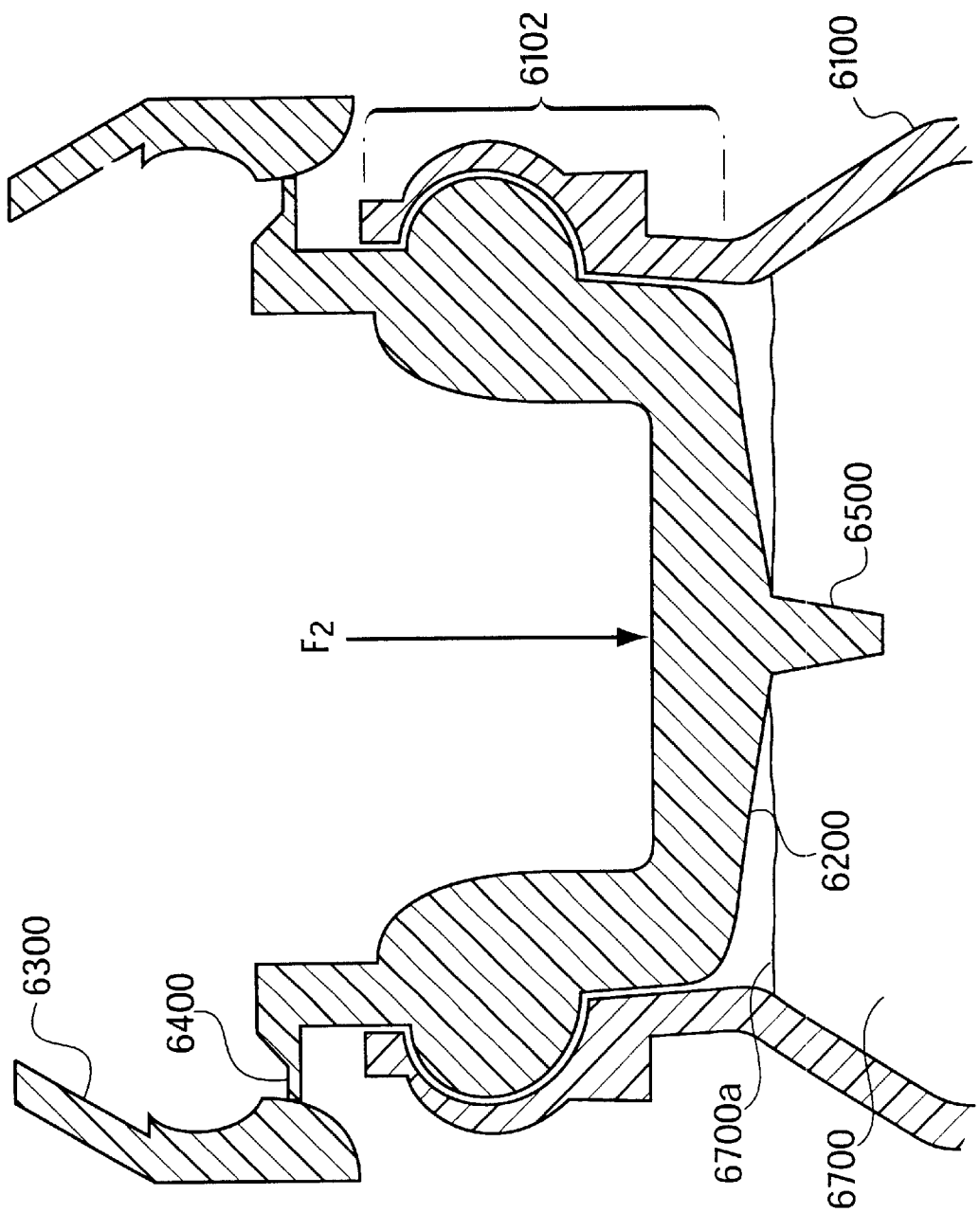
FIG. 27d shows a fourth step in the exemplary process for filling and sealing the container of FIG. 23a with the exemplary embodiment of the mechanical closure system according to the present invention shown in FIG. 25.

In the next step, shown in FIG. 27d, a predetermined downward force $F_2$ is applied to the mechanical plug 6200 to re-insert the mechanical plug 6200 into the neck 6102 of the container 6100. In the process of re-inserting the mechanical plug 6200, the plunger 6500 that is provided on the bottom surface 6202b of the mechanical plug 6200 is also inserted into the material 6700 that has been received within the container 6100. As a result, a surface level 6700a of the material 6700 is raised, which may be advantageously exploited to substantially eliminate the amount of air or excess gas in the container 6100.

Figure 27E:
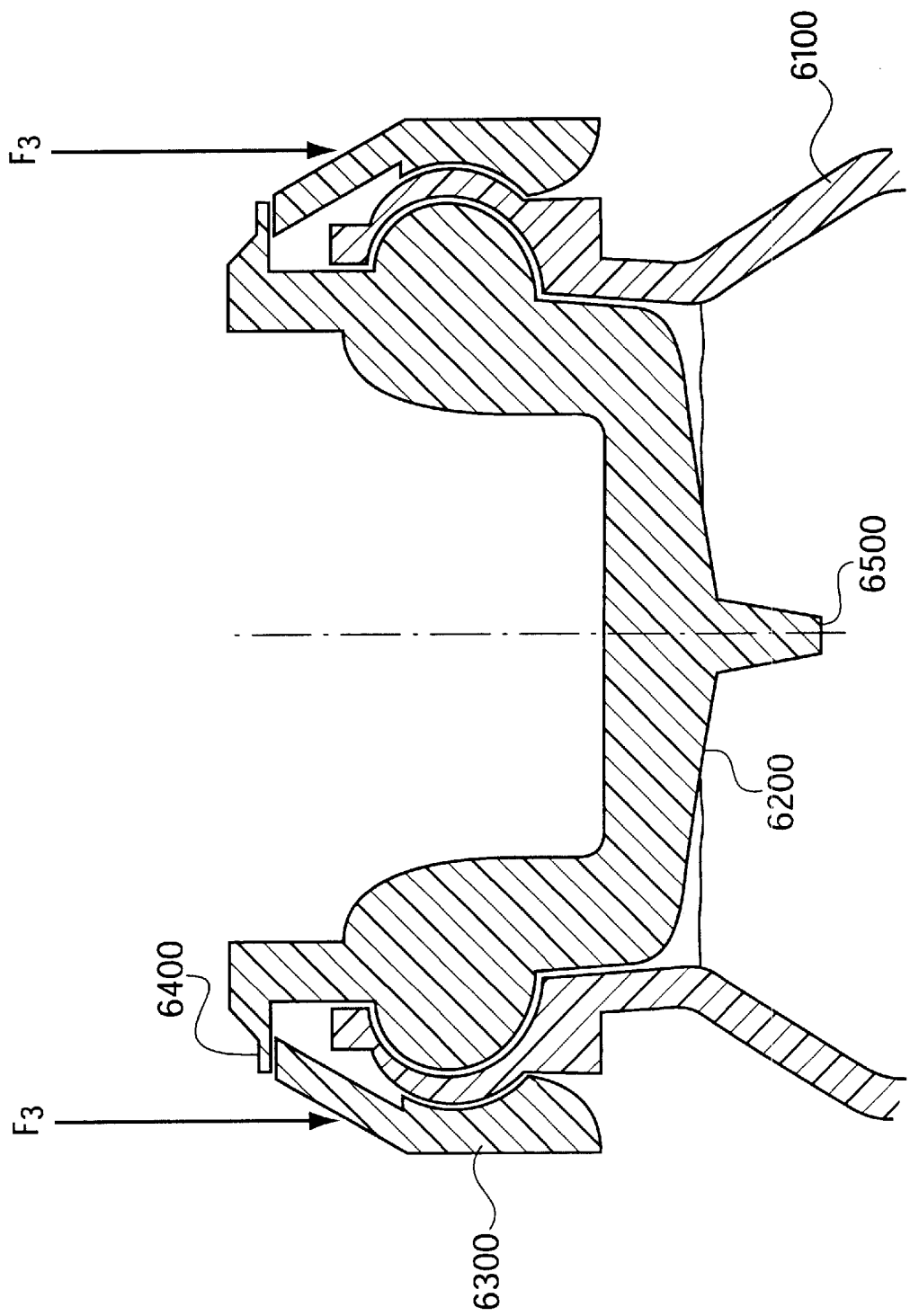
FIG. 27e shows a fifth step in the exemplary process for filling and sealing the container of FIG. 23a with the exemplary embodiment of the mechanical closure system according to the present invention shown in FIG. 25.

Subsequently, a predetermined force $F_3$ may be applied to the crimping element 6300 as shown in FIG. 27e, which results in a separation of the crimping element 6300 from the mechanical plug 6200 at the flange 6400. The force $F_3$ may also be sufficient to cause the crimping element 6300 to slide over the neck 6102 of the container 6100. The interaction of the crimping element 6300, the neck 6102 of the container, and the mechanical plug 6200, as described above with respect to FIG. 26, may then provide the container 6100 with a tight, hermetic seal.

In this exemplary process, the detachable arrangement of the mechanical plug 6200 relative to the crimping element 6300 allows the container to be temporarily closed when only the mechanical plug 6200 is operatively engaging the neck 6102 of the container 6100. This prevents contamination during transportation or transfers, and allows certain operations requiring access to the interior of the container 6100 to be performed before finally sealing the container 6100 with the crimping element 6300. For example, the container 6100 may be exposed to heat or radiation to decontaminate the container 6100, or the container 6100 may be filled with a liquid content.

As an alternative to the above-described exemplary process, the forces $F_2$ and $F_3$ may be replaced with a single force applied to both the mechanical plug 6200 and the crimping element 6300, which would result in the simultaneous insertion of the mechanical plug 6200 into the neck 6102 of the container 6100 and sliding the crimping element 6300 over the neck 6102 of the container 6100.

In the foregoing specification, the invention has been described with reference to specific exemplary embodiments thereof. It will, however, be evident that various modifications and changes may be made thereto without departing from the broader spirit and scope of the invention as set forth in the appended claims. For example, the cartridge or housing may be adapted for use in conjunction with various types of vial-dispensers not specifically described herein, for example the vial-dispenser which is described in my U.S. Pat. No. 5,613,957 which has been expressly incorporated herein by reference. Furthermore, the spring action provided by flexible plastic material forming the front and rear bellows, shown in FIG. 15, may be alternatively provided by a longitudinally disposed spring which urges the vial-dispenser to return to original position upon being released from the compressed state. In addition, although the vial-dispenser has been described in this specification as having an accordion-like front bellows portion and a rear bellows portion, the dispenser may alternatively incorporate any other spring configuration, e.g., a single spring element which is either integral with the dispenser body or separately formed. Furthermore, the specific arrangement of the trigger 1103, the notched lever 4102 and the wedge-shaped arm 4103 may be modified, e.g., the trigger 1103 and the notched lever 4102 may be formed separately from one another and/or from the cartridge 4101. Still yet, while the mechanical closure system according to the present invention have been described as being adapted for a container or vial having a circular opening, the mechanical closure system according to the present invention may be adapted for openings of other shapes, e.g., square or rectangle. The specification and drawings are accordingly to be regarded in an illustrative rather than a restrictive sense.

I claim:

1. A dispensing system for delivery of medicament to a nasal passage, which comprises:

a vial for holding a volume of medicament;

a pump having an outlet in a nozzle portion and an elastic, deformable body portion connected to said nozzle portion, said body portion containing a piston mechanism and a dosage cavity of a predetermined volume for collecting medicament from said vial, said nozzle portion having a rigid shaft received therein and interfacing said outlet to form a first normally-closed valve;

a housing retaining said vial and said pump, said housing exposing said outlet, and said housing having a guide element for aligning, when in a first position, said outlet with said nasal passage and screening said nasal passage from view;

a trigger operationally coupled to said housing for actuating, by a single actuating motion of said trigger, said dispensing system to sequentially fill said dosage cavity with medicament from said vial and subsequently discharge said medicament from said dosage cavity;

a lever operationally coupled to said trigger and releasably engaging said deformable body portion when said body portion is in ambient position, said lever being movable to a first non-ambient position in concert with a first phase of said actuating motion of said trigger and deforming at least a portion of said deformable body portion to cause flow of medicament from said vial to said dosage cavity to fill said dosage cavity; and a release arm internally positioned in the housing to oppose said lever at said first non-ambient position so as to disengage said lever from said deformable body portion upon continuation of said actuating motion into a second phase, wherein said elastic, deformable body portion returns to said ambient position upon disengagement from said lever to pressurize medicament in said dosage cavity and discharge said medicament through said outlet of said nozzle portion.

2. The system according to claim 1, wherein said elastic, deformable body portion comprises one of a bellows-shaped portion and a dome-shaped portion, and wherein said rigid shaft and interior of said nozzle portion define a swirling chamber for said medicament prior to expulsion via said outlet, and wherein said piston mechanism is operatively coupled to said deformable body portion to move along longitudinal axis of the pump in connection with deformation of the deformable body portion along its longitudinal axis, displacement of said piston mechanism corresponding to displacement of the lever between said ambient position and said first non-ambient position.

3. The system according to claim 2, wherein said guide element is pivotably coupled to said housing, said guide element, when in a second position, substantially covering said outlet, and wherein said nozzle portion has a wall thickness which decreases from a first point along a direction Qf elongated axis of symmetry of said nozzle portion toward a tip of the nozzle portion.

4. The system according to claim 3, wherein said trigger is actuated in the direction perpendicular to the longitudinal axis of said housing.

5. The system according to claim 4, wherein said trigger and said lever are integrally formed.

6. The system according to claim 5, wherein said medicament in said swirling chamber is expelled via said first normally-closed valve upon reaching a threshold pressure sufficient to radially deform said nozzle portion to open said first normally-closed valve.

7. The system according to claim 6, wherein said one of said bellows-shaped portion and said dome-shaped portion is made of thermoplastic material.

8. The system according to claim 7, wherein said housing is substantially rigid, said housing preventing deformation of said nozzle portion along said axial direction during expulsion of said medicament from said swirling chamber via said outlet.

9. The system according to claim 2, wherein said nozzle portion further comprises a fluid channel defining a portion of a fluid communication path between said dosage cavity and said swirling chamber, said channel inducing swirling action of medicament channeled to said swirling chamber.

10. The system according to claim 9, wherein said deformable body portion comprises at least one bellows-shaped portion made of thermoplastic material.

11. The system according to claim 10, wherein said guide element is pivotably coupled to said housing, said guide element, when in a second position, substantially covering said outlet.

12. The system according to claim 11, wherein said trigger is actuated in the direction perpendicular to the longitudinal axis of said housing.

13. The system according to claim 12, wherein said trigger and said lever are integrally formed.

14. The system according to claim 13, wherein said medicament in said swirling chamber is expelled via said first normally-closed valve upon reaching a threshold pressure sufficient to radially deform said nozzle portion to open said first normally-closed valve.

15. The system according to claim 14, wherein said bellows-shaped portion is made of Kraton™.

16. The system according to claim 15, wherein said housing is substantially rigid, said housing preventing deformation of said nozzle portion along said axial direction during expulsion of said medicament from said swirling chamber via said outlet.

17. The system according to claim 9, wherein said fluid channel comprises a vertical portion extending along the radial edge of said nozzle portion.

18. The system according to claim 17, wherein said deformable body portion comprises at least one bellows-shaped portion made of thermoplastic material.

19. The system according to claim 18, wherein said guide element is pivotably coupled to said housing, said guide element, when in a second position, substantially covering said outlet.

20. The system according to claim 19, wherein said trigger is actuated in the direction perpendicular to the longitudinal axis of said housing.

21. The system according to claim 20, wherein said trigger and said lever are integrally formed.

22. The system according to claim 21, wherein said medicament in said swirling chamber is expelled via said first normally-closed valve upon reaching a threshold pressure sufficient to radially deform said nozzle portion to open said first normally-closed valve.

23. The system according to claim 22, wherein said bellows--shaped portion is made of Kraton™.

24. The system according to claim 23, wherein said housing is substantially rigid, said housing preventing deformation of said nozzle portion and said fluid channel along said axial direction during expulsion of said medicament from said swirling chamber via said outlet.

25. The system according to claim 1, wherein said vial has an opening at a neck region of said vial, which system further comprises:
   a rigid ring for operatively engaging an interior surface of said neck region of said vial; and
   a mechanical plug for operatively and simultaneously engaging an exterior surface of said neck region of said vial and said interior annular surface of said rigid ring, said mechanical plug having a leg extending substantially perpendicular to a bottom surface of the mechanical plug for operatively engaging a bottom surface of said rigid ring;
   whereby said mechanical plug and said rigid ring provide a mechanical seal of said vial opening by simultaneously engaging at least a portion of said neck region of said vial.

26. The system according to claim 25, wherein said mechanical plug and said rigid ring provide a horizontal compression of said neck region of said vial to achieve a seal along the vertical dimension of the neck region.

27. The system according to claim 26, wherein said mechanical plug and said rigid ring provide a vertical compression of said neck region of said vial to achieve a seal along the horizontal dimension of the neck region.

28. The system according to claim 3, wherein said vial has an opening at a neck region of said vial, which system further comprises:
   a rigid ring for operatively engaging an interior surface of said neck region of said vial; and
   a mechanical plug for operatively and simultaneously engaging an exterior surface of said neck region of said vial and said interior annular surface of said rigid ring, said mechanical plug having a leg extending substantially perpendicular to a bottom surface of the mechanical plug for operatively engaging a bottom surface of said rigid ring;
   whereby said mechanical plug and said rigid ring provide a mechanical seal of said vial opening by simultaneously engaging at least a portion of said neck region of said vial.

29. The system according to claim 9, wherein said vial has an opening at a neck region of said vial, which system further comprises:
   a rigid ring for operatively engaging an interior surface of said neck region of said vial; and
   a mechanical plug for operatively and simultaneously engaging an exterior surface of said neck region of said vial and said interior annular surface of said rigid ring, said mechanical plug having a leg extending substantially perpendicular to a bottom surface of the mechanical plug for operatively engaging a bottom surface Of said rigid ring;
   whereby said mechanical plug and said rigid ring provide a mechanical seal of said vial opening by simultaneously engaging at least a portion of said neck region of said vial.

30. The system according to claim 1, wherein said vial has an opening at a neck region of said vial, which system further comprises:
   a mechanical plug; and
   a crimping element repositionably coupled to the mechanical plug via a flange;
   wherein the mechanical plug and the crimping element operatively interact with the neck region to seal the vial.

31. The system according to claim 30, wherein:
   in a first configuration, the crimping element is coupled to the mechanical plug, and the mechanical plug detachably engages with an interior surface of the neck region of the vial to removably seal the opening of the vial;
   and wherein, in a second configuration, the mechanical plug engages the interior surface of the neck region of the vial, and the crimping element is repositioned relative to the mechanical plug and engages an exterior surface of the neck region of the vial to seal the opening of the vial in conjunction with the mechanical plug.

32. The system according to claim 3, wherein said vial has an opening at a neck region of said vial, which system further comprises:
   a mechanical plug; and
   a crimping element repositionably coupled to the mechanical plug via a flange;
   wherein the mechanical plug and the crimping element operatively interact with the neck region to seal the vial.

33. The system according to claim 32, wherein:
   in a first configuration, the crimping element is coupled to the mechanical plug, and the mechanical plug detachably engages with an interior surface of the neck region of the vial to removably seal the opening of the vial;
   and wherein, in a second configuration, the mechanical plug engages the interior surface of the neck region of the vial, and the crimping element is repositioned relative to the mechanical plug and engages an exterior surface of the neck region of the vial to seal the opening of the vial in conjunction with the mechanical plug.

34. The system according to claim 9, wherein said vial has an opening at a neck region of said vial, which system further comprises:
   a mechanical plug; and
   a crimping element repositionably coupled to the mechanical plug via a flange;
   wherein the mechanical plug and the crimping element operatively interact with the neck region to seal the vial.

35. The system according to claim 34, wherein:
   in a first configuration, the crimping element is coupled to the mechanical plug, and the mechanical plug detachably engages with an interior surface of the neck region of the vial to removably seal the opening of the vial;
   and wherein, in a second configuration, the mechanical plug engages the interior surface of the neck region of the vial, and the crimping element is repositioned relative to the mechanical plug and engages an exterior surface of the neck region of the vial to seal the opening of the vial in conjunction with the mechanical plug.

36. The system according to claim 1, wherein said deformable body portion comprises an elastomeric material providing spring action which enables said deformable body portion to return to said ambient position from said first non-ambient position, and wherein said rigid shaft and interior of said nozzle portion define a swirling chamber for said medicament prior to expulsion via said outlet.

37. The system according to claim 36, wherein said deformable body portion comprises one of a bellows-shaped portion and a dome-shaped portion.

38. The system according to claim 36, wherein said deformable body portion is made of a thermoplastic material.

39. The system according to claim 36, wherein said nozzle portion further comprises at least one fluid channel defining a portion of a fluid communication path between said dosage cavity and said swirling chamber, said channel inducing swirling action of medicament channeled to said swirling chamber.

40. The system according to claim 39, wherein said fluid channel comprises a vertical portion extending along the radial edge of said nozzle portion.

41. The system according to claim 40, wherein said fluid channel further comprises horizontal portion extending from said vertical portion towards the radial center of said nozzle portion to connect with said swirling chamber.

42. The system according to claim 41, wherein said nozzle portion has a plurality of fluid channels each having a vertical portion and a horizontal portion, each of said horizontal portions being connected to said swirling chamber.

43. The system according to claim 42, wherein each horizontal portion of said fluid channels has a width that decreases in the direction from the radial edge of the nozzle portion towards said swirling chamber.

44. The system according to claim 42, wherein said swirling chamber is substantially circular and said horizontal portions of said fluid channels are connected to said swirling chamber tangentially.

45. The system according to claim 44, wherein a floor of a portion of said swirling chamber at which any one said horizontal portions converge with said swirling chamber is higher than a floor of the converging horizontal portion.

46. A dispensing system for the delivery of medicament to nasal passage, which comprises:

a vial for holding a volume of medicament;

a pump having an outlet in a nozzle portion, an elastic, deformable body portion connected to said nozzle portion and containing a piston mechanism and a dosage cavity of a predetermined volume for collecting medicament from said vial, and a fluid inlet orifice in fluid communication with said vial and said dosage cavity, said piston mechanism being operatively coupled to said deformable body portion to move along longitudinal axis of the pump in connection with deformation of the deformable body portion along its longitudinal axis, said nozzle portion having a wall thickness which decreases from a first point along a direction of elongated axis of symmetry of said nozzle portion toward a tip of the nozzle portion, and said nozzle portion having a rigid shaft received therein and interfacing said outlet to form a first normally-closed valve, said rigid shaft and interior of said nozzle portion defining a swirling chamber for said medicament prior to expulsion via said outlet;

a housing retaining said vial and said pump, said housing exposing said outlet, and said housing having a guide element for aligning, when in a first position, said outlet with said nasal passage and screening said nasal passage from view;

a trigger operationally coupled to said housing for actuating, by a single actuating motion of said trigger, said dispensing system to sequentially fill said dosage cavity with medicament from said vial and subsequently discharge said medicament from said dosage cavity;

a lever operationally coupled to said trigger and releasably engaging said deformable body portion when said body portion is in ambient position, said lever being movable to a first non-ambient position in concert with a first phase of said actuating motion of said trigger and deforming at least a portion of said deformable body portion, and in concert moving said piston mechanism, along the longitudinal axis towards the posterior end of said housing, displacement of said piston mechanism corresponding to displacement of the lever between said ambient position and said first non-ambient position causing flow of medicament from said vial to said dosage cavity to fill said dosage cavity; and a release arm internally positioned in the housing to oppose said lever at said first non-ambient position so as to disengage said lever from said deformable body portion upon continuation of said actuating motion into a second phase, wherein said deformable body portion returns to said ambient position upon disengagement from said lever and said piston mechanism moves in concert with said deformable body portion towards said nozzle portion to pressurize medicament in said dosage cavity and discharge said medicament through said outlet of said nozzle portion.

47. A method of delivering medicament to nasal passage by means of a medicament dispensing system having a medicament vial; a pump with an outlet defined by a first normally-closed valve, a swirling chamber in a nozzle portion, and an elastic, deformable body portion connected to said nozzle portion, said body portion containing a piston mechanism and a dosage cavity of a predetermined volume for collecting medicament from said vial, and a fluid channel between said dosage cavity and said swirling chamber; a housing retaining said vial and said pump; a trigger operationally coupled to said housing for actuating said dispensing system; a lever operationally coupled to said trigger and releasably engaging said deformable body portion; and a release arm internally positioned in the housing; which method comprises:

channeling medicament from said vial to said dosage cavity by actuating said trigger through a first phase of a single continuous actuating motion whereby said lever is moved from an ambient position to a first non-ambient position in concert with said first phase of said single continuous actuating motion and deforms at least a portion of said elastic, deformable body portion;

actuating said trigger through a second phase of said single continuous actuating motion whereby said lever is opposed by said release arm at said first non-ambient position so as to disengage said lever from said deformable body portion;

pressurizing said medicament in said dosage cavity to create medicament flow to said swirling chamber via said fluid channel by means of initiating a return movement of said elastic, deformable body portion to said ambient position upon disengagement from said lever;

generating swirling of said medicament within said swirling chamber by means of tangential connection of said fluid channel to said swirling chamber; and discharging said medicament from said swirling chamber through said first normally-closed valve by means of completing said return movement of said deformable body portion to said ambient position and pressurizing said medicament to reach a threshold pressure sufficient to open said first normally-closed valve.

* * * * *